(12) United States Patent
Gee et al.

(10) Patent No.: US 10,739,330 B2
(45) Date of Patent: Aug. 11, 2020

(54) CARBOPYRONONE COMPOUNDS USEFUL AS DIAGNOSTIC ADJUVANTS

(71) Applicant: LIFE TECHNOLOGIES CORPORATION, Carlsbad, CA (US)

(72) Inventors: Kyle Gee, Springfield, OR (US); Hee Chol Kang, Eugene, OR (US); Wenjun Zhou, Eugene, OR (US); Bradley Dubbels, Roanoke, VA (US); Michael Olszowy, Boulder, CO (US); Michael O'Grady, Eugene, OR (US)

(73) Assignee: Life Technologies Corporation, Carslbad, CA (US)

( * ) Notice: Subject to any disclaimer, the term of this patent is extended or adjusted under 35 U.S.C. 154(b) by 0 days.

(21) Appl. No.: 16/002,991

(22) Filed: Jun. 7, 2018

(65) Prior Publication Data

US 2018/0340928 A1    Nov. 29, 2018

Related U.S. Application Data

(62) Division of application No. 15/304,800, filed as application No. PCT/US2015/030956 on May 15, 2015, now Pat. No. 10,018,617.

(60) Provisional application No. 61/994,555, filed on May 16, 2014.

(51) Int. Cl.
| | | |
|---|---|---|
| *G01N 33/50* | (2006.01) | |
| *C09B 11/28* | (2006.01) | |
| *C07K 16/28* | (2006.01) | |
| *C07C 309/61* | (2006.01) | |
| *C07D 471/04* | (2006.01) | |

(52) U.S. Cl.
CPC ....... *G01N 33/5005* (2013.01); *C07C 309/61* (2013.01); *C07D 471/04* (2013.01); *C07K 16/2812* (2013.01); *C09B 11/28* (2013.01); *G01N 33/5014* (2013.01); *G01N 33/5044* (2013.01); *C07C 2603/24* (2017.05)

(58) Field of Classification Search
CPC .......... G01N 33/5005; G01N 33/5044; G01N 33/5014; C09B 11/28; C07K 16/2812; C07C 309/61; C07C 2603/24; C07D 471/04

See application file for complete search history.

(56) References Cited

U.S. PATENT DOCUMENTS

| | | | |
|---|---|---|---|
| 5,686,261 A | 11/1997 | Zhang et al. | |
| 6,828,159 B1 * | 12/2004 | Drexhage | G01N 33/582 435/6.12 |
| 10,018,617 B2 | 7/2018 | Gee et al. | |

FOREIGN PATENT DOCUMENTS

| | | |
|---|---|---|
| WO | WO-0064986 A1 | 11/2000 |
| WO | WO-2013180811 A1 | 12/2013 |

OTHER PUBLICATIONS

Zaragoza Dorwald, Side Reactions in Organic Synthesis, 2005, WILEY-VCH Verlag GmbH & Co. KGaA, Weinheim, Preface. p. IX. (Year: 2005).*
Kolmakov et al, European Journal of Organic Chemistry, A Versatile Route to Red-Emitting Carbopyronine Dyes for Optical Microscopy and Nanoscopy, 2010, pp. 3593-3610. (Year: 2010).*
Wallace et al (Cytometry Part A, Tracking Antigen-Driven Responses by Flow Cytometry: Monitoring Proliferation by Dye Dilution, 2008, 73A, pp. 1019-1034. (Year: 2008).*
PCT/US2015/030956, , "International Search Report and Written Opinion dated Jul. 16, 2015", dated Jul. 16, 2015, 12 Pages.
Wallace, P.K., et al., "Tracking Antigen-Driven Responses by Flow Cytometry: Monitoring Proliferation by Dye Dilution: Tracking Cell Proliferation", NIH Public Access Author Manuscript, vol. 73A, No. 11, Nov. 1, 2008, pp. 1019-1034.

* cited by examiner

*Primary Examiner* — Paul A Zucker

(57) ABSTRACT

Described herein are fluorescent compounds and methods and comprising these compounds. The compounds disclosed herein are carbopyronine reagents that fluoresce in the red portion of the UV/VIS spectrum and provide bright fluorescence intensity, uniform cell staining, and good retention within live cells as well as low toxicity toward cells.

8 Claims, 13 Drawing Sheets

Specification includes a Sequence Listing.

CARBOPYRONONE COMPOUNDS USEFUL AS DIAGNOSTIC ADJUVANTS

CROSS-REFERENCE TO RELATED APPLICATIONS

This application is a Divisional of U.S. Non Provisional patent application Ser. No. 15/304,800, filed Oct. 17, 2016, now U.S. Pat. No. 10,018,617 issued on Jul. 10, 2018, which is a 371 National Stage of PCT/US2015/030956, filed on May 15, 2015, which claims the benefit of U.S. Provisional Patent Application No. 61/994,555, filed May 16, 2014, which are herein incorporated by reference in their entireties.

FIELD

The present disclosure relates to carbopyronine fluorescent dye compounds, including reactive dye derivatives and dye-conjugates, and their uses as cell tracking reagents as well as in staining samples, labeling proteins, detecting ligands or other analytes.

SEQUENCE LISTING

The instant application contains a Sequence Listing which has been submitted electronically in ASCII format and is hereby incorporated by reference in its entirety. Said ASCII copy, created on May 8, 2015, is named LT00888PCT_SL.txt and is 468 bytes in size.

BACKGROUND

Methods for monitoring cell proliferation, differentiation, and function using flow cytometry have enabled investigation of complex biological phenomena, e.g., immune responses to antigen, which responses involve complex interactions among multiple cell types (see, Wallace et al., *Cytometry Part A* 73A: 1019-1034 (2008)). So called cell-tracking dyes have proven useful for qualitative and quantitative monitoring of cell division, both in vivo and in vitro (see, Hawkins et al., *Nat Protoc* 2:2057-2067 (2007); and Wallace et al., *Immunol Invest* 36:527-561, (2007)). These dyes, also referred to herein as cell-tracking reagents or cell-tracking compounds which term is inclusive of cell-tracing reagents and cell-tracing compounds, generate a fluorescent signal that, while relatively stable in non-dividing cells, progressively decreases with each round of cell division. Reduction in fluorescence intensity can be quantified by flow cytometry in conjunction with any of several different algorithms to estimate the extent of proliferation (in response to a particular stimulus) based on dye dilution (see, Wallace et al., *Cytometry Part A* 73A: 1019-1034 (2008)). A major advantage of using flow cytometry in conjunction with cell-tracking reagents to monitor the extent of cell division is that cells can also be stained for expression of other cell surface or intracellular markers to define lineage, functionality, activation state, cytokine expression, etc. (see, Bercovici et al., *J Immunol Methods* 276:5-17, (2003); Fazekas de St Groth et al., *Immunol Cell Biol* 77:530-538, (1999); and Tanaka et al., *Immunol Invest* 33:309-324, (2004)).

Carboxyfluorescein diacetate succinimidyl ester (CFDA-SE or, alternatively, CFSE) remains a popular, commercially available cell-tracking reagent, excitable with 488-nm laser light to give a bright green fluorescence. CFDA-SE has been widely used to monitor cell proliferation by flow cytometry in heterogeneous cell populations and stains cells with a bright homogeneous fluorescence, which is partitioned between daughter cells during each cell division.

Notwithstanding the current popularity of CFDA-SE, there remains a need for alternative fluorescent dyes, useful as cell-tracking reagents, with different spectral properties. Such reagents may be combined for simultaneous use with other currently-available cell analysis reagents, such as, for example, the 488 nm-excitable reagent Green Fluorescent Protein (GFP), or with the 405 nm-excitable violet-emitting dye PACIFIC BLUE (Thermo Fisher Scientific), thereby permitting researchers to study cell proliferation, differentiation, and/or function in otherwise indistinguishable cell populations in mixed cell cultures with multi-color applications using flow cytometry.

The development of carbopyronine-based cell-tracking reagents that fluoresce in the red portion of the UV/VIS spectrum to provide bright fluorescence intensity for long-term monitoring of cell proliferation, differentiation, migration, location, and/or function using flow cytometry and/or fluorescence microscopy has, heretofore, not been realized.

SUMMARY

Described herein are dye compounds, methods, and kits that may be used to stain samples, label proteins, detect ligands or other analytes, and for short- or long-term tracking of cell proliferation, differentiation, structure and/or function. The compounds disclosed herein are carbopyronine-based dye compounds that fluoresce in the red portion of the UV/VIS spectrum and provide bright fluorescence intensity, uniform cell staining, good retention within cells and have low toxicity toward cells. These compounds may be used in place of and/or in combination with other currently-available cell analysis reagents, such as, for example, the 488 nm-excitable Green Fluorescent Protein (GFP), to track and/or stain otherwise indistinguishable cell populations in mixed cell cultures via flow cytometry and/or fluorescence microscopy, respectively.

One illustrative embodiment provides a compound having structural formula (I):

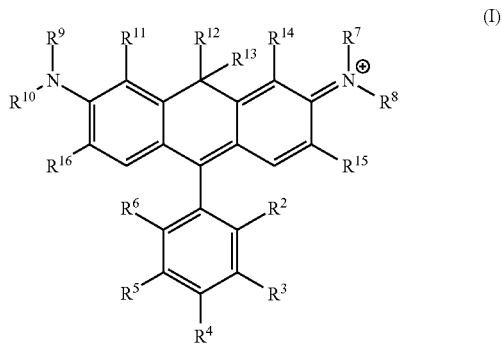

or a pharmaceutically acceptable salt thereof, wherein
$R^{12}$ and $R^{13}$ are each independently H, alkyl, substituted alkyl, or -L-$R_x$, or -L-$S_c$;
$R^2$, $R^3$, $R^4$, $R^5$, $R^6$, $R^7$, $R^8$, $R^9$, $R^{10}$, $R^{11}$, $R^{14}$, $R^{15}$, and $R^{16}$ are each independently H, halogen, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester) amino, (carboxyl ester) oxy, cyano, alkylcarboxylate, hydroxyl, nitro, sulfo, sulfoalkyl, substituted sulfoalkyl, sulfonyl, substituted sulfonyl, sulfonyloxy, thioacyl, thiol, alkylthiol, substituted alkylthiol, aryl, substituted aryl, heteroaryl, substituted heteroaryl, cycloalkyl, substituted cycloalkyl, heterocyclyl, substituted heterocyclyl, -L-$R_x$, or -L-$S_c$; or $R^7$ taken together with $R^{14}$ are part of an optionally substituted 5- or 6-membered ring;

$R^8$ taken together with $R^{15}$ are part of an optionally substituted 5- or 6-membered ring;

$R^9$ taken together with $R^{11}$ are part of an optionally substituted 5- or 6-membered ring;

$R^{10}$ taken together with $R^{16}$ are part of an optionally substituted 5- or 6-membered ring;

L is a linker;

$R_x$ is a reactive group; and $S_c$ is a conjugated substance.

In certain embodiments, $R^2$ is carboxyl, -L-$R_x$, or -L-$S_c$. In certain embodiments, $R^7$, $R^8$, $R^9$, and $R^{10}$ are each independently H, alkyl, substituted alkyl, or sulfoalkyl. In certain embodiments, $R^7$, $R^8$, $R^9$, and $R^{10}$ are each independently a $C_1$-$C_6$ alkyl, which can be the same or different. In certain embodiments, $R^7$, $R^8$, $R^9$, and $R^{10}$ are each methyl. In certain embodiments, $R^{12}$ and $R^{13}$ are each alkyl, preferably a $C_1$-$C_6$ alkyl. In certain embodiments, $R^{12}$ and $R^{13}$ are each methyl. In certain embodiments, $R^{11}$ and $R^{14}$ are each independently alkyl, substituted alkyl, sulfoalkyl, sulfo, -L-$R_x$, or -L-$S_c$. In certain embodiments, $R^{11}$ and $R^{14}$ are each independently a $C_1$-$C_6$ alkyl, a $C_1$-$C_6$ substituted alkyl, or sulfoalkyl, which can be the same or different. In certain embodiments, $R_x$ is succinimidyl ester (SE), sulfodichlorophenyl (SDP) ester, sulfotetrafluorophenyl (STP) ester, tetrafluorophenyl (TFP) ester, pentafluorophenyl (PFP) ester, nitrilotriacetic acid (NTA), aminodextran, and cyclooctyne-amine.

Another illustrative embodiment provides a compound having structural formula (II):

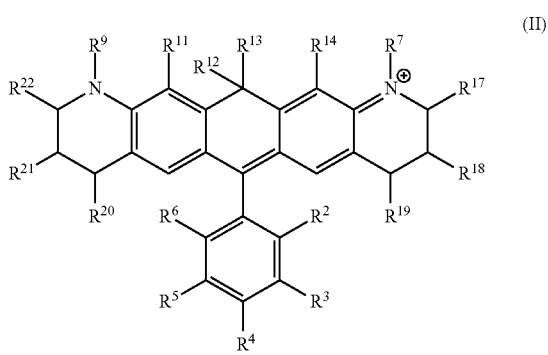

(II)

or a pharmaceutically acceptable salt thereof, wherein $R^{12}$ and $R^{13}$ are each independently H, alkyl, substituted alkyl, or -L-$R_x$, or -L-$S_c$;

$R^2$, $R^3$, $R^4$, $R^5$, $R^6$, $R^7$, $R^9$, $R^{11}$, $R^{14}$, $R^{17}$, $R^{18}$, $R^{19}$, $R^{20}$, $R^{21}$ and $R^{22}$ are each independently H, halogen, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester) amino, (carboxyl ester) oxy, cyano, alkylcarboxylate, hydroxyl, nitro, sulfo, sulfoalkyl, substituted sulfoalkyl, sulfonyl, substituted sulfonyl, sulfonyloxy, thioacyl, thiol, alkylthiol, substituted alkylthiol, aryl, substituted aryl, heteroaryl, substituted heteroaryl, cycloalkyl, substituted cycloalkyl, heterocyclyl, substituted heterocyclyl, -L-$R_x$, or -L-$S_c$;

L is a linker;

$R_x$ is a reactive group; and $S_c$ is a conjugated substance.

In certain embodiments, $R^{12}$ and $R^{13}$ are each alkyl, preferably a $C_1$-$C_6$ alkyl. In certain embodiments, $R^{12}$ and $R^{13}$ are each methyl. In certain embodiments, $R^2$ is carboxyl, -L-$R_x$, or -L-$S_c$. In certain embodiments, $R^3$, $R^4$, $R^5$ and $R^6$ are each independently H or halo. In certain embodiments, $R^3$, $R^4$, $R^5$ and $R^6$ are independently H, Cl, or F. In certain embodiments, $R^7$ and $R^9$ are each independently alkyl, substituted alkyl, sulfoalkyl, sulfo, -L-$R_x$, or -L-$S_c$. In certain embodiments, $R^7$ and $R^9$ are each independently methyl, -L-$R_x$, -L-$S_c$ or $(CH_2)_nSO_3^-$, wherein n is an integer between 1 and 6. In certain embodiments, n is 3. In certain embodiments, $R_x$ is succinimidyl ester (SE), sulfodichlorophenyl (SDP) ester, sulfotetrafluorophenyl (STP) ester, tetrafluorophenyl (TFP) ester, pentafluorophenyl (PFP) ester, nitrilotriacetic acid (NTA), aminodextran, and cyclooctyne-amine.

Another illustrative embodiment provides a compound having structural formula (III):

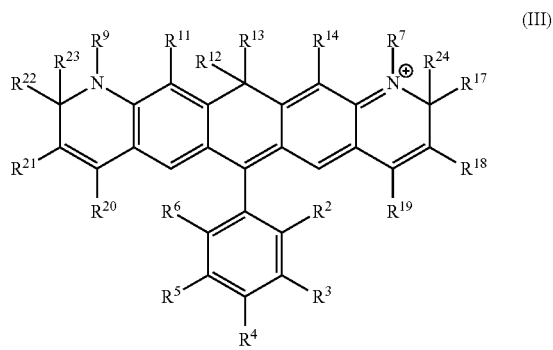

(III)

or a pharmaceutically acceptable salt thereof, wherein $R^{12}$ and $R^{13}$ are each independently H, alkyl, substituted alkyl, or -L-$R_x$, or -L-$S_c$;

$R^2$, $R^3$, $R^4$, $R^5$, $R^6$, $R^7$, $R^9$, $R^{11}$, $R^{14}$, $R^{17}$, $R^{18}$, $R^{19}$, $R^{20}$, $R^{21}$, $R^{22}$, $R^{23}$, and $R^{24}$ are each independently H, halogen, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester) amino, (carboxyl ester) oxy, cyano, alkylcarboxylate, hydroxyl, nitro, sulfo, sulfoalkyl, substituted sulfoalkyl, sulfonyl, substituted sulfonyl, sulfonyloxy, thioacyl, thiol, alkylthiol, substituted alkylthiol, aryl, substituted aryl, heteroaryl, substituted heteroaryl, cycloalkyl, substituted cycloalkyl, heterocyclyl, substituted heterocyclyl, -L-$R_x$, or -L-$S_c$;

L is a linker;

$R_x$ is a reactive group; and $S_c$ is a conjugated substance.

In certain embodiments, $R^{12}$ and $R^{13}$ are each alkyl, preferably a $C_1$-$C_6$ alkyl. In certain embodiments, $R^{12}$ and $R^{13}$ are each methyl. In certain embodiments, $R^2$ is carboxyl, -L-$R_x$, or -L-$S_c$. In certain embodiments, $R^7$, $R^9$, $R^{17}$, $R^{19}$, $R^{20}$, $R^{22}$, $R^{23}$ and $R^{24}$ are each independently alkyl, substituted alkyl, sulfoalkyl, sulfo, -L-$R_x$, or -L-$S_c$. In certain embodiments, $R^7$, $R^9$, $R^{17}$, $R^{22}$, $R^{23}$ and $R^{24}$ are each methyl. In certain embodiments, $R^{19}$ and $R^{20}$ are each independently $(CH_2)_nSO_3^-$, wherein n is an integer between 1 and 6. In certain embodiments, n is 1. In certain embodiments, $R_x$ is succinimidyl ester (SE), sulfodichlorophenyl (SDP) ester, sulfotetrafluorophenyl (STP) ester, tetrafluorophenyl (TFP) ester, pentafluorophenyl (PFP) ester, nitrilotriacetic acid (NTA), aminodextran, and cyclooctyne-amine.

Another illustrative embodiment provides a compound having structural formula (IV):

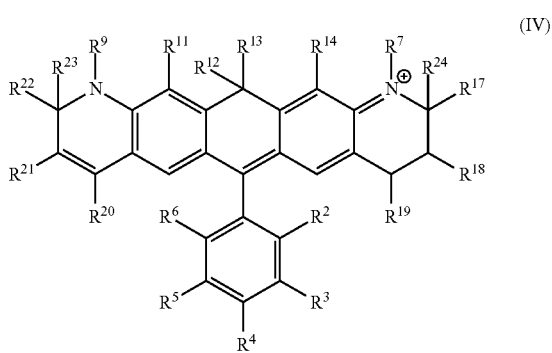

or a pharmaceutically acceptable salt thereof, wherein
$R^{12}$ and $R^{13}$ are each independently H, alkyl, substituted alkyl, or -L-$R_x$, or -L-$S_c$;
$R^2$, $R^3$, $R^4$, $R^5$, $R^6$, $R^7$, $R^9$, $R^{11}$, $R^{14}$, $R^{17}$, $R^{18}$, $R^{19}$, $R^{20}$, $R^{21}$, $R^{22}$, $R^{23}$, and $R^{24}$ are each independently H, halogen, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester) amino, (carboxyl ester) oxy, cyano, alkylcarboxylate, hydroxyl, nitro, sulfo, sulfoalkyl, substituted sulfoalkyl, sulfonyl, substituted sulfonyl, sulfonyloxy, thioacyl, thiol, alkylthiol, substituted alkylthiol, aryl, substituted aryl, heteroaryl, substituted heteroaryl, cycloalkyl, substituted cycloalkyl, heterocyclyl, substituted heterocyclyl, -L-$R_x$, or -L-$S_c$;
L is a linker;
$R_x$ is a reactive group; and
$S_c$ is a conjugated substance.

In certain embodiments, $R^9$, $R^{12}$, $R^{13}$, $R^{22}$ and $R^{23}$ are each alkyl, preferably a $C_1$-$C_6$ alkyl. In certain embodiments, $R^9$, $R^{12}$, $R^{13}$, $R^{22}$ and $R^{23}$ are each methyl. In certain embodiments, $R^3$, $R^4$, $R^5$ and $R^6$ are each independently H or halo. In certain embodiments, $R^3$ and $R^6$ are independently H, Cl, or F. In certain embodiments, $R^2$ is carboxyl. In certain embodiments, $R^7$, $R^9$ and $R^{20}$ are each independently alkyl, substituted alkyl, sulfoalkyl, sulfo, $(CH_2)_nSO_3^-$, wherein n is an integer between 1 and 6, -L-$R_x$, or -L-$S_c$. In certain embodiments, $R^7$ is -L-$R_x$ and $R^{20}$ is $(CH_2)_nSO_3^-$. In certain embodiments, n is 1. In certain embodiments, $R_x$ is succinimidyl ester (SE), sulfodichlorophenyl (SDP) ester, sulfotetrafluorophenyl (STP) ester, tetrafluorophenyl (TFP) ester, pentafluorophenyl (PFP) ester, nitrilotriacetic acid (NTA), aminodextran, and cyclooctyne-amine.

In certain embodiments, $R_x$ is selected from an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, an imido ester, an isocyanate, an isothiocyanate, a maleimide, a phosphoramidite, a photoactivatable group, a reactive platinum complex, a silyl halide, a sulfonyl halide, and a thiol. In certain embodiments the reactive group is selected from the group consisting of carboxylic acid, succinimidyl ester of a carboxylic acid, hydrazide, amine and a maleimide. The reactive group may be attached to any appropriate site on the reporter molecule or the aniline moiety. In certain embodiments, at least one member selected from $R^2$, $R^3$, $R^4$, $R^5$, $R^6$, $R^7$, $R^8$, $R^9$, $R^{10}$, $R^{12}$, $R^{13}$, $R^{19}$ and $R^{20}$ is a reactive group. In certain embodiments, at least one of $R^2$, $R^4$, $R^5$, $R^7$, $R^8$, $R^9$, $R^{10}$, $R^{12}$ and $R^{13}$ is a reactive group. In certain embodiments, at least one of $R^7$, $R^8$, $R^9$, $R^{10}$, $R^{12}$ and $R^{13}$ is a reactive group.

In certain embodiments, $S_c$ is selected from a carrier molecule and a solid support. In certain embodiments, $S_c$ is selected from an amino acid, a polymer of amino acids, a peptide, a protein, a neurotoxin, a phallotoxin, a cytokine, a toxin, a protease substrate, a protein kinase substrate, an enzyme, an antibody, an antibody fragment, a lectin, a glycoprotein, a histone, an albumin, a lipoprotein, avidin, streptavidin, protein A, protein G, a phycobiliprotein, a fluorescent protein, a hormone, a growth factor, a nucleic acid base, a nucleoside, a nucleotide, a nucleic acid polymer, a nucleotide analog, a nucleoside analog, a nucleoside triphosphate, a deoxynucleoside triphosphate, a dideoxynucleoside triphosphate, a hapten, a carbohydrate, a polysaccharide, a lipid, an ion-complexing moiety (such as a crown ether), a PEG group and an organic or inorganic polymer. In certain embodiments, at least one member selected from $R^2$, $R^3$, $R^4$, $R^5$, $R^6$, $R^7$, $R^8$, $R^9$, $R^{10}$, $R^{12}$, $R^{13}$, $R^{19}$ and $R^{20}$ is a conjugated substance. In certain embodiments, at least one of $R^2$, $R^4$, $R^5$, $R^7$, $R^8$, $R^9$, $R^{10}$, $R^{12}$ and $R^{13}$ is a conjugated substance. In certain embodiments, at least one of $R^7$, $R^8$, $R^9$, $R^{10}$, $R^{12}$ and $R^{13}$ is a conjugated substance. In certain embodiments, at least one of $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ is a PEG group.

In certain embodiments, compounds are provided selected from the group consisting of Compound 1, Compound 2, Compound 3, Compound 4, Compound 5, Compound 6, Compound 7, Compound 8, Compound 9, Compound 10, Compound 11, Compound 12, Compound 13, Compound 14, Compound 15, Compound 16, Compound 17, Compound 18, Compound 19, Compound 20, Compound 21, Compound 22, Compound 23, Compound 24, Compound 25 and amine-reactive forms thereof.

In certain embodiments, compositions are provided, the compositions comprising:
 a) one or more of the compounds provided herein; and
 b) a carrier.

In certain embodiments, compositions are provided, the compositions comprising:
 a) one or more of the compounds provided herein; and
 b) an analyte.

In certain embodiments, compositions for tracking cell proliferation, differentiation and/or function are provided, the compositions comprising:
 a) one or more of the compounds provided herein; and
 b) a carrier,
wherein the one or more of the compounds are present in an amount effective to track cell proliferation, differentiation, and/or function.

In certain embodiments, compositions for tracking cell proliferation, differentiation and/or function are provided, the compositions comprising:
(a) one or more of the compounds provided herein; and
(b) an analyte,
wherein the one or more of the compounds are present in an amount effective to track cell proliferation, differentiation, and/or function.

In certain embodiments, the analyte is a cell and the compound is located inside the cell. In certain embodiments, the compound is conjugated to a carrier molecule.

Another embodiment provides a kit for tracking cell proliferation, differentiation and/or function, the kit being compatible for use with, for example, flow cytometry and fluorescence microscopy, and comprising:
a) a compound of structural formula (I):

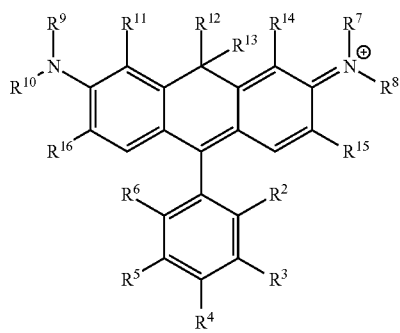

(I)

or a pharmaceutically acceptable salt thereof, wherein
$R^{12}$ and $R^{13}$ are each independently H, alkyl, substituted alkyl, or -L-$R_x$, or -L-$S_c$;
$R^2$, $R^3$, $R^4$, $R^5$, $R^6$, $R^7$, $R^8$, $R^9$, $R^{10}$, $R^{11}$, $R^{14}$, $R^{15}$, and $R^{16}$ are each independently H, halogen, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester) amino, (carboxyl ester) oxy, cyano, alkylcarboxylate, hydroxyl, nitro, sulfo, sulfoalkyl, substituted sulfoalkyl, sulfonyl, substituted sulfonyl, sulfonyloxy, thioacyl, thiol, alkylthiol, substituted alkylthiol, aryl, substituted aryl, heteroaryl, substituted heteroaryl, cycloalkyl, substituted cycloalkyl, heterocyclyl, substituted heterocyclyl, -L-$R_x$, or -L-$S_c$; or
$R^7$ taken together with $R^{14}$ are part of an optionally substituted 5- or 6-membered ring;
$R^8$ taken together with $R^{15}$ are part of an optionally substituted 5- or 6-membered ring;
$R^9$ taken together with $R^{11}$ are part of an optionally substituted 5- or 6-membered ring;
$R^{10}$ taken together with $R^{16}$ are part of an optionally substituted 5- or 6-membered ring;
L is a linker;
$R_x$ is a reactive group; and
$S_c$ is a conjugated substance;
b) an organic solvent; and
c) a desiccant.

In certain embodiments, $R^2$ is carboxyl, -L-$R_x$, or -L-$S_c$. In certain embodiments, $R^8$, $R^9$, and $R^{10}$ are each independently H, alkyl, substituted alkyl, or sulfoalkyl. In certain embodiments, $R^8$, $R^9$, and $R^{10}$ are each a $C_1$-$C_6$ alkyl, which can be the same or different. In certain embodiments, $R^8$, $R^9$, and $R^{10}$ are each methyl. In certain embodiments, $R^{12}$ and $R^{13}$ are each alkyl, preferably a $C_1$-$C_6$ alkyl. In certain embodiments, $R^{12}$ and $R^{13}$ are each methyl. In certain embodiments, $R^{11}$ and $R^{14}$ are each independently alkyl, substituted alkyl, sulfoalkyl, sulfo, -L-$R_x$, or -L-$S_c$. In certain embodiments, $R^{11}$ and $R^{14}$ are each independently a $C_1$-$C_6$ alkyl, a $C_1$-$C_6$ substituted alkyl, or sulfoalkyl, which can be the same or different. In certain embodiments, $R_x$ is succinimidyl ester (SE), sulfodichlorophenyl (SDP) ester, sulfotetrafluorophenyl (STP) ester, tetrafluorophenyl (TFP) ester, pentafluorophenyl (PFP) ester, nitrilotriacetic acid (NTA), aminodextran, and cyclooctyne-amine.

Another embodiment provides a kit for tracking cell proliferation, differentiation and/or function, the kit being compatible for use with, for example, flow cytometry and fluorescence microscopy, and comprising:
a) a compound of structural formula (II):

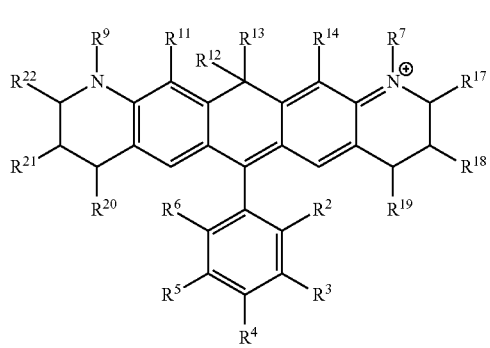

(II)

or a pharmaceutically acceptable salt thereof, wherein
$R^{12}$ and $R^{13}$ are each independently H, alkyl, substituted alkyl, or -L-$R_x$, or -L-$S_c$;
$R^2$, $R^3$, $R^4$, $R^5$, $R^6$, $R^7$, $R^9$, $R^{11}$, $R^{14}$, $R^{17}$, $R^{18}$, $R^{19}$, $R^{20}$, $R^{21}$ and $R^{22}$ are each independently H, halogen, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester) amino, (carboxyl ester) oxy, cyano, alkylcarboxylate, hydroxyl, nitro, sulfo, sulfoalkyl, substituted sulfoalkyl, sulfonyl, substituted sulfonyl, sulfonyloxy, thioacyl, thiol, alkylthiol, substituted alkylthiol, aryl, substituted aryl, heteroaryl, substituted heteroaryl, cycloalkyl, substituted cycloalkyl, heterocyclyl, substituted heterocyclyl, -L-$R_x$, or -L-$S_c$;
L is a linker;
$R_x$ is a reactive group; and
$S_c$ is a conjugated substance;
b) an organic solvent; and
c) a desiccant.

In certain embodiments, $R^{12}$ and $R^{13}$ are each alkyl, preferably a $C_1$-$C_6$ alkyl. In certain embodiments, $R^{12}$ and $R^{13}$ are each methyl. In certain embodiments, $R^2$ is carboxyl, -L-$R_x$, or -L-$S_c$. In certain embodiments, $R^3$, $R^4$, $R^5$ and $R^6$ are each independently H or halo. In certain embodiments, $R^3$, $R^4$, $R^5$ and $R^6$ are independently H, Cl, or F. In certain embodiments, $R^7$ and $R^9$ are each independently alkyl, substituted alkyl, sulfoalkyl, sulfo, -L-$R_x$, or -L-$S_c$. In certain embodiments, $R^7$ and $R^9$ are each independently methyl, -L-$R_x$, -L-$S_c$ or $(CH_2)_n SO_3^-$, wherein n is an integer between 1 and 6. In certain embodiments, n is 3. In certain embodiments, $R_x$ is succinimidyl ester (SE), sulfodichlorophenyl (SDP) ester, sulfotetrafluorophenyl (STP) ester, tetrafluorophenyl (TFP) ester, pentafluorophenyl (PFP) ester, nitrilotriacetic acid (NTA), aminodextran, and cyclooctyne-amine.

Another embodiment provides a kit for tracking cell proliferation, differentiation and/or function, the kit being compatible for use with, for example, flow cytometry and fluorescence microscopy, and comprising:

a) a compound of structural formula (III):

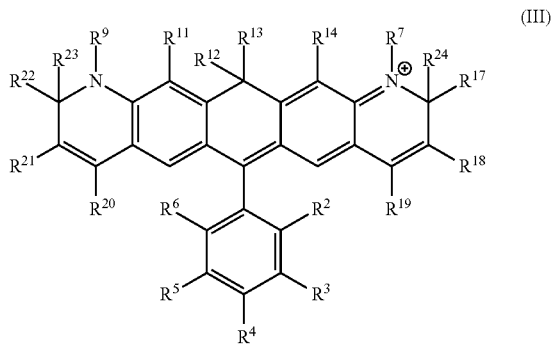

(III)

or a pharmaceutically acceptable salt thereof, wherein $R^{12}$ and $R^{13}$ are each independently H, alkyl, substituted alkyl, or -L-$R_x$, or -L-$S_c$;

$R^2$, $R^3$, $R^4$, $R^5$, $R^6$, $R^7$, $R^9$, $R^{11}$, $R^{14}$, $R^{17}$, $R^{18}$, $R^{19}$, $R^{20}$, $R^{21}$, $R^{22}$, $R^{23}$ and $R^{24}$ are each independently H, halogen, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester) amino, (carboxyl ester) oxy, cyano, alkylcarboxylate, hydroxyl, nitro, sulfo, sulfoalkyl, substituted sulfoalkyl, sulfonyl, substituted sulfonyl, sulfonyloxy, thioacyl, thiol, alkylthiol, substituted alkylthiol, aryl, substituted aryl, heteroaryl, substituted heteroaryl, cycloalkyl, substituted cycloalkyl, heterocyclyl, substituted heterocyclyl, -L-$R_x$, or -L-$S_c$;

L is a linker;

$R_x$ is a reactive group; and $S_c$ is a conjugated substance;

b) an organic solvent; and c) a desiccant.

In certain embodiments, $R^{12}$ and $R^{13}$ are each alkyl, preferably a $C_1$-$C_6$ alkyl. In certain embodiments, $R^{12}$ and $R^{13}$ are each methyl. In certain embodiments, $R^2$ is carboxyl, -L-$R_x$, or -L-$S_c$. In certain embodiments, $R^7$, $R^9$, $R^{17}$, $R^{19}$, $R^{20}$, $R^{22}$, $R^{23}$ and $R^{24}$ are each independently alkyl, substituted alkyl, sulfoalkyl, sulfo, -L-$R_x$, or -L-$S_c$. In certain embodiments, $R^7$, $R^9$, $R^{17}$, $R^{22}$, $R^{23}$ and $R^{24}$ are each methyl. In certain embodiments, $R^{19}$ and $R^{20}$ are each independently $(CH_2)_nSO_3^-$, wherein n is an integer between 1 and 6. In certain embodiments, n is 1. In certain embodiments, $R_x$ is succinimidyl ester (SE), sulfodichlorophenyl (SDP) ester, sulfotetrafluorophenyl (STP) ester, tetrafluorophenyl (TFP) ester, pentafluorophenyl (PFP) ester, nitrilotriacetic acid (NTA), aminodextran, and cyclooctyne-amine.

Another embodiment provides a kit for tracking cell proliferation, differentiation and/or function, the kit being compatible for use with, for example, flow cytometry and fluorescence microscopy, and comprising:

a) a compound of structural formula (IV):

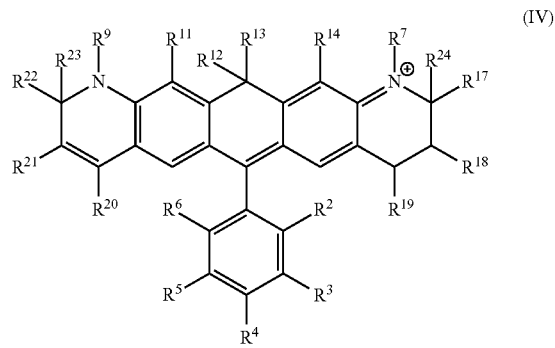

(IV)

or a pharmaceutically acceptable salt thereof, wherein $R^{12}$ and $R^{13}$ are each independently H, alkyl, substituted alkyl, or -L-$R_x$, or -L-$S_c$;

$R^2$, $R^3$, $R^4$, $R^5$, $R^6$, $R^7$, $R^9$, $R^{11}$, $R^{14}$, $R^{17}$, $R^{18}$, $R^{19}$, $R^{20}$, $R^{21}$, $R^{22}$, $R^{23}$ and $R^{24}$ are each independently H, halogen, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester) amino, (carboxyl ester) oxy, cyano, alkylcarboxylate, hydroxyl, nitro, sulfo, sulfoalkyl, substituted sulfoalkyl, sulfonyl, substituted sulfonyl, sulfonyloxy, thioacyl, thiol, alkylthiol, substituted alkylthiol, aryl, substituted aryl, heteroaryl, substituted heteroaryl, cycloalkyl, substituted cycloalkyl, heterocyclyl, substituted heterocyclyl, -L-$R_x$, or -L-$S_c$;

L is a linker;

$R_x$ is a reactive group; and $S_c$ is a conjugated substance;

b) an organic solvent; and c) a desiccant.

In certain embodiments, $R^9$, $R^{12}$, $R^{13}$, $R^{22}$ and $R^{23}$ are each alkyl, preferably a $C_1$-$C_6$ alkyl. In certain embodiments, $R^9$, $R^{12}$, $R^{13}$, $R^{22}$ and $R^{23}$ are each methyl. In certain embodiments, $R^3$, $R^4$, $R^5$ and $R^6$ are each independently H or halo. In certain embodiments, $R^3$ and $R^6$ are independently H, Cl, or F. In certain embodiments, $R^2$ is carboxyl. In certain embodiments, $R^7$, $R^9$ and $R^{20}$ are each independently alkyl, substituted alkyl, sulfoalkyl, sulfo, $(CH_2)_nSO_3^-$, wherein n is an integer between 1 and 6, -L-$R_x$, or -L-$S_c$. In certain embodiments, $R^7$ is -L-$R_x$ and $R^{20}$ is $(CH_2)_nSO_3^-$. In certain embodiments, n is 1. In certain embodiments, $R_x$ is succinimidyl ester (SE), sulfodichlorophenyl (SDP) ester, sulfotetrafluorophenyl (STP) ester, tetrafluorophenyl (TFP) ester, pentafluorophenyl (PFP) ester, nitrilotriacetic acid (NTA), aminodextran, and cyclooctyne-amine.

In certain embodiments, $R_x$ is selected from an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, an imido ester, an isocyanate, an isothiocyanate, a maleimide, a phosphoramidite, a photoactivatable group, a reactive platinum complex, a silyl halide, a sulfonyl halide, and a thiol. In certain embodiments the reactive group is selected from the group consisting of carboxylic acid, succinimidyl ester of a carboxylic acid, hydrazide, amine and a maleimide. The reactive group may be attached to any appropriate site on the reporter molecule or the aniline moiety. In certain embodiments, at least one member selected from $R^2$, $R^3$, $R^4$, $R^5$, $R^6$, $R^7$, $R^8$, $R^9$, $R^{10}$, $R^{12}$, $R^{13}$, $R^{19}$ and $R^{20}$ is a reactive group. In certain embodiments, at least one of $R^2$, $R^4$, $R^5$, $R^7$, $R^8$, $R^9$, $R^{10}$, $R^{12}$ and $R^{13}$ is a reactive group. In certain embodiments, at least one of $R^7$, $R^8$, $R^9$, $R^{10}$, $R^{12}$ and $R^{13}$ is a reactive group.

In certain embodiments, $S_c$ is selected from a carrier molecule and a solid support. In certain embodiments, $S_c$ is selected from an amino acid, a polymer of amino acids, a peptide, a protein, a neurotoxin, a phallotoxin, a cytokine, a toxin, a protease substrate, a protein kinase substrate, an enzyme, an antibody, an antibody fragment, a lectin, a glycoprotein, a histone, an albumin, a lipoprotein, avidin, streptavidin, protein A, protein G, a phycobiliprotein, a fluorescent protein, a hormone, a growth factor, a nucleic acid base, a nucleoside, a nucleotide, a nucleic acid polymer, a nucleotide analog, a nucleoside analog, a nucleoside triphosphate, a deoxynucleoside triphosphate, a dideoxynucleoside triphosphate, a hapten, a carbohydrate, a polysaccharide, a lipid, an ion-complexing moiety (such as a crown ether), a PEG group, and an organic or inorganic polymer. In certain embodiments, at least one member selected from $R^2$, $R^3$, $R^4$, $R^5$, $R^6$, $R^7$, $R^8$, $R^9$, $R^{10}$, $R^{12}$ and $R^{13}$ is a conjugated substance. In certain embodiments, at least one of $R^2$, $R^4$, $R^5$, $R^7$, $R^8$, $R^9$, $R^{10}$, $R^{12}$, $R^{13}$, $R^{19}$ and $R^{20}$ is a conjugated substance. In certain embodiments, at least one of $R^7$, $R^8$, $R^9$, $R^{10}$, $R^{12}$ and $R^{13}$ is a conjugated substance. In certain embodiments, at least one of $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ is a PEG group.

In certain embodiments, the compounds used in the kits provided herein are selected from the group consisting of Compound 1, Compound 2, Compound 3, Compound 4, Compound 5, Compound 6, Compound 7, Compound 8, Compound 9, Compound 10, Compound 11, Compound 12, Compound 13, Compound 14, Compound 15, Compound 16, Compound 17, Compound 18, Compound 19, Compound 20, Compound 21, Compound 22, Compound 23, Compound 24, Compound 25 and amine-reactive forms thereof.

In another illustrative embodiment of the kit, $R_x$ is a succinimidyl ester. In another illustrative embodiment, the organic solvent is DMSO. In another illustrative embodiment, the kit further comprises instructions for tracking cell proliferation, differentiation, and/or function according to a method disclosed herein.

In certain embodiments, kits for tracking cell proliferation, differentiation and/or function are provided, the kit comprising:
 (a) one or more of the compounds described herein;
 (b) one or more containers; and optionally
 (c) instructions for tracking cell proliferation, differentiation, and/or function according to a method disclosed herein.

In certain embodiments, kits are provided, the kit comprising:
 (a) one or more of the compounds described herein;
 (b) one or more containers; and optionally
 (c) instructions for using according to a method disclosed herein.

In certain embodiments, kits for tracking cell proliferation, differentiation and/or function are provided, the kit comprising:
 (a) one or more of the compositions described herein;
 b) an organic solvent; and
 c) a desiccant.

In certain embodiments, kits for tracking cell proliferation, differentiation and/or function are provided, the kit comprising:
 (a) one or more of the compositions described herein;
 (b) one or more containers; and optionally
 (c) instructions for tracking cell proliferation, differentiation, and/or function according to a method disclosed herein.

Another embodiment provides a method for tracking cell proliferation, differentiation, and/or function, the method being compatible for use with, for example, flow cytometry and fluorescence microscopy, and comprising:
a) incubating a mixture of cells and a compound of structural formula (I):

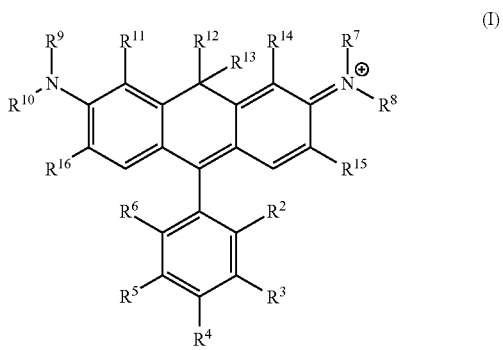

or a pharmaceutically acceptable salt thereof, wherein
$R^{12}$ and $R^{13}$ are each independently H, alkyl, substituted alkyl, or -L-$R_x$, or -L-$S_c$;
$R^2$, $R^3$, $R^4$, $R^5$, $R^6$, $R^7$, $R^8$, $R^9$, $R^{10}$, $R^{11}$, $R^{14}$, $R^{15}$, and $R^{16}$ are each independently H, halogen, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester) amino, (carboxyl ester) oxy, cyano, alkylcarboxylate, hydroxyl, nitro, sulfo, sulfoalkyl, substituted sulfoalkyl, sulfonyl, substituted sulfonyl, sulfonyloxy, thioacyl, thiol, alkylthiol, substituted alkylthiol, aryl, substituted aryl, heteroaryl, substituted heteroaryl, cycloalkyl, substituted cycloalkyl, heterocyclyl, substituted heterocyclyl, -L-$R_x$, or -L-$S_c$; or $R^7$ taken together with $R^{14}$ are part of an optionally substituted 5- or 6-membered ring;
$R^8$ taken together with $R^{15}$ are part of an optionally substituted 5- or 6-membered ring;
$R^9$ taken together with $R^{11}$ are part of an optionally substituted 5- or 6-membered ring;
$R^{10}$ taken together with $R^{16}$ are part of an optionally substituted 5- or 6-membered ring;
L is a linker;
$R_x$ is a reactive group; and
$S_c$ is a conjugated substance;
b) providing a stimulus to the mixture to elicit a fluorescent signal; and
c) analyzing the stimulated mixture.

In certain embodiments, $R^2$ is carboxyl, -L-$R_x$, or -L-$S_c$. In certain embodiments, $R^7$, $R^8$, $R^9$, and $R^{10}$ are each independently H, alkyl, substituted alkyl, or sulfoalkyl. In certain embodiments, $R^7$, $R^8$, $R^9$, and $R^{10}$ are each independently a $C_1$-$C_6$ alkyl, which can be the same or different. In certain embodiments, $R^7$, $R^8$, $R^9$, and $R^{10}$ are each methyl. In certain embodiments, $R^{12}$ and $R^{13}$ are each alkyl, preferably a $C_1$-$C_6$ alkyl. In certain embodiments, $R^{12}$ and $R^{13}$ are each methyl. In certain embodiments, $R^{11}$ and $R^{14}$ are each independently alkyl, substituted alkyl, sulfoalkyl, sulfo, -L-$R_x$, or -L-$S_c$. In certain embodiments, $R^{11}$ and $R^{14}$ are each independently a $C_1$-$C_6$ alkyl, a $C_1$-$C_6$ substituted alkyl, or sulfoalkyl, which can be the same or different. In certain embodiments, $R_x$ is succinimidyl ester (SE), sulfodichlorophenyl (SDP) ester, sulfotetrafluorophenyl (STP) ester, tetrafluorophenyl (TFP) ester, pentafluorophenyl (PFP) ester, nitrilotriacetic acid (NTA), aminodextran, and cyclooctyne-amine.

Another embodiment provides a method for tracking cell proliferation, differentiation, and/or function, the method being compatible for use with, for example, flow cytometry and fluorescence microscopy, and comprising:

a) incubating a mixture of cells and a compound of structural formula (II):

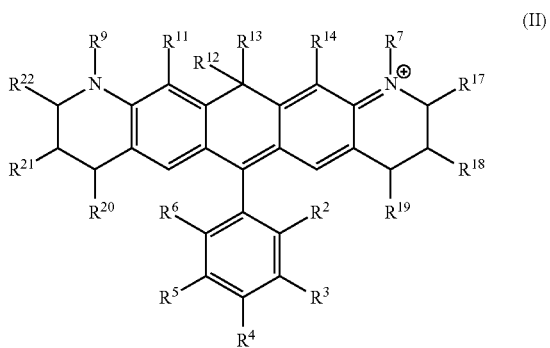

(II)

or a pharmaceutically acceptable salt thereof, wherein
$R^{12}$ and $R^{13}$ are each independently H, alkyl, substituted alkyl, -L-$R_x$, or -L-$S_c$;
$R^2$, $R^3$, $R^4$, $R^5$, $R^6$, $R^7$, $R^9$, $R^{11}$, $R^{14}$, $R^{17}$, $R^{18}$, $R^{19}$, $R^{20}$, $R^{21}$ and $R^{22}$ are each independently H, halogen, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester) amino, (carboxyl ester) oxy, cyano, alkylcarboxylate, hydroxyl, nitro, sulfo, sulfoalkyl, substituted sulfoalkyl, sulfonyl, substituted sulfonyl, sulfonyloxy, thioacyl, thiol, alkylthiol, substituted alkylthiol, aryl, substituted aryl, heteroaryl, substituted heteroaryl, cycloalkyl, substituted cycloalkyl, heterocyclyl, substituted heterocyclyl, -L-$R_x$, or -L-$S_c$;
L is a linker;
$R_x$ is a reactive group; and
$S_c$ is a conjugated substance;
b) providing a stimulus to the mixture to elicit a fluorescent signal; and
c) analyzing the stimulated mixture.

In certain embodiments, $R^{12}$ and $R^{13}$ are each alkyl, preferably a $C_1$-$C_6$ alkyl. In certain embodiments, $R^{12}$ and $R^{13}$ are each methyl. In certain embodiments, $R^2$ is carboxyl, -L-$R_x$, or -L-$S_c$. In certain embodiments, $R^3$, $R^4$, $R^5$ and $R^6$ are each independently H or halo. In certain embodiments, $R^3$, $R^4$, $R^5$ and $R^6$ are independently H, Cl, or F. In certain embodiments, $R^7$ and $R^9$ are each independently alkyl, substituted alkyl, sulfoalkyl, sulfo, -L-$R_x$, or -L-$S_c$. In certain embodiments, $R^7$ and $R^9$ are each independently methyl, -L-$R_x$, -L-$S_c$ or $(CH_2)_nSO_3^-$, wherein n is an integer between 1 and 6. In certain embodiments, n is 3. In certain embodiments, $R_x$ is succinimidyl ester (SE), sulfodichlorophenyl (SDP) ester, sulfotetrafluorophenyl (STP) ester, tetrafluorophenyl (TFP) ester, pentafluorophenyl (PFP) ester, nitrilotriacetic acid (NTA), aminodextran, and cyclooctyne-amine.

Another embodiment provides a method for tracking cell proliferation, differentiation, and/or function, the method being compatible for use with, for example, flow cytometry and fluorescence microscopy, and comprising:

a) incubating a mixture of cells and a compound of structural formula (III):

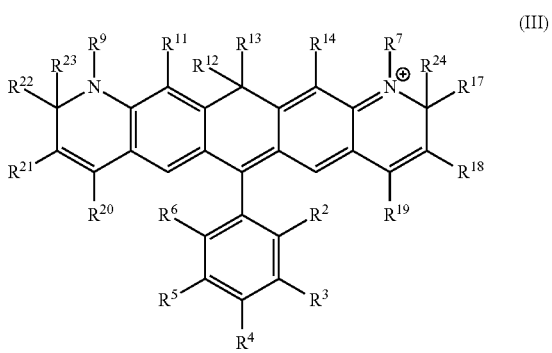

(III)

or a pharmaceutically acceptable salt thereof, wherein
$R^{12}$ and $R^{13}$ are each independently H, alkyl, substituted alkyl, or -L-$R_x$, or -L-$S_c$;
$R^2$, $R^3$, $R^4$, $R^5$, $R^6$, $R^7$, $R^9$, $R^{11}$, $R^{14}$, $R^{17}$, $R^{18}$, $R^{19}$, $R^{20}$, $R^{21}$, $R^{22}$, $R^{23}$ and $R^{24}$ are each independently H, halogen, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester) amino, (carboxyl ester) oxy, cyano, alkylcarboxylate, hydroxyl, nitro, sulfo, sulfoalkyl, substituted sulfoalkyl, sulfonyl, substituted sulfonyl, sulfonyloxy, thioacyl, thiol, alkylthiol, substituted alkylthiol, aryl, substituted aryl, heteroaryl, substituted heteroaryl, cycloalkyl, substituted cycloalkyl, heterocyclyl, substituted heterocyclyl, -L-$R_x$, or -L-$S_c$;
L is a linker;
$R_x$ is a reactive group; and
$S_c$ is a conjugated substance;
b) providing a stimulus to the mixture to elicit a fluorescent signal; and
c) analyzing the stimulated mixture.

In certain embodiments, $R^{12}$ and $R^{13}$ are each alkyl, preferably a $C_1$-$C_6$ alkyl. In certain embodiments, $R^{12}$ and $R^{13}$ are each methyl. In certain embodiments, $R^2$ is carboxyl, -L-$R_x$, or -L-$S_c$. In certain embodiments, $R^7$, $R^9$, $R^{17}$, $R^{19}$, $R^{20}$, $R^{22}$, $R^{23}$ and $R^{24}$ are each independently alkyl, substituted alkyl, sulfoalkyl, sulfo, -L-$R_x$, or -L-$S_c$. In certain embodiments, $R^7$, $R^9$, $R^{17}$, $R^{22}$, $R^{23}$ and $R^{24}$ are each methyl. In certain embodiments, $R^{19}$ and $R^{20}$ are each independently $(CH_2)_nSO_3^-$, wherein n is an integer between 1 and 6. In certain embodiments, n is 1. In certain embodiments, $R_x$ is succinimidyl ester (SE), sulfodichlorophenyl (SDP) ester, sulfotetrafluorophenyl (STP) ester, tetrafluorophenyl (TFP) ester, pentafluorophenyl (PFP) ester, nitrilotriacetic acid (NTA), aminodextran, and cyclooctyne-amine.

Another embodiment provides a method for tracking cell proliferation, differentiation, and/or function, the method being compatible for use with, for example, flow cytometry and fluorescence microscopy, and comprising:

a) incubating a mixture of cells and a compound of structural formula (IV):

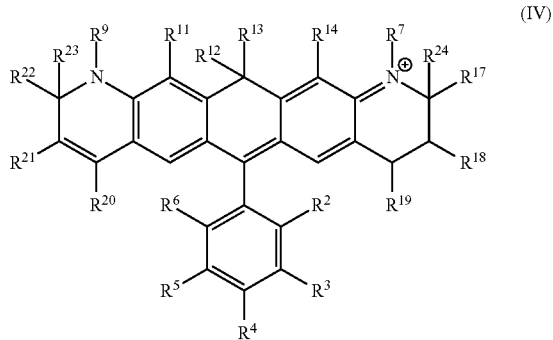

or a pharmaceutically acceptable salt thereof, wherein $R^{12}$ and $R^{13}$ are each independently H, alkyl, substituted alkyl, or -L-$R_x$, or -L-$S_c$;

$R^2$, $R^3$, $R^4$, $R^5$, $R^6$, $R^7$, $R^9$, $R^{11}$, $R^{14}$, $R^{17}$, $R^{18}$, $R^{19}$, $R^{20}$, $R^{21}$, $R^{22}$, $R^{23}$ and $R^{24}$ are each independently H, halogen, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester) amino, (carboxyl ester) oxy, cyano, alkylcarboxylate, hydroxyl, nitro, sulfo, sulfoalkyl, substituted sulfoalkyl, sulfonyl, substituted sulfonyl, sulfonyloxy, thioacyl, thiol, alkylthiol, substituted alkylthiol, aryl, substituted aryl, heteroaryl, substituted heteroaryl, cycloalkyl, substituted cycloalkyl, heterocyclyl, substituted heterocyclyl, -L-$R_x$, or -L-$S_c$;

L is a linker;

$R_x$ is a reactive group; and $S_c$ is a conjugated substance;

b) providing a stimulus to the mixture to elicit a fluorescent signal; and c) analyzing the stimulated mixture.

In certain embodiments, $R^9$, $R^{12}$, $R^{13}$, $R^{22}$ and $R^{23}$ are each alkyl, preferably a $C_1$-$C_6$ alkyl. In certain embodiments, $R^9$, $R^{12}$, $R^{13}$, $R^{22}$ and $R^{23}$ are each methyl. In certain embodiments, $R^3$, $R^4$, $R^5$ and $R^6$ are each independently H or halo. In certain embodiments, $R^3$ and $R^6$ are independently H, Cl, or F. In certain embodiments, $R^2$ is carboxyl. In certain embodiments, $R^7$, $R^9$ and $R^{20}$ are each independently alkyl, substituted alkyl, sulfoalkyl, sulfo, $(CH_2)_nSO_3^-$, wherein n is an integer between 1 and 6, -L-$R_x$, or -L-$S_c$. In certain embodiments, $R^7$ is -L-$R_x$ and $R^{20}$ is $(CH_2)_nSO_3^-$. In certain embodiments, n is 1. In certain embodiments, $R_x$ is succinimidyl ester (SE), sulfodichlorophenyl (SDP) ester, sulfotetrafluorophenyl (STP) ester, tetrafluorophenyl (TFP) ester, pentafluorophenyl (PFP) ester, nitrilotriacetic acid (NTA), aminodextran, and cyclooctyne-amine.

In certain embodiments, $R_x$ is selected from an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, an imido ester, an isocyanate, an isothiocyanate, a maleimide, a phosphoramidite, a photoactivatable group, a reactive platinum complex, a silyl halide, a sulfonyl halide, and a thiol. In certain embodiments the reactive group is selected from the group consisting of carboxylic acid, succinimidyl ester of a carboxylic acid, hydrazide, amine and a maleimide. The reactive group may be attached to any appropriate site on the reporter molecule or the aniline moiety. In certain embodiments, at least one member selected from $R^2$, $R^3$, $R^4$, $R^5$, $R^6$, $R^7$, $R^8$, $R^9$, $R^{10}$, $R^{12}$, $R^{13}$, $R^{19}$ and $R^{20}$ is a reactive group. In certain embodiments, at least one of $R^2$, $R^4$, $R^5$, $R^7$, $R^8$, $R^9$, $R^{10}$, $R^{12}$ and $R^{13}$ is a reactive group. In certain embodiments, at least one of $R^7$, $R^8$, $R^9$, $R^{10}$, $R^{12}$ and $R^{13}$ is a reactive group.

In certain embodiments, $S_c$ is selected from a carrier molecule and a solid support. In certain embodiments, $S_c$ is selected from an amino acid, a polymer of amino acids, a peptide, a protein, a neurotoxin, a phallotoxin, a cytokine, a toxin, a protease substrate, a protein kinase substrate, an enzyme, an antibody, an antibody fragment, a lectin, a glycoprotein, a histone, an albumin, a lipoprotein, avidin, streptavidin, protein A, protein G, a phycobiliprotein, a fluorescent protein, a hormone, a growth factor, a nucleic acid base, a nucleoside, a nucleotide, a nucleic acid polymer, a nucleotide analog, a nucleoside analog, a nucleoside triphosphate, a deoxynucleoside triphosphate, a dideoxynucleoside triphosphate, a hapten, a carbohydrate, a polysaccharide, a lipid, an ion-complexing moiety (such as a crown ether), a PEG group, and an organic or inorganic polymer. In certain embodiments, at least one member selected from $R^2$, $R^3$, $R^4$, $R^5$, $R^6$, $R^7$, $R^8$, $R^9$, $R^{10}$, $R^{12}$, $R^{13}$, $R^{19}$ and $R^{20}$ is a conjugated substance. In certain embodiments, at least one of $R^2$, $R^4$, $R^5$, $R^7$, $R^8$, $R^9$, $R^{10}$, $R^{12}$ and $R^{13}$ is a conjugated substance. In certain embodiments, at least one of $R^7$, $R^8$, $R^9$, $R^{10}$, $R^{12}$ and $R^{13}$ is a conjugated substance. In certain embodiments, at least one of $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ is a PEG group.

In certain embodiments, the compounds used in the methods provided herein are selected from the group consisting of Compound 1, Compound 2, Compound 3, Compound 4, Compound 5, Compound 6, Compound 7, Compound 8, Compound 9, Compound 10, Compound 11, Compound 12, Compound 13, Compound 14, Compound 15, Compound 16, Compound 17, Compound 18, Compound 19, Compound 20, Compound 21, Compound 22, Compound 23, Compound 24, Compound 25 and amine-reactive forms thereof.

In one illustrative embodiment, the method includes a second compound excitable at a different wavelength as the first compound. In another illustrative embodiment, the method includes a second compound where the second compound includes, for example, GFP or PACIFIC BLUE (Thermo Fisher Scientific).

In another illustrative embodiment of the method, step a) is conducted for approximately 20 minutes. In another illustrative embodiment, step b) and step c) are carried out concurrently. In another illustrative embodiment, step b) and step c) involve flow cytometry.

The present disclosure also provides methods for determining cell health and/or viability using one or more of the compounds provided herein.

The present disclosure also provides methods for detecting an analyte in a sample using one or more of the compounds provided herein.

Another illustrative embodiment provides a process for preparing a conjugated compound of structural formula (I), (II), (III) or (IV), the process comprising:

reacting compound of structural formula (I), (II), (III) or (IV) with a substance to be conjugated thereto, thereby resulting in a conjugated substance $S_c$.

In certain embodiments, the compound of structural formula (I), (II), (III) or (IV) is conjugated to a carrier molecule or solid support. In certain embodiments, the compound of structural formula (I), (II), (III) or (IV) is conjugated to molecule selected from an amino acid, a polymer of amino acids, a peptide, a protein, a neurotoxin, a phallotoxin, a cytokine, a toxin, a protease substrate, a protein kinase substrate, an enzyme, an antibody, an antibody fragment, a lectin, a glycoprotein, a histone, an albumin, a lipoprotein, avidin, streptavidin, protein A, protein G, a phycobiliprotein, a fluorescent protein, a hormone, a growth factor, a nucleic acid base, a nucleoside, a nucleotide, a nucleic acid polymer, a nucleotide analog, a nucleoside analog, a nucleoside triphosphate, a deoxynucleoside triphosphate, a dideoxynucleoside triphosphate, a hapten, a carbohydrate, a polysaccharide, a lipid, an ion-complexing moiety (such as a crown ether), a PEG group, and an organic or inorganic polymer.

Other illustrative aspects, features and advantages of the present disclosure will become apparent from the following detailed description. It should be understood, however, that the detailed description and the specific examples that follow, while indicating preferred embodiments are given by way of illustration only. It is expected that various changes and modifications within the spirit and scope of the present disclosure will become apparent to those skilled in the art.

DETAILED DESCRIPTION

Figure 1A:
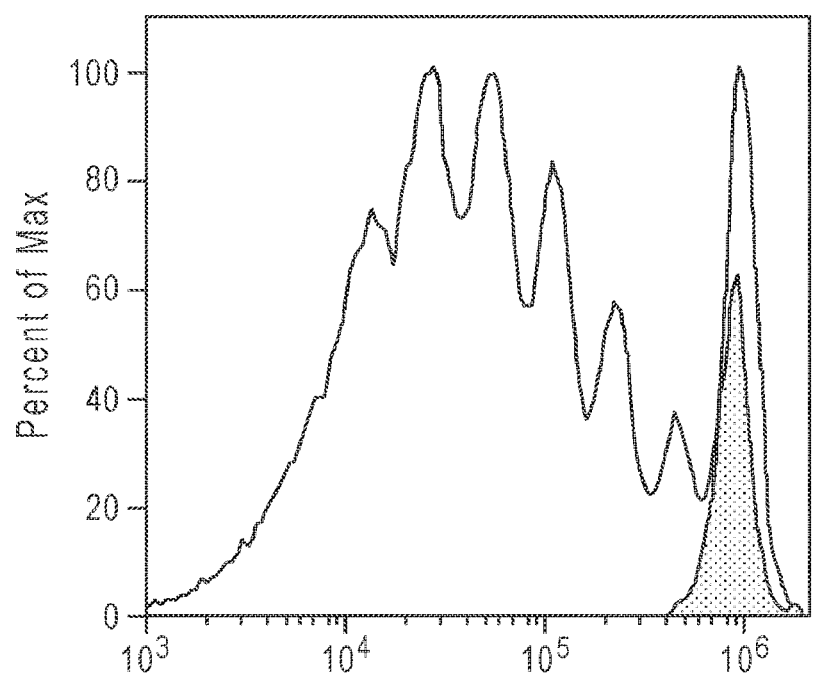
FIGS. 1A and 1B: Comparison of cell tracing ability of Compound 2 (FIG. 1A) and CELLTRACE Far Red DDAO (FIG. 1B), demonstrating that Compound 2 is able to trace seven generations of cells (see, Example 2).

The present disclosure provides compounds, methods, and kits for short- and long-term tracking of cell proliferation, differentiation, structure and/or function, as well as for staining samples, labeling proteins, detecting ligands and other analytes. The compounds of the present disclosure are dye compounds that fluoresce in the red portion of the UV/VIS spectrum and provide bright fluorescence intensity, uniform cell staining, good retention within cells and have low toxicity toward cells. The compounds disclosed herein are carbopyronine-based dye compounds, including reactive dye compound derivatives and dye-conjugates. These compounds may be used in place of and/or in combination with other currently-available cell analysis reagents, such as, for example, the 488 nm-excitable reagents IgG antibodies conjugated with fluorescein (FAM) and/or Green Fluorescent Protein (GFP) to track and/or stain otherwise indistinguishable cell populations in mixed cell cultures via flow cytometry and/or fluorescence microscopy, respectively. The present disclosure also includes processes for preparing and using the compounds described herein in the disclosed methods and kits provided herein.

Definitions

To more clearly and concisely describe and point out the subject matter of the present disclosure, the following definitions are provided for specific terms, which are used in the following description and appended claims. Throughout the specification, exemplification of specific terms should be considered as non-limiting examples.

Before describing the present teachings in detail, it is to be understood that the disclosure is not limited to specific compositions or process steps, as such may vary. It should be noted that, as used in this specification and the appended claims, the singular form "a", "an" and "the" include plural references unless the context clearly dictates otherwise. Thus, for example, reference to "a compound" includes a plurality of compounds and reference to "a cell" includes a plurality of cells and the like. The phrase "and/or" denotes a shorthand way of indicating that the specific combination is contemplated in combination and separately, in the alternative. For illustration purposes, but not as a limitation, "X and/or Y" can mean "X" or "Y" or "X" and "Y".

It will be appreciated that there is an implied "about" prior to the temperatures, concentrations, times, etc. discussed in the present disclosure, such that slight and insubstantial deviations are within the scope of the present teachings herein. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the teachings.

Unless specifically noted in the above specification, embodiments in the specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims).

The term "or combinations thereof" as used herein refers to all permutations and combinations of the listed terms preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

The section headings used herein are for organizational purposes only and are not to be construed as limiting the desired subject matter in any way. All literature cited in the specification, including but not limited to, patents, patent applications, articles, books and treatises are expressly incorporated by reference in their entirety for any purpose. In the event that any of the incorporated literature contradicts any term defined in this specification, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

A dashed line projecting from a substituent, such as:

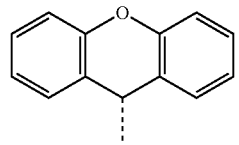

indicates the point of attachment to the base molecule. For a fused ring, dashed lines indicate portions of the base molecule where the fused ring is attached, such as:

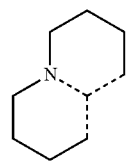

wherein the full molecule could have the structure:

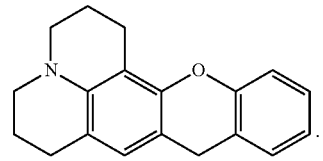 [SMILES: c1ccc2c(c1)Cc1cc3c4c(c1O2)CCCN4CCC3]

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

It is understood that in all substituted groups defined herein, polymers arrived at by defining substituents with further substituents to themselves (e.g., substituted aryl having a substituted aryl group as a substituent which is itself substituted with a substituted aryl group, which is further substituted by a substituted aryl group etc.) are not intended for inclusion herein. In such cases, the maximum number of such substitutions is three. For example, serial substitutions of substituted aryl groups with two other substituted aryl groups are limited to -substituted aryl-(substituted aryl)-substituted aryl.

Similarly, it is understood that the definitions provided herein are not intended to include impermissible substitution patterns (e.g., methyl substituted with 5 fluoro groups). Such impermissible substitution patterns are well known to the skilled artisan.

The compounds disclosed herein may exist in unsolvated forms as well as solvated forms, including hydrated forms. These compounds may exist in multiple crystalline or amorphous forms. In general, all physical forms are equivalent for the uses described herein and are intended to be within the scope of the present disclosure. The compounds disclosed herein may possess asymmetric carbon atoms (i.e., chiral centers) or double bonds; the racemates, diastereomers, geometric isomers and individual isomers of the compounds described herein are within the scope of the present disclosure. The compounds described herein may be prepared as a single isomer or as a mixture of isomers.

Where substituent groups are specified by their conventional chemical formulae and are written from left to right, they equally encompass the chemically identical substituents, which would result from writing the structure from right to left, e.g., —CH₂O— is intended to also recite —OCH₂—.

It will be understood that the chemical structures that are used to define the compounds disclosed herein are each representations of one of the possible resonance structures by which each given structure can be represented. Further, it will be understood that by definition, resonance structures are merely a graphical representation used by those of skill in the art to represent electron delocalization, and that the present disclosure is not limited in any way by showing one particular resonance structure for any given structure.

Where a disclosed compound includes a conjugated ring system, resonance stabilization may permit a formal electronic charge to be distributed over the entire molecule. While a particular charge may be depicted as localized on a particular ring system, or a particular heteroatom, it is commonly understood that a comparable resonance structure can be drawn in which the charge may be formally localized on an alternative portion of the compound.

"Alkyl" refers to monovalent saturated aliphatic hydrocarbyl groups having from 1 to 10 carbon atoms and preferably 1 to 6 carbon atoms, e.g. 1, 2, 3, 4, 5 or 6 carbon atoms. This term includes, by way of example, linear and branched hydrocarbyl groups such as methyl (CH₃—), ethyl (CH₃CH₂—), n-propyl (CH₃CH₂CH₂—), isopropyl ((CH₃)₂CH—), n-butyl (CH₃CH₂CH₂CH₂—), isobutyl ((CH₃)₂CHCH₂—), sec-butyl ((CH₃)(CH₃CH₂)CH—), t-butyl ((CH₃)₃C—), n-pentyl (CH₃CH₂CH₂CH₂CH₂—), and neopentyl ((CH₃)₃CCH₂—).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxylalkyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, sulfo, substituted sulfonyl, sulfonyloxy, thioacyl, thiol, alkylthio, and substituted alkylthio, wherein said substituents are defined herein. Particular substituted alkyl groups comprise a reactive group for direct or indirect linking to a carrier molecule or solid support, for example, but not limited to, alkyl substituted by carboxyl or a carboxyl ester (e.g. an activated ester such as an N-hydroxysuccinimide ester) and alkyl substituted by aminocarbonyl —CONHR where R is an organic moiety as defined below with reference to the term "aminocarbonyl", e.g. a $C_1$-$C_{10}$ (e.g. $C_1$-$C_6$) alkyl terminally substituted by a reactive group ($R_x$) including, but not limited to, carboxyl, carboxylester, maleimide, succinimidyl ester (SE), sulfodichlorophenyl (SDP) ester, sulfotetrafluorophenyl (STP) ester, tetrafluorophenyl (TFP) ester, pentafluorophenyl (PFP) ester, nitrilotriacetic acid (NTA), aminodextran, and cyclooctyne-amine.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl), wherein substituted alkyl is defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, sulfo, substituted sulfonyl, sulfonyloxy, thioacyl, thiol, alkylthio, and substituted alkylthio, wherein said substituents are defined herein.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy" refers to the group —O-(substituted heteroaryl).

"Alkenyl" refers to alkenyl groups having from 2 to 6 carbon atoms and preferably 2 to 4 carbon atoms and having at least 1 and preferably from 1 to 2 sites of alkenyl unsaturation. Such groups are exemplified, for example, by vinyl, allyl, but-3-en-1-yl, and propenyl.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, sulfo, substituted sulfonyl, sulfonyloxy, thioacyl, thiol, alkylthio, and substituted alkylthio, wherein said substituents are defined herein and with the proviso that any hydroxy substitution is not attached to a vinyl (unsaturated) carbon atom.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Acyl includes the "acetyl" group $CH_3C(O)$—.

"Acylamino" refers to the groups —NRC(O)alkyl, —NRC(O)substituted alkyl, —NRC(O) cycloalkyl, —NRC(O)substituted cycloalkyl, —NRC(O)cycloalkenyl, —NRC(O)substituted cycloalkenyl, —NRC(O)alkenyl, —NRC(O) substituted alkenyl, —NRC(O)alkynyl, —NRC(O) substituted alkynyl, —NRC(O)aryl, —NRC(O) substituted aryl, —NRC(O)heteroaryl, —NRC(O) substituted heteroaryl, —NRC(O)heterocyclic, and —NRC(O)substituted heterocyclic, wherein R is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group —$NH_2$.

"Substituted amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —$SO_2$-alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-cycloalkenyl, —$SO_2$-substituted cylcoalkenyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic and wherein R' and R" are optionally joined, together with the nitrogen bound thereto to form a heterocyclic or substituted heterocyclic group, provided that R' and R" are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When R' is hydrogen and R" is alkyl, the substituted amino group is sometimes referred to herein as alkylamino. When R' and R" are alkyl, the substituted amino group is sometimes referred to herein as dialkylamino. When referring to a monosubstituted amino, it is meant that either R' or R" is hydrogen but not both. When referring to a disubstituted amino, it is meant that neither R' nor R" are hydrogen.

"Aminocarbonyl" refers to the group —C(O)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonyl" refers to the group —C(S)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonylamino" refers to the group —NRC(O)NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonylamino" refers to the group —NRC(S)NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonyloxy" refers to the group —O—C(O)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyl" refers to the group —SO$_2$NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyloxy" refers to the group —O—SO$_2$NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonylamino" refers to the group —NRSO$_2$NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkyenyl, heteroaryl, substituted heteroaryl, heterocyclic, and substituted heterocyclic, and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkyenyl, aryl, substituted aryl, heteroaryl, substituted heteroaryl, heterocyclic and substituted heterocyclic are as defined herein.

"Amidino" refers to the group —C(=NR''')R'R" where R', R", and R''' are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aryloxy" refers to the group —O-aryl, where aryl is as defined herein, that includes, by way of example, phenoxy and naphthoxy.

"Substituted aryloxy" refers to the group —O-(substituted aryl), where substituted aryl is as defined herein.

"Arylthio" refers to the group —S-aryl, where aryl is as defined herein.

"Substituted arylthio" refers to the group —S-(substituted aryl), where substituted aryl is as defined herein.

"Alkynyl" refers to alkynyl groups having from 2 to 6 carbon atoms and preferably 2 to 3 carbon atoms and having at least 1 and preferably from 1 to 2 sites of alkynyl unsaturation.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, sulfo, substituted sulfonyl, sulfonyloxy, thioacyl, thiol, alkylthio, and substituted alkylthio, wherein said substituents are defined herein and with the proviso that any hydroxy substitution is not attached to an acetylenic carbon atom.

"Carbonyl" refers to the divalent group —C(O)— which is equivalent to —C(=O)—.

"Carboxyl" or "carboxy" refers to —COOH or salts thereof.

"Carboxyl alkyl" or "carboxyalkyl" refers to the group —(CH$_2$)$_n$COOH, where n is 1-6.

"Carboxyl ester" or "carboxy ester" refers to the groups —C(O)O-alkyl, —C(O)O— substituted alkyl, —C(O)O-alkenyl, —C(O)O-substituted alkenyl, —C(O)O-alkynyl, —C(O)O— substituted alkynyl, —C(O)O-aryl, —C(O)O-substituted aryl, —C(O)O-cycloalkyl, —C(O)O— substituted cycloalkyl, —C(O)O-cycloalkenyl, —C(O)O-substituted cycloalkenyl, —C(O)O— heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)amino" refers to the group —NR—C(O)O-alkyl, —NR)C(O)O— substituted alkyl, —NR—C(O)O-alkenyl, —NR—C(O)O-substituted alkenyl, —NR—C(O)O-alkynyl, —NR—C(O)O— substituted alkynyl, —NR—C(O)O-aryl, —NR—C(O)O-substituted aryl, —NR—C(O)O-cycloalkyl, —NR—C(O)O-substituted cycloalkyl, —NR—C(O)O-cycloalkenyl, —NR—C(O)O-substituted cycloalkenyl, —NR—C(O)O-heteroaryl, —NR—C(O)O-substituted heteroaryl, —NR—C(O)O-heterocyclic, and —NR—C(O)O-substituted heterocyclic, wherein R is alkyl or hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O— substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O— heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, and cyclooctyl.

"Cycloalkenyl" refers to non-aromatic cyclic alkyl groups of from 3 to 10 carbon atoms having single or multiple cyclic rings and having at least one >C=C<ring unsaturation and preferably from 1 to 2 sites of >C=C<ring unsaturation.

"Substituted cycloalkyl" and "substituted cycloalkenyl" refer to a cycloalkyl or cycloalkenyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, sulfo, substituted sulfonyl, sulfonyloxy, thioacyl, thiol, alkylthio, and substituted alkylthio, wherein said substituents are defined herein.

"Cycloalkyloxy" refers to —O-cycloalkyl.

"Substituted cycloalkyloxy" refers to —O-(substituted cycloalkyl).

"Cycloalkylthio" refers to —S-cycloalkyl.

"Substituted cycloalkylthio" refers to —S-(substituted cycloalkyl).

"Cycloalkenyloxy" refers to —O-cycloalkenyl.

"Substituted cycloalkenyloxy" refers to —O-(substituted cycloalkenyl).

"Cycloalkenylthio" refers to —S-cycloalkenyl.

"Substituted cycloalkenylthio" refers to —S-(substituted cycloalkenyl).

"Guanidino" refers to the group —NHC(=NH)NH$_2$.

"Substituted guanidino" refers to —NR$^{13}$C(=NR$^{13}$)N(R$^{13}$)$_2$ where each R$^{13}$ is independently selected from the group consisting of hydrogen, alkyl, substituted alkyl, aryl, substituted aryl, heteroaryl, substituted heteroaryl, heterocyclic, and substituted heterocyclic and two R$^{13}$ groups attached to a common guanidino nitrogen atom are optionally joined together with the nitrogen bound thereto to form a heterocyclic or substituted heterocyclic group, provided that at least one R$^{13}$ is not hydrogen, and wherein said substituents are as defined herein.

"H" indicates hydrogen.

"Halo" or "halogen" refers to fluoro, chloro, bromo and iodo.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy" refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or unsaturated group having a single ring or multiple condensed rings, including fused bridged and spiro ring systems, from 1 to 10 carbon atoms and from 1 to 4 hetero atoms selected from the group consisting of nitrogen, sulfur or oxygen within the ring wherein, in fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties.

"Substituted heterocyclic" or "substituted heterocycloalkyl" or "substituted heterocyclyl" refers to heterocyclyl groups that are substituted with from 1 to 5, or preferably 1 to 3 of the same substituents as defined for substituted cycloalkyl.

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Heterocyclyloxy" refers to the group —O-heterocyclyl.

"Substituted heterocyclyloxy" refers to the group —O-(substituted heterocyclyl).

"Heterocyclylthio" refers to the group —S— heterocyclyl.

"Substituted heterocyclylthio" refers to the group —S-(substituted heterocyclyl).

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Hydrazinyl" refers to the group —NHNH$_2$— or =NNH—.

"Substituted hydrazinyl" refers to a hydrazinyl group, wherein a non-hydrogen atom, such as an alkyl group, is appended to one or both of the hydrazinyl amine groups. An example of substituted hydrazinyl is —N(alkyl)-NH$_2$ or =N$^+$(alkyl)-NH$_2$.

"Nitro" refers to the group —NO$_2$.

"Oxo" refers to the atom (=O) or (—O$^-$).

"PEG groups" refer to ethylene glycol, diethylene glycol and polyethylene glycol groups.

"Spirocyclyl" refers to divalent saturated cyclic group from 3 to 10 carbon atoms having a cycloalkyl or heterocyclyl ring with a spiro union (the union formed by a single atom which is the only common member of the rings) as exemplified by the following structure:

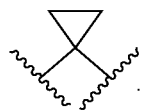 [SMILES: *C1(*)CC1]

"Sulfo" refers to —SO$_3^-$ and —SO$_3$H.

"Sulfoalkyl" refers to -alkyl-SO$_3^-$ or alkyl-SO$_3$H, wherein alkyl is defined herein.

"Sulfonyl" refers to the divalent group —S(O)$_2$—.

"Substituted sulfonyl" refers to the group —SO$_2$-alkyl, —SO$_2$-substituted alkyl, —SO$_2$— alkenyl, —SO$_2$-substituted alkenyl, —SO$_2$-cycloalkyl, —SO$_2$-substituted cycloalkyl, —SO$_2$-cycloalkenyl, —SO$_2$-substituted cycloalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Substituted sulfonyl includes groups such as methyl-SO$_2$—, phenyl-SO$_2$—, and 4-methylphenyl-SO$_2$—.

"Sulfonyloxy" refers to the group —OSO$_2$-alkyl, —OSO$_2$-substituted alkyl, —OSO$_2$— alkenyl, —OSO$_2$-substituted alkenyl, —OSO$_2$-cycloalkyl, —OSO$_2$-substituted cycloalkyl, —OSO$_2$-cycloalkenyl, —OSO$_2$-substituted cylcoalkenyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thiol" refers to the group —SH.

"Thiocarbonyl" refers to the divalent group —C(S)— which is equivalent to C(=S)—.

"Thione" refers to the atom (=S).

"Alkylthio" refers to the group —S-alkyl wherein alkyl is as defined herein.

"Substituted alkylthio" refers to the group —S-(substituted alkyl), wherein substituted alkyl is as defined herein.

The term "carrier molecule" as used herein, refers to a biological or a non-biological component that is or becomes covalently bonded to a dye compound disclosed herein. Such components include, but are not limited to, an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, polyethylene glycol (PEG) groups, a polymeric microparticle, a biological cell, a virus and combinations thereof. Included is one embodiment in which carrier molecules comprise an organic moiety having at least 4 plural valent atoms and often more than 10 plural valent atoms (i.e., atoms other than hydrogen and halo), e.g. at least 15 such atoms, as in the case of moieties having at least 20 such atoms.

The term "conjugated substance" or "$S_c$" refers to a carrier molecule or solid support.

The term "detectable response" as used herein refers to an occurrence of or a change in, a signal that is directly or indirectly detectable either by observation or by instrumentation. Typically, the detectable response is an optical response resulting in a change in the wavelength distribution patterns or intensity of absorbance or fluorescence or a change in light scatter, fluorescence lifetime, fluorescence polarization, or a combination of the above parameters.

The term "dye" as used herein refers to a compound that emits light to produce an observable detectable signal.

As used herein, the term "fluorophore" or "fluorogenic" refers to a compound or a composition that demonstrates a change in fluorescence upon binding to a biological compound or analyte of interest and/or upon cleavage by an enzyme. The fluorophores of the present disclosure may be substituted to alter the solubility, spectral properties or physical properties of the fluorophore.

As used herein, "a pharmaceutically acceptable salt" or "a biologically compatible salt" is a counterion that is not toxic as used, and does not have a substantially deleterious effect on biomolecules. Examples of such salts include, among others, $K^+$, $Na^+$, $Cs^+$, $Li^+$, $Ca^+$, $Mg^{2+}$, $Cl^-$, $AcO^-$, and alkylammonium or alkoxyammonium salts.

The term "linker" or "L", as used herein, refers to a single covalent bond or a moiety comprising series of stable covalent bonds, the moiety often incorporating 1-40 plural valent atoms selected from the group consisting of C, N, O, S and P that covalently attach the fluorogenic or fluorescent compounds to another moiety such as a chemically reactive group or a biological and non-biological component. The number of plural valent atoms in a linker may be, for example, 0, 1, 2, 3, 4, 5, 6, 7, 8, 9, 10, 20, 25, 30 or a larger number up to 40 or more. A linker may be linear or non-linear; some linkers have pendant side chains or pendant functional groups, or both. Examples of such pendant moieties are hydrophilicity modifiers, for example solubilizing groups like, e.g. sulfo (—$SO_3H$ or —$SO_3^-$). In certain embodiments, L is composed of any combination of single, double, triple or aromatic carboncarbon bonds, carbonnitrogen bonds, nitrogennitrogen bonds, carbonoxygen bonds and carbonsulfur bonds. Exemplary linking members include a moiety that includes —C(O)NH—, —C(O)O—, —NH—, —S—, —O—, and the like. Linkers may, by way of example, consist of a combination of moieties selected from alkyl; C(O)NH—; —C(O)O—; —NH—; —S—; —O—; —C(O)—; —S(O)$_n$— where n is 0, 1 or 2; —O—; 5- or 6-membered monocyclic rings; and optional pendant functional groups, for example sulfo, hydroxy and carboxy. The moiety formed by a linker bonded to a reactive group ($R_x$) may be designated -L-$R_x$. The reactive group may be reacted with a substance reactive therewith, whereby the linker becomes bonded to a conjugated substance ($S_c$) and may be designated -L-$S_c$, or in some cases, the linker may contains a residue of a reactive group (e.g. the carbonyl group of an ester) and may be designated "-$L_R$". A "cleavable linker" is a linker that has one or more cleavable groups that may be broken by the result of a reaction or condition. The term "cleavable group" refers to a moiety that allows for release of a portion, e.g., a fluorogenic or fluorescent moiety, of a conjugate from the remainder of the conjugate by cleaving a bond linking the released moiety to the remainder of the conjugate. Such cleavage is either chemical in nature, or enzymatically mediated. Exemplary enzymatically cleavable groups include natural amino acids or peptide sequences that end with a natural amino acid.

In addition to enzymatically cleavable groups, it is within the scope of the present invention to include one or more sites that are cleaved by the action of an agent other than an enzyme. Exemplary non-enzymatic cleavage agents include, but are not limited to, acids, bases, light (e.g., nitrobenzyl derivatives, phenacyl groups, benzoin esters), and heat. Many cleavable groups are known in the art. See, for example, Jung et al., *Biochem. Biophys. Acta*, 761:152-162 (1983); Joshi et al., *J. Biol. Chem.*, 265:14518-14525 (1990); Zarling et al., *J. Immunol.*, 124:913-920 (1980); Bouizar et al., *Eur. J. Biochem.*, 155:141-147 (1986); Park et al., *J. Biol. Chem.*, 261:205-210 (1986); Browning et al., *J. Immunol.*, 143:1859-1867 (1989). Moreover a broad range of cleavable, bifunctional (both homo- and hetero-bifunctional) spacer arms are commercially available.

An exemplary cleavable group, such as an ester, is cleavable group that may be cleaved by a reagent, e.g., sodium hydroxide, resulting in a carboxylate-containing fragment and a hydroxyl-containing product.

The linker may be used to attach the dye compound to another component of a conjugate, such as a targeting moiety (e.g., antibody, ligand, non-covalent protein-binding group, etc.), an analyte, a biomolecule, a drug and the like.

The term "reactive group" (or "$R_x$"), as used herein, refers to a group that is capable of reacting with another chemical group to form a covalent bond, i.e., is covalently reactive under suitable reaction conditions, and generally represents a point of attachment for another substance. The reactive group is a moiety, such as carboxylic acid or succinimidyl ester, on the compounds of the present disclosure that is capable of chemically reacting with a functional group on a different compound to form a covalent linkage. Reactive groups generally include nucleophiles, electrophiles and photoactivatable groups.

Exemplary reactive groups include, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides, succinimidyl esters (SE), sulfodichlorophenyl (SDP) esters, sulfotetrafluorophenyl (STP) esters, tetrafluorophenyl (TFP) esters, pentafluorophenyl (PFP) esters, nitrilotriacetic acids (NTA), aminodextrans, cyclooctyne-amines and the like. Methods to prepare each of these functional groups are well known in the art and their application to or modification for a particular purpose is within the ability of one of skill in the art (see, for example, Sandler and Karo, eds., *Organic Functional Group Preparations*, Academic Press, San Diego, 1989).

The term "solid support," as used herein, refers to a matrix or medium that is substantially insoluble in liquid phases and capable of binding a molecule or particle of interest. Solid supports suitable for use herein include semi-solid supports and are not limited to a specific type of support. Useful solid supports include solid and semi-solid matrixes, such as aerogels and hydrogels, resins, beads, biochips (including thin film coated biochips), microfluidic chip, a silicon chip, multi-well plates (also referred to as microtitre plates or microplates), membranes, conducting and nonconducting metals, glass (including microscope slides) and magnetic supports. More specific examples of useful solid supports include silica gels, polymeric membranes, particles, derivatized plastic films, glass beads, cotton, plastic beads, alumina gels, polysaccharides such as SEPHAROSE (GE Healthcare), poly(acrylate), polystyrene, poly(acrylamide), polyol, agarose, agar, cellulose, dextran, starch, FICOLL (GE Healthcare), heparin, glycogen, amylopectin, mannan, inulin, nitrocellulose, diazocellulose, polyvinylchloride, polypropylene, polyethylene (including poly(ethylene glycol)), nylon, latex bead, magnetic bead, paramagnetic bead, superparamagnetic bead, starch and the like.

Compounds and Compositions:

In general, for ease of understanding the present disclosure, compounds and corresponding substituents will first be described in detail, followed by various methods in which the compounds of the present disclosure are useful, which is followed by exemplary methods of use of certain compounds that are particularly advantageous for use with the methods provided herein.

The compounds disclosed herein are useful for short- and long-term tracking of cell proliferation, differentiation and/or function, as well as for staining samples, labeling proteins, detecting ligands and other analytes.

Cell movement and location studies require detectable compounds that are non-toxic to living cells and are available in a range of fluorescent colors to match instrument lasers and filters and to accommodate co-staining with antibodies or other cell analysis compounds. The compounds described herein are useful for monitoring cell movement, location, proliferation, migration, chemotaxis and invasion. The compounds described herein can pass freely through the cell membrane; however, once inside the cell, they are transformed into cell-impermeant reaction products and are well retained in living cells over several generations. The compounds described herein are transferred to daughter cells, but not to adjacent cells in a population. The compounds disclosed herein have the following advantages: they have a high signal:noise (S:N) ratio by imaging and flow cytometry; they are non-toxic to cells thereby allowing for tracking of multiple cell divisions; they are highly cell permeable; and they are brightly fluorescent at physiological pH.

The compounds described herein can permanently label cells without affecting the cell's morphology or physiology in order to trace generations or divisions both in vivo and in vitro. The bright, single-peak staining of the compounds described herein enables visualization of multiple generations with long-term signal stability. The compounds described herein are well retained within cells for several days post-stain. The compounds are non-cytotoxic, meaning that they have no known effect on the proliferation ability or biology of the cells. The compounds described herein are reactive fluorescent molecules which enter the cells freely via diffusion. Upon entering the cell, the compounds react with intracellular proteins thereby allowing the conjugated compounds to be retained within the cells. Daughter cells receive approximately half of the label from the parent. Analysis of the level of fluorescence in the cell population by flow cytometry, for example, permits determination of the number of generations through which the cell has progressed since the label was applied.

One illustrative embodiment provides a compound having structural formula (I):

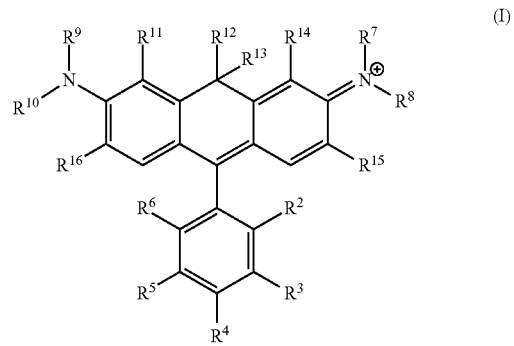

or a pharmaceutically acceptable salt thereof, wherein $R^{12}$ and $R^{13}$ are each independently H, alkyl, substituted alkyl, or -L-$R_x$, or -L-$S_c$;

$R^2$, $R^3$, $R^4$, $R^5$, $R^6$, $R^7$, $R^8$, $R^9$, $R^{10}$, $R^{11}$, $R^{14}$, $R^{15}$, and $R^{16}$ are each independently H, halogen, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester) amino, (carboxyl ester) oxy, cyano, alkylcarboxylate, hydroxyl, nitro, sulfo, sulfoalkyl, substituted sulfoalkyl, sulfonyl, substituted sulfonyl, sulfonyloxy, thioacyl, thiol, alkylthiol, substituted alkylthiol, aryl, substituted aryl, heteroaryl, substituted heteroaryl, cycloalkyl, substituted cycloalkyl, heterocyclyl, substituted heterocyclyl, -L-$R_x$, or -L-$S_c$; or $R^7$ taken together with $R^{14}$ are part of an optionally substituted 5- or 6-membered ring;

$R^8$ taken together with $R^{15}$ are part of an optionally substituted 5- or 6-membered ring;

$R^9$ taken together with $R^{11}$ are part of an optionally substituted 5- or 6-membered ring;

$R^{10}$ taken together with $R^{16}$ are part of an optionally substituted 5- or 6-membered ring;

L is a linker;

$R_x$ is a reactive group; and $S_c$ is a conjugated substance.

In certain embodiments, $R^2$ is carboxyl, -L-$R_x$, or -L-$S_c$. In certain embodiments, $R^7$, $R^8$, $R^9$, and $R^{10}$ are each independently H, alkyl, substituted alkyl, or sulfoalkyl. In certain embodiments, $R^7$, $R^8$, $R^9$, and $R^{10}$ are each independently a $C_1$-$C_6$ alkyl, which can be the same or different. In certain embodiments, $R^7$, $R^8$, $R^9$, and $R^{10}$ are each methyl.

In certain embodiments, $R^{12}$ and $R^{13}$ are each alkyl, preferably a $C_1$-$C_6$ alkyl. In certain embodiments, $R^{12}$ and $R^{13}$ are each methyl. In certain embodiments, $R^{11}$ and $R^{14}$ are each independently alkyl, substituted alkyl, sulfoalkyl, sulfo, -L-$R_x$, or -L-$S_c$. In certain embodiments, $R^{11}$ and $R^{14}$ are each independently a $C_1$-$C_6$ alkyl, a $C_1$-$C_6$ substituted alkyl, or sulfoalkyl, which can be the same or different. In certain embodiments, $R_x$ is succinimidyl ester (SE), sulfodichlorophenyl (SDP) ester, sulfotetrafluorophenyl (STP) ester, tetrafluorophenyl (TFP) ester, pentafluorophenyl (PFP) ester, nitrilotriacetic acid (NTA), aminodextran, and cyclooctyne-amine.

Another illustrative embodiment provides a compound having structural formula (II):

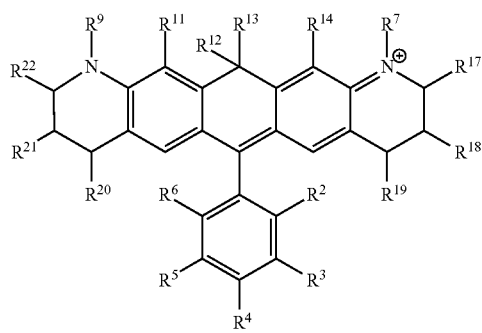

(II)

or a pharmaceutically acceptable salt thereof, wherein $R^{12}$ and $R^{13}$ are each independently H, alkyl, substituted alkyl, or -L-$R_x$, or -L-$S_c$;

$R^2$, $R^3$, $R^4$, $R^5$, $R^6$, $R^7$, $R^9$, $R^{11}$, $R^{14}$, $R^{17}$, $R^{18}$, $R^{19}$, $R^{20}$, $R^{21}$ and $R^{22}$ are each independently H, halogen, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester) amino, (carboxyl ester) oxy, cyano, alkylcarboxylate, hydroxyl, nitro, sulfo, sulfoalkyl, substituted sulfoalkyl, sulfonyl, substituted sulfonyl, sulfonyloxy, thioacyl, thiol, alkylthiol, substituted alkylthiol, aryl, substituted aryl, heteroaryl, substituted heteroaryl, cycloalkyl, substituted cycloalkyl, heterocyclyl, substituted heterocyclyl, -L-$R_x$, or -L-$S_c$;

L is a linker;

$R_x$ is a reactive group; and $S_c$ is a conjugated substance.

In certain embodiments, $R^{12}$ and $R^{13}$ are each alkyl, preferably a $C_1$-$C_6$ alkyl. In certain embodiments, $R^{12}$ and $R^{13}$ are each methyl. In certain embodiments, $R^2$ is carboxyl, -L-$R_x$, or -L-$S_c$. In certain embodiments, $R^3$, $R^4$, $R^5$ and $R^6$ are each independently H or halo. In certain embodiments, $R^3$, $R^4$, $R^5$ and $R^6$ are independently H, Cl, or F. In certain embodiments, $R^7$ and $R^9$ are each independently alkyl, substituted alkyl, sulfoalkyl, sulfo, -L-$R_x$, or -L-$S_c$. In certain embodiments, $R^7$ and $R^9$ are each independently methyl, -L-$R_x$, -L-$S_c$ or $(CH_2)_nSO_3^-$, wherein n is an integer between 1 and 6. In certain embodiments, n is 3. In certain embodiments, $R_x$ is succinimidyl ester (SE), sulfodichlorophenyl (SDP) ester, sulfotetrafluorophenyl (STP) ester, tetrafluorophenyl (TFP) ester, pentafluorophenyl (PFP) ester, nitrilotriacetic acid (NTA), aminodextran, and cyclooctyne-amine.

Another illustrative embodiment provides a compound having structural formula (III):

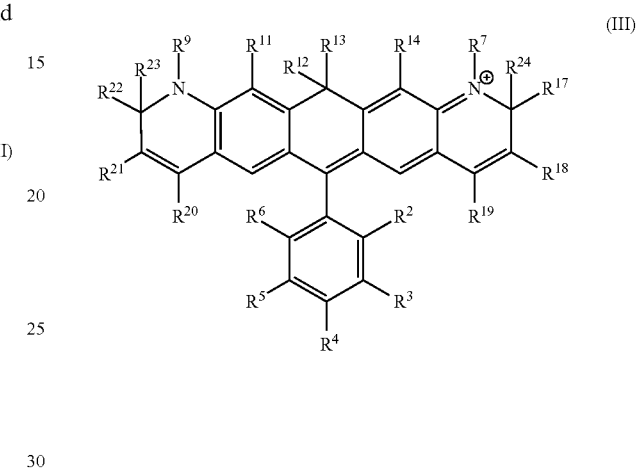

(III)

or a pharmaceutically acceptable salt thereof, wherein $R^{12}$ and $R^{13}$ are each independently H, alkyl, substituted alkyl, or -L-$R_x$, or -L-$S_c$;

$R^2$, $R^3$, $R^4$, $R^5$, $R^6$, $R^7$, $R^9$, $R^{11}$, $R^{14}$, $R^{17}$, $R^{18}$, $R^{19}$, $R^{20}$, $R^{21}$, $R^{22}$, $R^{23}$, and $R^{24}$ are each independently H, halogen, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester) amino, (carboxyl ester) oxy, cyano, alkylcarboxylate, hydroxyl, nitro, sulfo, sulfoalkyl, substituted sulfoalkyl, sulfonyl, substituted sulfonyl, sulfonyloxy, thioacyl, thiol, alkylthiol, substituted alkylthiol, aryl, substituted aryl, heteroaryl, substituted heteroaryl, cycloalkyl, substituted cycloalkyl, heterocyclyl, substituted heterocyclyl, -L-$R_x$, or -L-$S_c$;

L is a linker;

$R_x$ is a reactive group; and $S_c$ is a conjugated substance.

In certain embodiments, $R^{12}$ and $R^{13}$ are each alkyl, preferably a $C_1$-$C_6$ alkyl. In certain embodiments, $R^{12}$ and $R^{13}$ are each methyl. In certain embodiments, $R^2$ is carboxyl, -L-$R_x$, or -L-$S_c$. In certain embodiments, $R^7$, $R^9$, $R^{17}$, $R^{19}$, $R^{20}$, $R^{22}$, $R^{23}$ and $R^{24}$ are each independently alkyl, substituted alkyl, sulfoalkyl, sulfo, -L-$R_x$, or -L-$S_c$. In certain embodiments, $R^7$, $R^9$, $R^{17}$, $R^{22}$, $R^{23}$, and $R^{24}$ are each methyl. In certain embodiments, $R^{19}$ and $R^{20}$ are each independently $(CH_2)_nSO_3^-$, wherein n is an integer between 1 and 6. In certain embodiments, n is 1. In certain embodiments, $R_x$ is succinimidyl ester (SE), sulfodichlorophenyl (SDP) ester, sulfotetrafluorophenyl (STP) ester, tetrafluorophenyl (TFP) ester, pentafluorophenyl (PFP) ester, nitrilotriacetic acid (NTA), aminodextran, and cyclooctyne-amine.

Another illustrative embodiment provides a compound having structural formula (IV):

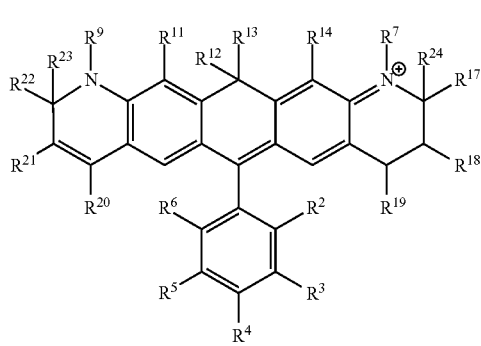

or a pharmaceutically acceptable salt thereof, wherein
$R^{12}$ and $R^{13}$ are each independently H, alkyl, substituted alkyl, or -L-$R_x$, or -L-$S_c$;
$R^2$, $R^3$, $R^4$, $R^5$, $R^6$, $R^7$, $R^9$, $R^{11}$, $R^{14}$, $R^{17}$, $R^{18}$, $R^{19}$, $R^{20}$, $R^{21}$, $R^{22}$, $R^{23}$ and $R^{24}$ are each independently H, halogen, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester) amino, (carboxyl ester) oxy, cyano, alkylcarboxylate, hydroxyl, nitro, sulfo, sulfoalkyl, substituted sulfoalkyl, sulfonyl, substituted sulfonyl, sulfonyloxy, thioacyl, thiol, alkylthiol, substituted alkylthiol, aryl, substituted aryl, heteroaryl, substituted heteroaryl, cycloalkyl, substituted cycloalkyl, heterocyclyl, substituted heterocyclyl, -L-$R_x$, or -L-$S_c$;
L is a linker;
$R_x$ is a reactive group; and
$S_c$ is a conjugated substance.
In certain embodiments, $R^9$, $R^{12}$, $R^{13}$, $R^{22}$ and $R^{23}$ are each alkyl, preferably a $C_1$-$C_6$ alkyl. In certain embodiments, $R^9$, $R^{12}$, $R^{13}$, $R^{22}$ and $R^{23}$ are each methyl. In certain embodiments, $R^3$, $R^4$, $R^5$ and $R^6$ are each independently H or halo. In certain embodiments, $R^3$ and $R^6$ are independently H, Cl, or F. In certain embodiments, $R^2$ is carboxyl. In certain embodiments, $R^7$, $R^9$ and $R^{20}$ are each independently alkyl, substituted alkyl, sulfoalkyl, sulfo, $(CH_2)_n SO_3^-$, wherein n is an integer between 1 and 6, -L-$R_x$, or -L-$S_c$. In certain embodiments, $R^7$ is L-$R_x$ and $R^{20}$ is $(CH_2)_n SO_3^-$. In certain embodiments, n is 1. In certain embodiments, $R_x$ is succinimidyl ester (SE), sulfodichlorophenyl (SDP) ester, sulfotetrafluorophenyl (STP) ester, tetrafluorophenyl (TFP) ester, pentafluorophenyl (PFP) ester, nitrilotriacetic acid (NTA), aminodextran, and cyclooctyne-amine.
In certain embodiments, $R_x$ is selected from an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, an imido ester, an isocyanate, an isothiocyanate, a maleimide, a phosphoramidite, a photoactivatable group, a reactive platinum complex, a silyl halide, a sulfonyl halide, and a thiol. In certain embodiments the reactive group is selected from the group consisting of carboxylic acid, succinimidyl ester of a carboxylic acid, hydrazide, amine and a maleimide. The reactive group may be attached to any appropriate site on the reporter molecule or the aniline moiety. In certain embodiments, at least one member selected from $R^2$, $R^3$, $R^4$, $R^5$, $R^6$, $R^7$, $R^8$, $R^9$, $R^{10}$, $R^{12}$, $R^{13}$, $R^{19}$ and $R^{20}$ is a reactive group. In certain embodiments, at least one of $R^2$, $R^4$, $R^5$, $R^7$, $R^8$, $R^9$, $R^{10}$, $R^{12}$ and $R^{13}$ is a reactive group. In certain embodiments, at least one of $R^7$, $R^8$, $R^9$, $R^{10}$, $R^{12}$ and $R^{13}$ is a reactive group.

In certain embodiments, $S_c$ is selected from a carrier molecule and a solid support. In certain embodiments, $S_c$ is selected from an amino acid, a polymer of amino acids, a peptide, a protein, a neurotoxin, a phallotoxin, a cytokine, a toxin, a protease substrate, a protein kinase substrate, an enzyme, an antibody, an antibody fragment, a lectin, a glycoprotein, a histone, an albumin, a lipoprotein, avidin, streptavidin, protein A, protein G, a phycobiliprotein, a fluorescent protein, a hormone, a growth factor, a nucleic acid base, a nucleoside, a nucleotide, a nucleic acid polymer, a nucleotide analog, a nucleoside analog, a nucleoside triphosphate, a deoxynucleoside triphosphate, a dideoxynucleoside triphosphate, a hapten, a carbohydrate, a polysaccharide, a lipid, an ion-complexing moiety (such as a crown ether), a PEG group, and an organic or inorganic polymer. In certain embodiments, at least one member selected from $R^2$, $R^3$, $R^4$, $R^5$, $R^6$, $R^7$, $R^8$, $R^9$, $R^{10}$, $R^{12}$, $R^{13}$, $R^{19}$ and $R^{20}$ is a conjugated substance. In certain embodiments, at least one of $R^2$, $R^4$, $R^5$, $R^7$, $R^8$, $R^9$, $R^{10}$, $R^{12}$ and $R^{13}$ is a conjugated substance. In certain embodiments, at least one of $R^7$, $R^8$, $R^9$, $R^{10}$, $R^{12}$ and $R^{13}$ is a conjugated substance. In certain embodiments, at least one of $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ is a PEG group.

In certain embodiments, one or more PEG groups are added to the carbopyronine compounds. Ethylene glycol, diethylene glycol and polyethylene glycol are herein collectively referred to as PEG. The PEG groups are either directly or indirectly linked to the compounds. Indirect attachment indicates the use of a linker. Direct attachment indicates lack of a linker.

In certain embodiments, compounds are provided selected from the group consisting of:

Compound 1

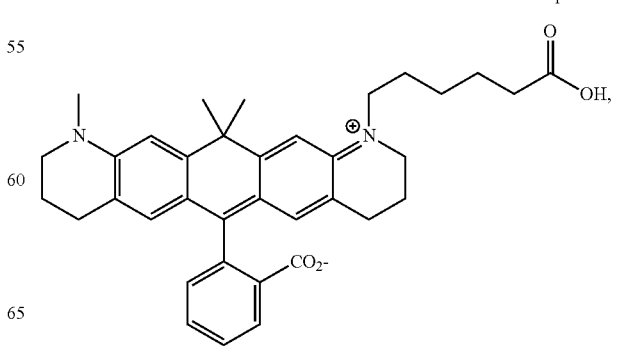

-continued
Compound 2
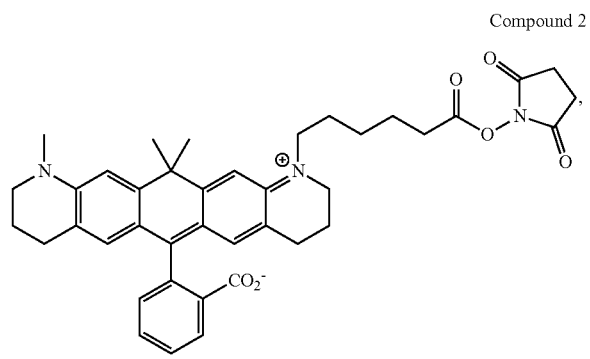
Compound 3
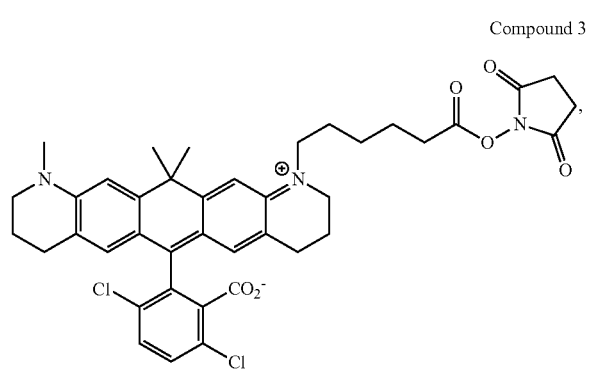
Compound 4
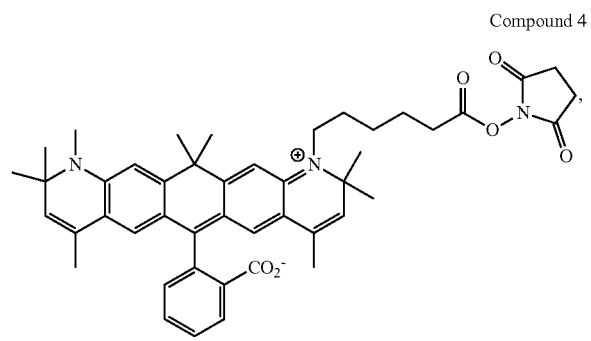
Compound 5
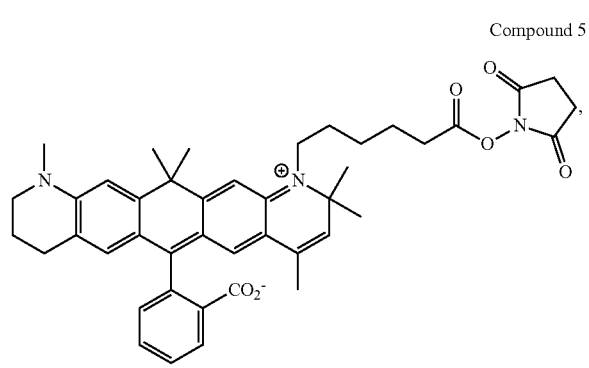
-continued
Compound 6
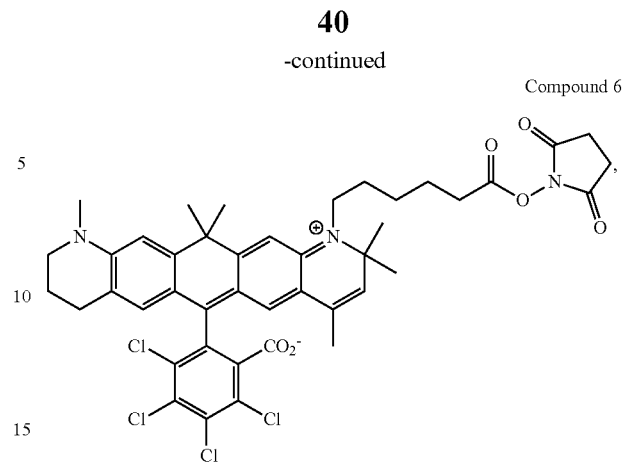
Compound 7
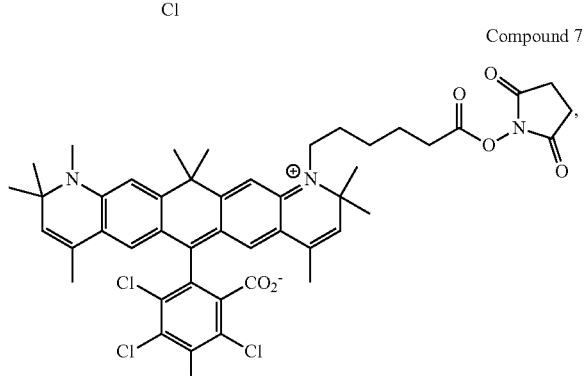
Compound 8
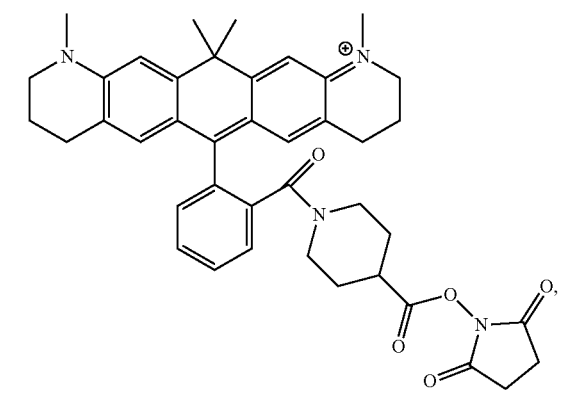
Compound 9
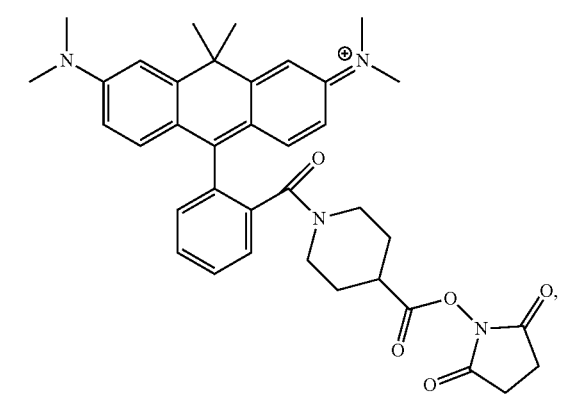

Compound 10
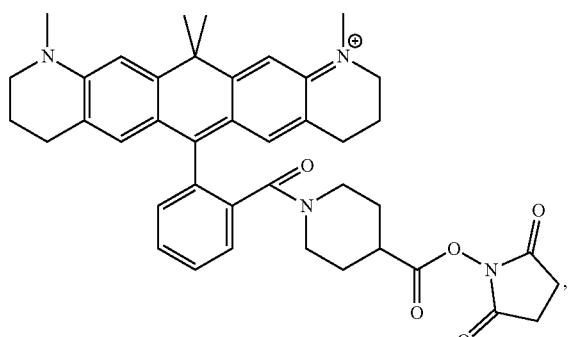
Compound 11
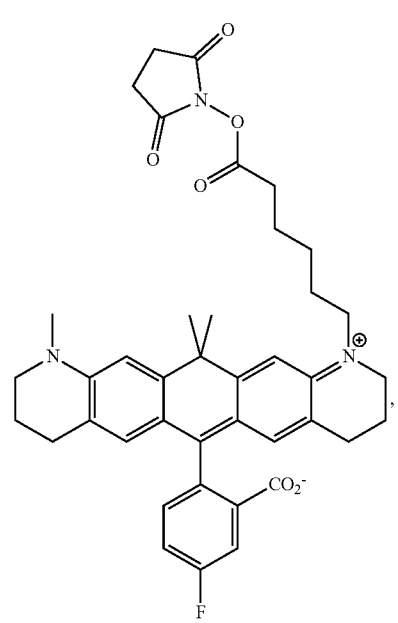
Compound 12
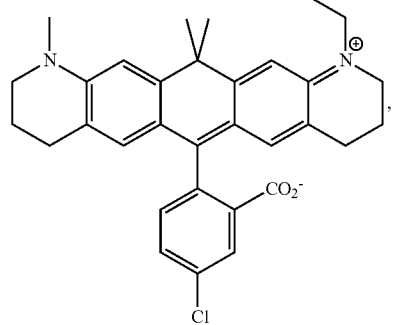
Compound 13
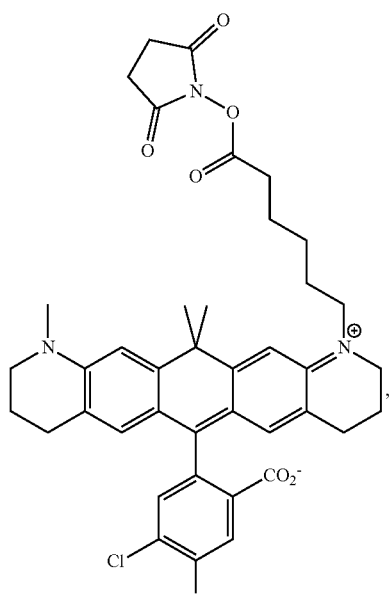
Compound 14
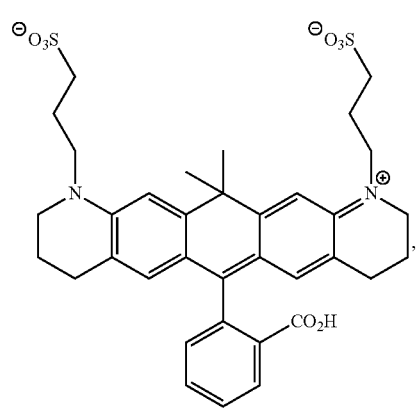
Compound 15
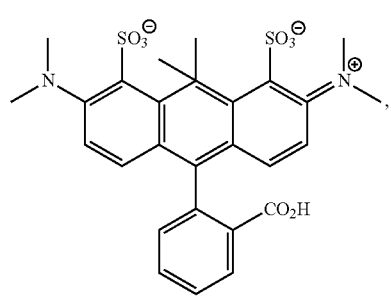
Compound 16
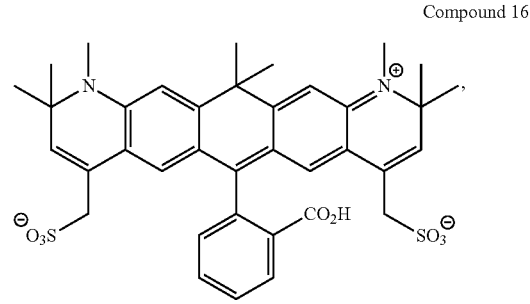

Compound 17
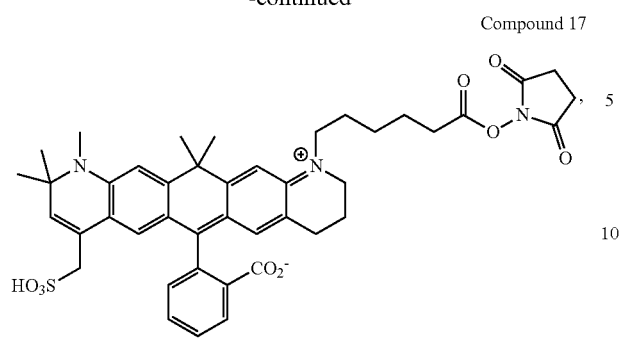
Compound 18
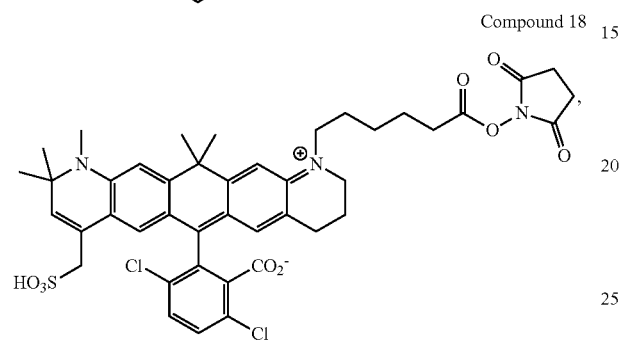
Compound 19
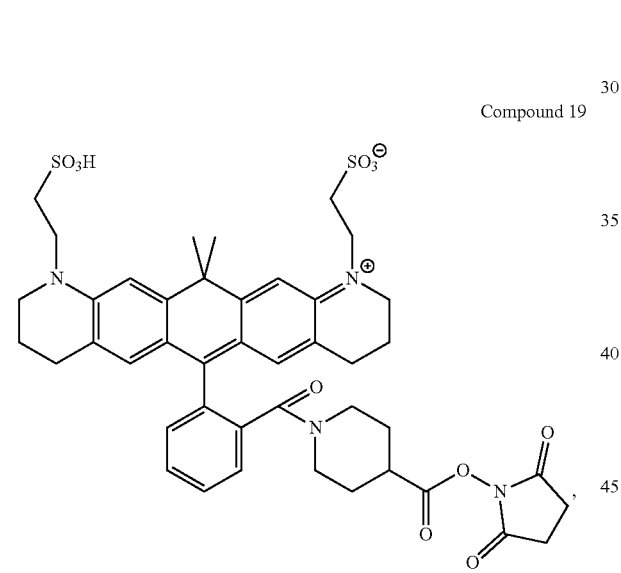
Compound 20
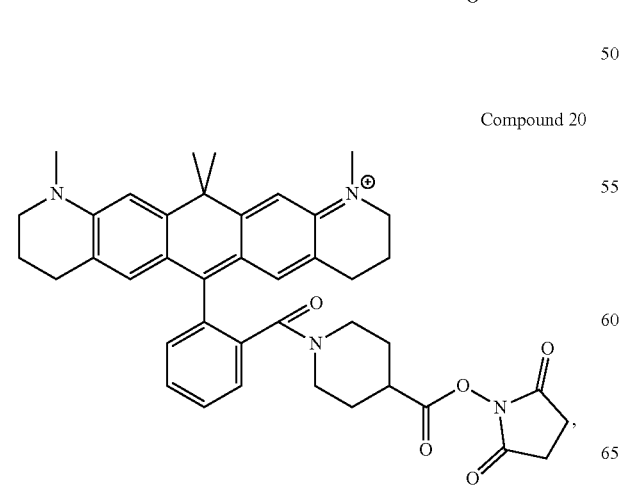
Compound 21
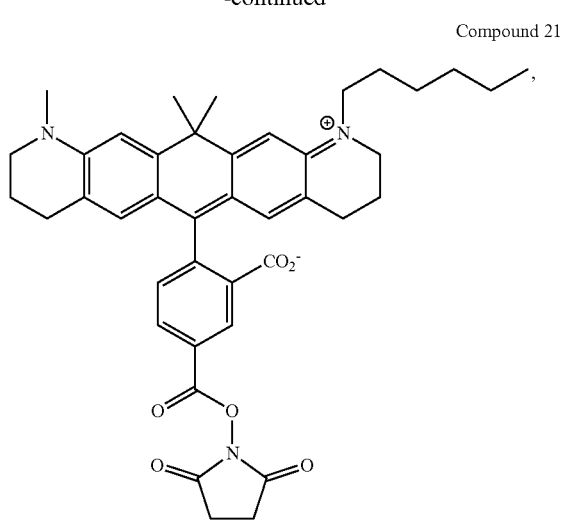
Compound 22
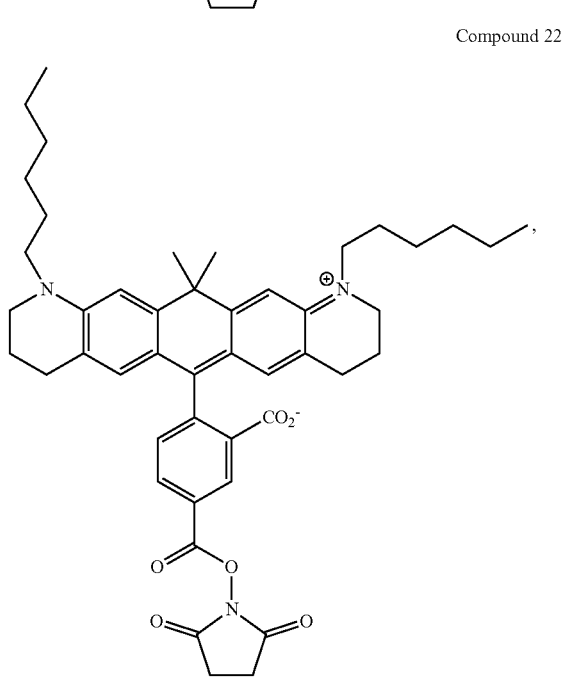
Compound 23
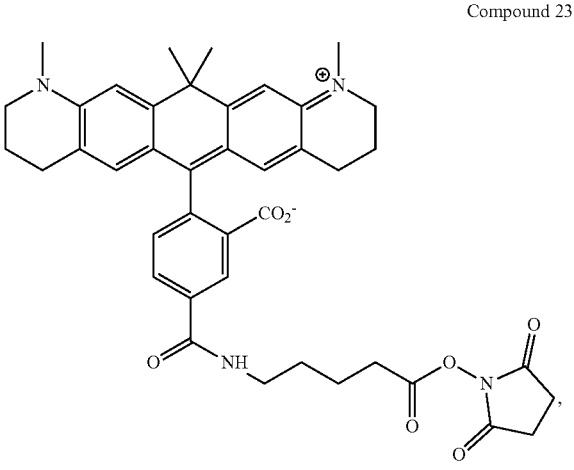

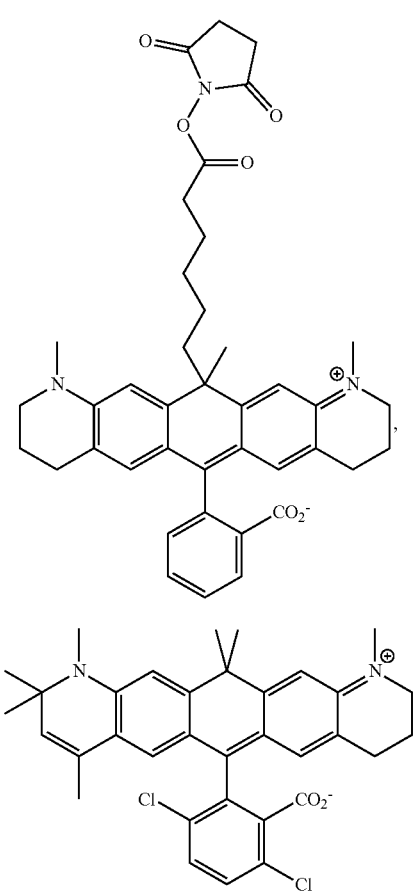

Compound 24

Compound 25 and amine-reactive forms thereof.

Reactive Groups:

In certain embodiments, the compounds provided herein are chemically reactive, and are substituted by at least one reactive group ($R_x$). The reactive group functions as the site of attachment for another moiety, such as a carrier molecule or a solid support, wherein the reactive group chemically reacts with an appropriate reactive or functional group on the carrier molecule or solid support. Thus, in certain embodiments, the compounds provided herein comprise an aniline moiety, linker, fluorophore, a reactive group moiety and optionally a carrier molecule and/or a solid support.

In certain embodiments, the compounds provided herein further comprise a reactive group which is a member selected from an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, an imido ester, an isocyanate, an isothiocyanate, a maleimide, a phosphoramidite, a photoactivatable group, a reactive platinum complex, a silyl halide, a sulfonyl halide, and a thiol. In certain embodiments the reactive group is selected from the group consisting of carboxylic acid, succinimidyl ester of a carboxylic acid, hydrazide, amine and a maleimide. The reactive group may be attached to any appropriate site on the reporter molecule or the aniline moiety. In certain embodiments, at least one member selected from $R^2$, $R^3$, $R^4$, $R^5$, $R^6$, $R^7$, $R^8$, $R^9$, $R^{10}$, $R^{12}$, $R^{13}$, $R^{19}$ and $R^{20}$ is a reactive group. In certain embodiments, at least one of $R^2$, $R^4$, $R^5$, $R^7$, $R^8$, $R^9$, $R^{10}$, $R^{12}$ and $R^{13}$ is a reactive group. In certain embodiments, at least one of $R^7$, $R^8$, $R^9$, $R^{10}$, $R^{12}$, and $R^{13}$ is a reactive group. Alternatively, if the compounds disclosed herein comprise a carrier molecule or solid support a reactive group may be covalently attached independently to those substituents, allowing for further conjugation to a fluorophore, carrier molecule or solid support.

These reactive groups are synthesized during the formation of the compounds provided herein and carrier molecule- and/or solid support-containing compounds to provide chemically reactive compounds. In this way, compounds incorporating a reactive group may be covalently attached to a wide variety of carrier molecules or solid supports that contain, or are modified to contain, functional groups with suitable reactivity, resulting in chemical attachment of the components. In certain embodiments, the reactive group of the compounds disclosed herein and the functional group of the carrier molecule or solid support comprise electrophiles and nucleophiles that can generate a covalent linkage between them. In certain embodiments, the reactive group comprises a photoactivatable group, which becomes chemically reactive only after illumination with light of an appropriate wavelength. Typically, the conjugation reaction between the reactive group and the carrier molecule or solid support results in one or more atoms of the reactive group being incorporated into a new linkage attaching the dye compounds disclosed herein to the carrier molecule or solid support. Selected examples of functional groups and linkages are shown in Table 1, where the reaction of an electrophilic group and a nucleophilic group yields a covalent linkage.

TABLE 1

Examples of some routes to useful covalent linkages

| Electrophilic Group | Nucleophilic Group | Resulting Covalent Linkage |
|---|---|---|
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| halotriazines | thiols | triazinyl thioethers |
| imido esters | amines/anilines | amidines |
| isocyanates | amines/anilines | ureas |

TABLE 1-continued

Examples of some routes to useful covalent linkages

| Electrophilic Group | Nucleophilic Group | Resulting Covalent Linkage |
| --- | --- | --- |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COΩ, where Ω is a suitable leaving group (e.g., succinimidyloxy (—OC$_4$H$_4$O$_2$), sulfosuccinimidyloxy (—OC$_4$H$_3$O$_2$—SO$_3$H), -1-oxybenzotriazolyl (—OC$_6$H$_4$N$_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCOR$^x$ or —OCNR$^x$NHR$^y$, where R$^x$ and R$^y$, which may be the same or different, are C$_1$-C$_6$ alkyl, C$_1$-C$_6$ perfluoroalkyl, or C$_1$-C$_6$ alkoxy; or cyclohexyl, 3-dimethylaminopropyl, or N-morpholinoethyl).
**Acyl azides can also rearrange to isocyanates.

The choice of the reactive group used to attach the dye compounds disclosed herein to the substance to be conjugated typically depends on the reactive or functional group on the substance to be conjugated and the type or length of covalent linkage desired. The types of functional groups typically present on the organic or inorganic substances (biomolecule or non-biomolecule) include, but are not limited to, amines, amides, thiols, alcohols, phenols, aldehydes, ketones, phosphates, imidazoles, hydrazines, hydroxylamines, disubstituted amines, halides, epoxides, silyl halides, carboxylate esters, sulfonate esters, purines, pyrimidines, carboxylic acids, olefinic bonds, or a combination of these groups. A single type of reactive site may be available on the substance (typical for polysaccharides or silica), or a variety of sites may occur (e.g., amines, thiols, alcohols, phenols), as is typical for proteins.

Typically, the reactive group will react with an amine, a thiol, an alcohol, an aldehyde, a ketone, or with silica. Preferably, reactive groups react with an amine or a thiol functional group, or with silica. In certain embodiments, the reactive group is an acrylamide, an activated ester of a carboxylic acid, an acyl azide, an acyl nitrile, an aldehyde, an alkyl halide, a silyl halide, an anhydride, an aniline, an aryl halide, an azide, an aziridine, a boronate, a diazoalkane, a haloacetamide, a halotriazine, a hydrazine (including hydrazides), an imido ester, an isocyanate, an isothiocyanate, a maleimide, a phosphoramidite, a reactive platinum complex, a sulfonyl halide, or a thiol group. As used herein, "reactive platinum complex" refers to chemically reactive platinum complexes such as described in U.S. Pat. No. 5,714,327, herein incorporated by reference in its entirety.

In certain embodiments, the compounds disclosed herein comprise at least one reactive group that selectively reacts with an amine group. This amine-reactive group is selected from the group consisting of succinimidyl ester (SE), sulfonyl halide, tetrafluorophenyl (TFP) ester, sulfodichlorophenyl (SDP) ester, sulfotetrafluorophenyl (STP) ester, pentafluorophenyl (PFP) ester and iosothiocyanates. Thus, in certain embodiments, the compounds provided herein form a covalent bond with an amine containing molecule in a sample. In certain embodiments, the compounds provided herein comprise at least one reactive group that selectively reacts with a thiol group. This thiol-reactive group is selected from the group consisting of maleimide, haloalkyl and haloacetamide (including any reactive groups disclosed in U.S. Pat. Nos. 5,362,628; 5,352,803 and 5,573,904, all of which are herein incorporated by reference in their entirety).

Where the reactive group is an activated ester of a carboxylic acid, such as a succinimidyl ester of a carboxylic acid, a sulfonyl halide, tetrafluorophenyl (TFP) ester, sulfodichlorophenyl (SDP) ester, sulfotetrafluorophenyl (STP) ester, pentafluorophenyl (PFP) ester or an isothiocyanate, the resulting compound is particularly useful for preparing conjugates of carrier molecules such as proteins, nucleotides, oligonucleotides, or haptens. Where the reactive group is a maleimide, haloalkyl or haloacetamide (including any reactive groups disclosed in U.S. Pat. Nos. 5,362,628; 5,352,803 and 5,573,904, all of which are herein incorporated by reference in their entirety) the resulting compound is particularly useful for conjugation to thiol-containing substances. Where the reactive group is a hydrazide, the resulting compound is particularly useful for conjugation to periodate-oxidized carbohydrates and glycoproteins, and in addition is an aldehyde-fixable polar tracer for cell microinjection. Where the reactive group is a silyl halide, the resulting compound is particularly useful for conjugation to silica surfaces, particularly where the silica surface is incorporated into a fiber optic probe subsequently used for remote ion detection or quantitation.

In a certain embodiments, the reactive group is a photoactivatable group such that the group is only converted to a reactive species after illumination with an appropriate wavelength. An appropriate wavelength is generally a UV wavelength that is less than 400 nm. This method provides for specific attachment to only the target molecules, either in solution or immobilized on a solid or semi-solid matrix. Photoactivatable reactive groups include, without limitation, benzophenones, aryl azides and diazirines.

Preferably, the reactive group is a photoactivatable group, succinimidyl ester of a carboxylic acid, a haloacetamide, haloalkyl, a hydrazine, an isothiocyanate, a maleimide group, an aliphatic amine, a silyl halide, a cadaverine or a psoralen. More preferably, the reactive group is a succinimidyl ester of a carboxylic acid, a maleimide, an iodoacetamide, or a silyl halide. In certain embodiments, the reactive group is a succinimidyl ester of a carboxylic acid, a sulfonyl halide, a tetrafluorophenyl ester, an iosothiocyanates or a maleimide. In certain embodiments, the reactive group is selected from sulfodichlorophenyl (SDP) ester, sulfotetrafluorophenyl (STP) ester, tetrafluorophenyl (TFP) ester, a pentafluorophenyl (PFP) ester, and a nitrilotriacetic acid (NTA).

Carrier Molecules:

In certain embodiments, the compounds provided herein are covalently bound to a carrier molecule. If the compound has a reactive group, then the carrier molecule may alternatively be linked to the compound through the reactive group. The reactive group may contain both a reactive functional moiety and a linker, or only the reactive functional moiety.

A variety of carrier molecules are useful herein. Exemplary carrier molecules include antigens, steroids, vitamins, drugs, haptens, metabolites, toxins, environmental pollutants, amino acids, peptides, proteins, nucleic acids, nucleic acid polymers, carbohydrates, lipids, polymers and bacterial particles. In certain embodiments, at least one member selected from $R^2$, $R^3$, $R^4$, $R^5$, $R^6$, $R^7$, $R^8$, $R^9$, $R^{10}$, $R^{12}$, $R^{13}$, $R^{19}$ and $R^{20}$ is a carrier molecule. In certain embodiments, at least one of $R^2$, $R^4$, $R^5$, $R^7$, $R^8$, $R^9$, $R^{10}$, $R^{12}$ and $R^{13}$ is a carrier molecule. In certain embodiments, at least one of $R^7$, $R^8$, $R^9$, $R^{10}$, $R^{12}$ and $R^{13}$ is a carrier molecule.

In certain embodiments, the carrier molecule comprises an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. In certain embodiments, the carrier molecule is selected from a hapten, a nucleotide, an oligonucleotide, a nucleic acid polymer, a protein, a peptide or a polysaccharide. In certain embodiments the carrier molecule is amino acid, a peptide, a protein, a polysaccharide, a nucleoside, a nucleotide, an oligonucleotide, a nucleic acid, a hapten, a psoralen, a drug, a hormone, a lipid, a lipid assembly, a tyramine, a synthetic polymer, a polymeric microparticle, a biological cell, cellular components, an ion chelating moiety, an enzymatic substrate or a virus. In certain embodiments, the carrier molecule is an antibody or fragment thereof, an antigen, an avidin or streptavidin, a biotin, a dextran, an IgG binding protein, a fluorescent protein, agarose, and a non-biological microparticle. In certain embodiments, carrier molecules may comprise a label or a fluorescent dye or quencher.

In certain embodiments, the carrier molecule is an amino acid (including those that are protected or are substituted by phosphates, carbohydrates, or $C_1$ to $C_{22}$ carboxylic acids), or a polymer of amino acids such as a peptide or protein. In certain embodiments, the carrier molecule contains at least five amino acids, more preferably 5 to 36 amino acids. Exemplary peptides include, but are not limited to, neuropeptides, cytokines, toxins, protease substrates, and protein kinase substrates. Other exemplary peptides may function as organelle localization peptides, that is, peptides that serve to target the conjugated compound for localization within a particular cellular substructure by cellular transport mechanisms. Preferred protein carrier molecules include enzymes, antibodies, lectins, glycoproteins, histones, albumins, lipoproteins, avidin, streptavidin, protein A, protein G, phycobiliproteins and other fluorescent proteins, hormones, toxins and growth factors. Typically, the protein carrier molecule is an antibody, an antibody fragment, avidin, streptavidin, a toxin, a lectin, a growth factor, bacterial particle or a binding partner for a cell receptor.

In certain embodiments, the carrier molecule comprises a nucleic acid base, nucleoside, nucleotide or a nucleic acid polymer, optionally containing an additional linker or spacer for attachment of a fluorophore or other ligand, such as an alkynyl linkage (U.S. Pat. No. 5,047,519), an aminoallyl linkage (U.S. Pat. No. 4,711,955) or other linkage. In certain embodiments, the nucleotide carrier molecule is a nucleoside or a deoxynucleoside or a dideoxynucleoside.

Exemplary nucleic acid polymer carrier molecules are single- or multi-stranded, natural or synthetic DNA or RNA oligonucleotides, or DNA/RNA hybrids, or incorporating an unusual linker such as morpholine derivatized phosphates (AntiVirals, Inc., Corvallis Oreg.), or peptide nucleic acids such as N-(2-aminoethyl)glycine units, where the nucleic acid contains fewer than 50 nucleotides, more typically fewer than 25 nucleotides.

In certain embodiments, the carrier molecule comprises a carbohydrate or polyol that is typically a polysaccharide, such as dextran, FICOLL (GE Healthcare), heparin, glycogen, amylopectin, mannan, inulin, starch, agarose and cellulose, or is a polymer such as a poly(ethylene glycol). In certain embodiments, the polysaccharide carrier molecule includes dextran, agarose or FICOLL. In certain embodiments, the carrier molecule includes a PEG group.

In certain embodiments, the carrier molecule comprises a lipid (typically having 6-25 carbons), including glycolipids, phospholipids, and sphingolipids. In certain embodiments, the carrier molecule comprises a lipid vesicle, such as a liposome, or is a lipoprotein. Some lipophilic substituents are useful for facilitating transport of the conjugated dye into cells or cellular organelles.

In certain embodiments, the carrier molecule is a cell, cellular system, cellular fragment, or subcellular particles, including virus particles, bacterial particles, virus components, biological cells (such as animal cells, plant cells, bacteria, or yeast), or cellular components. Examples of cellular components that are useful as carrier molecules include lysosomes, endosomes, cytoplasm, nuclei, histones, mitochondria, Golgi apparatus, endoplasmic reticulum and vacuoles.

In certain embodiments, the carrier molecule non-covalently associates with organic or inorganic materials. Exemplary embodiments of the carrier molecule that possess a lipophilic substituent may be used to target lipid assemblies such as biological membranes or liposomes by non-covalent incorporation of the compound within the membrane, e.g., for use as probes for membrane structure or for incorporation in liposomes, lipoproteins, films, plastics, lipophilic microspheres or similar materials.

In certain embodiments, the carrier molecule comprises a specific binding pair member wherein the compounds provided herein are conjugated to a specific binding pair member and used to the formation of the bound pair. Alternatively, the presence of the labeled specific binding pair member indicates the location of the complementary member of that specific binding pair; each specific binding pair member having an area on the surface or in a cavity which specifically binds to, and is complementary with, a particular spatial and polar organization of the other. In this instance, the dye compounds disclosed herein function as a reporter molecule for the specific binding pair. Exemplary binding pairs are set forth in Table 2.

TABLE 2

Representative Specific Binding Pairs

| Antigen | Antibody |
| --- | --- |
| biotin | avidin (or streptavidin or anti-biotin) |
| IgG* | protein A or protein G |
| drug | drug receptor |
| folate | folate binding protein |
| toxin | toxin receptor |
| carbohydrate | lectin or carbohydrate receptor |
| peptide | peptide receptor |
| protein | protein receptor |
| enzyme substrate | enzyme |
| DNA (RNA) | cDNA (cRNA)† |
| hormone | hormone receptor |
| ion | chelator |

*IgG is an immunoglobulin
†cDNA and cRNA are the complementary strands used for hybridization Solid Supports:

In certain embodiments, the compounds disclosed herein are covalently bonded to a solid support. The solid support may be attached to the compounds either through the aniline moiety, fluorophore, or through a reactive group, if present, or through a carrier molecule, if present. Even if a reactive group and/or a carrier molecule are present, the solid support may be attached through the aniline moiety or fluorophore. In certain embodiments, at least one member selected from $R^2$, $R^3$, $R^4$, $R^5$, $R^6$, $R^7$, $R^8$, $R^9$, $R^{10}$, $R^{12}$, $R^{13}$, $R^{19}$ and $R^{20}$ is a solid support. In certain embodiments, at least one of $R^2$, $R^4$, $R^5$, $R^7$, $R^8$, $R^9$, $R^{10}$, $R^{12}$ and $R^{13}$ is a solid support. In certain embodiments, at least one of $R^7$, $R^8$, $R^9$, $R^{10}$, $R^{12}$ and $R^{13}$ is a solid support.

Solid supports suitable for use herein are typically substantially insoluble in liquid phases. Solid supports for use herein are not limited to a specific type of support. Rather, a large number of supports are available and are known to one of ordinary skill in the art. Thus, useful solid supports include solid and semi-solid matrixes, such as aerogels and hydrogels, resins, beads, biochips (including thin film coated biochips), microfluidic chip, a silicon chip, multi-well plates (also referred to as microtitre plates or microplates), membranes, conducting and nonconducting metals, glass (including microscope slides) and magnetic supports. More specific examples of useful solid supports include silica gels, polymeric membranes, particles, derivatized plastic films, glass beads, cotton, plastic beads, alumina gels, polysaccharides such as SEPHAROSE (GE Healthcare), poly(acrylate), polystyrene, poly(acrylamide), polyol, agarose, agar, cellulose, dextran, starch, FICOLL (GE Healthcare), heparin, glycogen, amylopectin, mannan, inulin, nitrocellulose, diazocellulose, polyvinylchloride, polypropylene, polyethylene (including poly(ethylene glycol)), nylon, latex bead, magnetic bead, paramagnetic bead, superparamagnetic bead, starch and the like.

In certain embodiments, the solid support may include a solid support reactive functional group, including, but not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, etc., for attaching the dye compounds disclosed herein. Useful reactive groups are disclosed above and are equally applicable to the solid support reactive functional groups herein.

A suitable solid phase support may be selected on the basis of desired end use and suitability for various synthetic protocols. For example, where amide bond formation is desirable to attach the compounds disclosed herein to the solid support, resins generally useful in peptide synthesis may be employed, such as polystyrene (e.g., PAM-resin obtained from Bachem Inc., Peninsula Laboratories, etc.), POLYHIPE resin (obtained from Aminotech, Canada), polyamide resin (obtained from Peninsula Laboratories), polystyrene resin grafted with polyethylene glycol (TENTA-GEL, Rapp Polymere, Tubingen, Germany), polydimethylacrylamide resin (available from Milligen/Biosearch, California), or PEGA beads (obtained from Polymer Laboratories).

Preparation of Conjugates:

Another illustrative embodiment provides a process for preparing a conjugated compound of structural formula (I), (II), (III) or (IV) the process comprising:

reacting a compound of structural formula (I), (II), (III) or (IV) with a substance to be conjugated thereto, thereby resulting in a conjugated substance $S_C$.

The compounds disclosed herein that contain a reactive group $R_X$ are useful to fluorescently label a wide variety of organic substances that contain functional groups with suitable reactivity, resulting in chemical attachment, i.e., conjugation, of the substance (thereby affording a conjugated substance, $S_C$) and formation of compounds that are themselves conjugates. Most preferably, but not exclusively, the conjugated substance disclosed herein is an intracellular amino acid, peptide, protein, nucleotide, oligonucleotide, nucleic acid, lipid, phospholipid, lipoprotein, or lipopolysaccharide. The reactive group and functional group are typically an electrophile and a nucleophile, respectively, that can generate a covalent linkage. Alternatively, the reactive group is a photoactivatable group that becomes chemically reactive only after illumination with light of an appropriate wavelength. Selected examples of functional groups and linkages, where the reaction of an electrophilic group and a nucleophilic group yields a covalent linkage, as well as a general discussion of dye-conjugate chemistry, are provided in U.S. Pat. No. 5,830,912 the disclosure of which is incorporated herein by reference in its entirety.

In certain embodiments, conjugates of the compounds disclosed herein are provided. One or more of the compounds provided herein are conjugated to a biologically compatible polymer, including amino acid polymers (typically proteins, including IgG antibodies), carbohydrate polymers (typically dextrans), and polymeric microspheres (typically polystyrene) and are readily prepared for use as tracers according to methods known in the art.

Conjugates of components (carrier molecules or solid supports), e.g., drugs, peptides, toxins, nucleotides, phospholipids, proteins and other organic molecules are prepared by organic synthesis methods using the compounds disclosed herein, are generally prepared by means well recognized in the art (Haugland, MOLECULAR PROBES HANDBOOK, supra, (2002)). Preferably, conjugation to form a covalent bond consists of mixing the compounds disclosed herein in a suitable solvent in which both the compound and the substance to be conjugated are soluble. The reaction preferably proceeds spontaneously without added reagents at room temperature or below. For those reactive compounds that are photoactivated, conjugation is facilitated by illumination of the reaction mixture to activate the reactive compound. Chemical modification of water-insoluble substances, so that a desired compound-conjugate may be prepared, is preferably performed in an aprotic solvent such as dimethylformamide, dimethylsulfoxide, acetone, ethyl acetate, toluene, or chloroform. Similar modification of water-soluble materials is readily accomplished through the use of the instant reactive compounds to make them more readily soluble in organic solvents.

Preparation of peptide or protein conjugates typically comprises first dissolving the protein to be conjugated in aqueous buffer at about 1-10 mg/mL at room temperature or below. Bicarbonate buffers (pH about 8.3) are especially suitable for reaction with succinimidyl esters, phosphate buffers (pH about 7.2-8) for reaction with thiol-reactive functional groups and carbonate or borate buffers (pH about 9) for reaction with isothiocyanates and dichlorotriazines. The appropriate reactive compound is then dissolved in a nonhydroxylic solvent (usually DMSO or DMF) in an amount sufficient to give a suitable degree of conjugation when added to a solution of the protein to be conjugated. The appropriate amount of compound for any protein or other component is conveniently predetermined by experimentation in which variable amounts of the dye compound are added to the protein, the conjugate is chromatographically purified to separate unconjugated dye compound and the dye compound-protein conjugate is tested in its desired application.

Following addition of the compound to the component solution, the mixture is incubated for a suitable period (typically about 1 hour at room temperature to several hours on ice), the excess compound is removed by gel filtration, dialysis, HPLC, adsorption on an ion exchange or hydrophobic polymer or other suitable means. The dye compound-conjugate may be used in solution or lyophilized. In this way, suitable conjugates may be prepared from antibodies, antibody fragments, avidins, lectins, enzymes, proteins A and G, cellular proteins, albumins, histones, growth factors, hormones, and other proteins.

Conjugates of polymers, including biopolymers and other higher molecular weight polymers are typically prepared by means well recognized in the art (for example, Brinkley et al., *Bioconjugate Chem.*, 3:2 (1992)). In these embodiments, a single type of reactive site may be available, as is typical for polysaccharides) or multiple types of reactive sites (e.g. amines, thiols, alcohols, phenols) may be available, as is typical for proteins. Selectivity of labeling is best obtained by selection of an appropriate reactive dye compound. For example, modification of thiols with a thiol-selective reagent such as a haloacetamide or maleimide, or modification of amines with an amine-reactive reagent such as an activated ester, acyl azide, isothiocyanate or 3,5-dichloro-2,4,6-triazine. Partial selectivity may also be obtained by careful control of the reaction conditions.

When modifying polymers with the compounds disclosed herein, an excess of compound is typically used, relative to the expected degree of dye compound substitution. Any residual, unreacted compound or a compound hydrolysis product is typically removed by dialysis, chromatography or precipitation. Presence of residual, unconjugated compound may be detected by thin layer chromatography using a solvent that elutes the compound away from its conjugate. In all cases it is usually preferred that the reagents be kept as concentrated as practical so as to obtain adequate rates of conjugation.

In certain embodiments, the conjugates of the compounds disclosed herein are associated with an additional substance, that binds either to the fluorophore or the conjugated substance (carrier molecule or solid support) through non-covalent interaction. In another exemplary embodiment, the additional substance is an antibody, an enzyme, a hapten, a lectin, a receptor, an oligonucleotide, a nucleic acid, a liposome, or a polymer. The additional substance is optionally used to probe for the location of the conjugate, for example, as a means of enhancing the signal of the conjugate.

In certain embodiments, compositions are provided, the compositions comprising:
a) one or more of the compounds provided herein; and
b) a carrier.

In certain embodiments, compositions are provided, the compositions comprising:
a) one or more of the compounds provided herein; and
b) an analyte.

In certain embodiments, compositions are provided, the compositions comprising:
a) one or more of the compounds of structural formula (I), (II), (III) or (IV); and
b) a carrier,
wherein the one or more of the compounds are present in an amount effective to track cell proliferation, differentiation, and/or function.

In certain embodiments, compositions are provided, the compositions comprising:
(a) one or more of the compounds of structural formula (I), (II), (III) or (IV); and
(b) an analyte,
wherein the one or more of the compounds are present in an amount effective to track cell proliferation, differentiation, and/or function.

In certain embodiments, the analyte is a cell and the compound is located inside the cell. In certain embodiments, the compound is conjugated to a carrier molecule.

Methods:

Another embodiment provides a method for tracking cell proliferation, differentiation, and/or function, the method being compatible for use with, for example, flow cytometry and fluorescence microscopy, and comprising:
a) incubating a mixture of cells and a compound of structural formula (I):

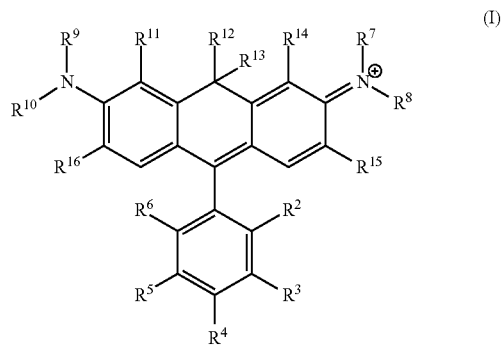

or a pharmaceutically acceptable salt thereof, wherein
$R^{12}$ and $R^{13}$ are each independently H, alkyl, substituted alkyl, or -L-$R_x$, or -L-$S_c$;
$R^2$, $R^3$, $R^4$, $R^5$, $R^6$, $R^7$, $R^8$, $R^9$, $R^{10}$, $R^{11}$, $R^{14}$, $R^{15}$, and $R^{16}$ are each independently H, halogen, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester) amino, (carboxyl ester) oxy, cyano, alkylcarboxylate, hydroxyl, nitro, sulfo, sulfoalkyl, substituted sulfoalkyl, sulfonyl, substituted sulfonyl, sulfonyloxy, thioacyl, thiol, alkylthiol, substituted alkylthiol, aryl, substituted aryl, heteroaryl, substituted heteroaryl, cycloalkyl, substituted cycloalkyl, heterocyclyl, substituted heterocyclyl, -L-$R_x$, or -L-$S_c$; or $R^7$ taken together with $R^{14}$ are part of an optionally substituted 5- or 6-membered ring;
$R^8$ taken together with $R^{15}$ are part of an optionally substituted 5- or 6-membered ring;
$R^9$ taken together with $R^{11}$ are part of an optionally substituted 5- or 6-membered ring;
$R^{10}$ taken together with $R^{16}$ are part of an optionally substituted 5- or 6-membered ring;
L is a linker;
$R_x$ is a reactive group; and
$S_c$ is a conjugated substance;
b) providing a stimulus to the mixture to elicit a fluorescent signal; and
c) analyzing the stimulated mixture.

In certain embodiments, $R^2$ is carboxyl, -L-$R_x$, or -L-$S_c$. In certain embodiments, $R^7$, $R^8$, $R^9$, and $R^{10}$ are each independently H, alkyl, substituted alkyl, or sulfoalkyl. In certain embodiments, $R^7$, $R^8$, $R^9$, and $R^{10}$ are each independently a $C_1$-$C_6$ alkyl, which can be the same or different. In certain embodiments, $R^7$, $R^8$, $R^9$, and $R^{10}$ are each methyl. In certain embodiments, $R^{12}$ and $R^{13}$ are each alkyl, preferably a $C_1$-$C_6$ alkyl. In certain embodiments, $R^{12}$ and $R^{13}$ are each methyl. In certain embodiments, $R^{11}$ and $R^{14}$ are each independently alkyl, substituted alkyl, sulfoalkyl, sulfo, -L-$R_x$, or -L-$S_c$. In certain embodiments, $R^{11}$ and $R^{14}$ are each independently a $C_1$-$C_6$ alkyl, a $C_1$-$C_6$ substituted alkyl, or sulfoalkyl, which can be the same or different. In certain embodiments, $R_x$ is succinimidyl ester (SE), sulfodichlorophenyl (SDP) ester, sulfotetrafluorophenyl (STP) ester, tetrafluorophenyl (TFP) ester, pentafluorophenyl (PFP) ester, nitrilotriacetic acid (NTA), aminodextran, and cyclooctyne-amine.

Another embodiment provides a method for tracking cell proliferation, differentiation, and/or function, the method being compatible for use with, for example, flow cytometry and fluorescence microscopy, and comprising:

a) incubating a mixture of cells and a compound of structural formula (II):

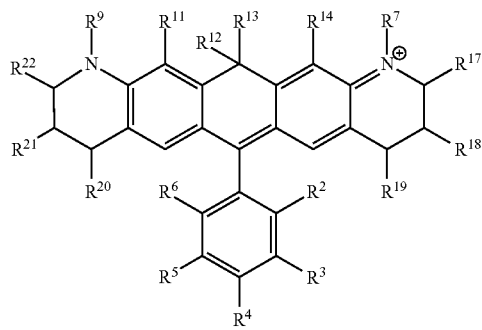

(II)

or a pharmaceutically acceptable salt thereof, wherein $R^{12}$ and $R^{13}$ are each independently H, alkyl, substituted alkyl, -L-$R_x$, or -L-$S_c$;

$R^2$, $R^3$, $R^4$, $R^5$, $R^6$, $R^7$, $R^9$, $R^{11}$, $R^{14}$, $R^{17}$, $R^{18}$, $R^{19}$, $R^{20}$, $R^{21}$ and $R^{22}$ are each independently H, halogen, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester) amino, (carboxyl ester) oxy, cyano, alkylcarboxylate, hydroxyl, nitro, sulfo, sulfoalkyl, substituted sulfoalkyl, sulfonyl, substituted sulfonyl, sulfonyloxy, thioacyl, thiol, alkylthiol, substituted alkylthiol, aryl, substituted aryl, heteroaryl, substituted heteroaryl, cycloalkyl, substituted cycloalkyl, heterocyclyl, substituted heterocyclyl, -L-$R_x$, or -L-$S_c$;

L is a linker;

$R_x$ is a reactive group; and $S_c$ is a conjugated substance;

b) providing a stimulus to the mixture to elicit a fluorescent signal; and c) analyzing the stimulated mixture.

In certain embodiments, $R^{12}$ and $R^{13}$ are each alkyl, preferably a $C_1$-$C_6$ alkyl. In certain embodiments, $R^{12}$ and $R^{13}$ are each methyl. In certain embodiments, $R^2$ is carboxyl, -L-$R_x$, or -L-$S_c$. In certain embodiments, $R^3$, $R^4$, $R^5$ and $R^6$ are each independently H or halo. In certain embodiments, $R^3$, $R^4$, $R^5$ and $R^6$ are independently H, Cl, or F. In certain embodiments, $R^7$ and $R^9$ are each independently alkyl, substituted alkyl, sulfoalkyl, sulfo, -L-$R_x$, or -L-$S_c$. In certain embodiments, $R^7$ and $R^9$ are each independently methyl, -L-$R_x$, -L-$S_c$ or $(CH_2)_n SO_3^-$, wherein n is an integer between 1 and 6. In certain embodiments, n is 3. In certain embodiments, $R_x$ is succinimidyl ester (SE), sulfodichlorophenyl (SDP) ester, sulfotetrafluorophenyl (STP) ester, tetrafluorophenyl (TFP) ester, pentafluorophenyl (PFP) ester, nitrilotriacetic acid (NTA), aminodextran, and cyclooctyne-amine.

Another embodiment provides a method for tracking cell proliferation, differentiation, and/or function, the method being compatible for use with, for example, flow cytometry and fluorescence microscopy, and comprising:

a) incubating a mixture of cells and a compound of structural formula (III):

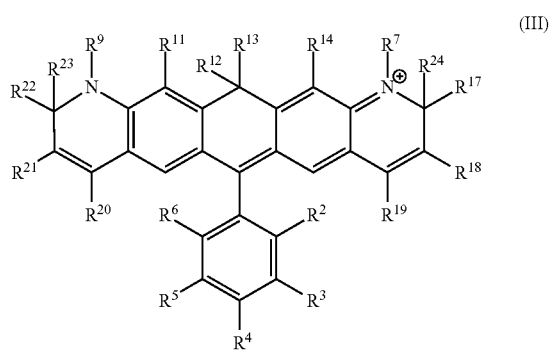

(III)

or a pharmaceutically acceptable salt thereof, wherein $R^{12}$ and $R^{13}$ are each independently H, alkyl, substituted alkyl, -L-$R_x$, or -L-$S_c$;

$R^2$, $R^3$, $R^4$, $R^5$, $R^6$, $R^7$, $R^9$, $R^{11}$, $R^{14}$, $R^{17}$, $R^{18}$, $R^{19}$, $R^{20}$, $R^{21}$, $R^{22}$, $R^{23}$ and $R^{24}$ are each independently H, halogen, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester) amino, (carboxyl ester) oxy, cyano, alkylcarboxylate, hydroxyl, nitro, sulfo, sulfoalkyl, substituted sulfoalkyl, sulfonyl, substituted sulfonyl, sulfonyloxy, thioacyl, thiol, alkylthiol, substituted alkylthiol, aryl, substituted aryl, heteroaryl, substituted heteroaryl, cycloalkyl, substituted cycloalkyl, heterocyclyl, substituted heterocyclyl, -L-$R_x$, or -L-$S_c$;

L is a linker;

$R_x$ is a reactive group; and $S_c$ is a conjugated substance;

b) providing a stimulus to the mixture to elicit a fluorescent signal; and c) analyzing the stimulated mixture.

In certain embodiments, $R^{12}$ and $R^{13}$ are each alkyl, preferably a $C_1$-$C_6$ alkyl. In certain embodiments, $R^{12}$ and $R^{13}$ are each methyl. In certain embodiments, $R^2$ is carboxyl, -L-$R_x$, or -L-$S_c$. In certain embodiments, $R^7$, $R^9$, $R^{17}$, $R^{19}$, $R^{20}$, $R^{22}$, $R^{23}$ and $R^{24}$ are each independently alkyl, substituted alkyl, sulfoalkyl, sulfo, -L-$R_x$, or -L-$S_c$. In certain embodiments, $R^7$, $R^9$, $R^{17}$, $R^{22}$, $R^{23}$ and $R^{24}$ are each methyl. In certain embodiments, $R^{19}$ and $R^{20}$ are each independently $(CH_2)_n SO_3^-$, wherein n is an integer between 1 and 6. In certain embodiments, n is 1. In certain embodiments, $R_x$ is succinimidyl ester (SE), sulfodichlorophenyl (SDP) ester, sulfotetrafluorophenyl (STP) ester, tetrafluorophenyl (TFP) ester, pentafluorophenyl (PFP) ester, nitrilotriacetic acid (NTA), aminodextran, and cyclooctyne-amine.

Another embodiment provides a method for tracking cell proliferation, differentiation, and/or function, the method being compatible for use with, for example, flow cytometry and fluorescence microscopy, and comprising:

a) incubating a mixture of cells and a compound of structural formula (IV):

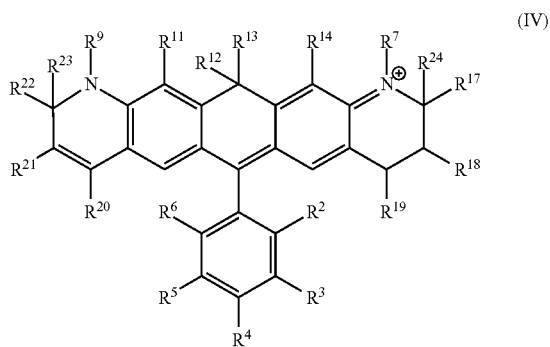

or a pharmaceutically acceptable salt thereof, wherein $R^{12}$ and $R^{13}$ are each independently H, alkyl, substituted alkyl, -L-$R_x$, or -L-$S_c$;

$R^2$, $R^3$, $R^4$, $R^5$, $R^6$, $R^7$, $R^9$, $R^{11}$, $R^{14}$, $R^{17}$, $R^{18}$, $R^{19}$, $R^{20}$, $R^{21}$, $R^{22}$, $R^{23}$ and $R^{24}$ are each independently H, halogen, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester) amino, (carboxyl ester) oxy, cyano, alkylcarboxylate, hydroxyl, nitro, sulfo, sulfoalkyl, substituted sulfoalkyl, sulfonyl, substituted sulfonyl, sulfonyloxy, thioacyl, thiol, alkylthiol, substituted alkylthiol, aryl, substituted aryl, heteroaryl, substituted heteroaryl, cycloalkyl, substituted cycloalkyl, heterocyclyl, substituted heterocyclyl, -L-$R_x$, or -L-$S_c$;

L is a linker;

$R_x$ is a reactive group; and $S_c$ is a conjugated substance;

b) providing a stimulus to the mixture to elicit a fluorescent signal; and c) analyzing the stimulated mixture.

In certain embodiments, $R^9$, $R^{12}$, $R^{13}$, $R^{22}$ and $R^{23}$ are each alkyl, preferably a $C_1$-$C_6$ alkyl. In certain embodiments, $R^9$, $R^{12}$, $R^{13}$, $R^{22}$ and $R^{23}$ are each methyl. In certain embodiments, $R^3$, $R^4$, $R^5$ and $R^6$ are each independently H or halo. In certain embodiments, $R^3$ and $R^6$ are independently H, Cl, or F. In certain embodiments, $R^2$ is carboxyl. In certain embodiments, $R^7$, $R^9$ and $R^{20}$ are each independently alkyl, substituted alkyl, sulfoalkyl, sulfo, $(CH_2)_nSO_3^-$, wherein n is an integer between 1 and 6, -L-$R_x$, or -L-$S_c$. In certain embodiments, $R^7$ is L-$R_x$ and $R^{20}$ is $(CH_2)_nSO_3^-$. In certain embodiments, n is 1. In certain embodiments, $R_x$ is succinimidyl ester (SE), sulfodichlorophenyl (SDP) ester, sulfotetrafluorophenyl (STP) ester, tetrafluorophenyl (TFP) ester, pentafluorophenyl (PFP) ester, nitrilotriacetic acid (NTA), aminodextran, and cyclooctyneamine.

In certain embodiments, $R_x$ is selected from an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, an imido ester, an isocyanate, an isothiocyanate, a maleimide, a phosphoramidite, a photoactivatable group, a reactive platinum complex, a silyl halide, a sulfonyl halide, and a thiol. In certain embodiments the reactive group is selected from the group consisting of carboxylic acid, succinimidyl ester of a carboxylic acid, hydrazide, amine and a maleimide. The reactive group may be attached to any appropriate site on the reporter molecule or the aniline moiety. In certain embodiments, at least one member selected from $R^2$, $R^3$, $R^4$, $R^5$, $R^6$, $R^7$, $R^8$, $R^9$, $R^{10}$, $R^{12}$, $R^{13}$, $R^{19}$ and $R^{20}$ is a reactive group. In certain embodiments, at least one of $R^2$, $R^4$, $R^5$, $R^7$, $R^8$, $R^9$, $R^{10}$, $R^{12}$ and $R^{13}$ is a reactive group. In certain embodiments, at least one of $R^7$, $R^8$, $R^9$, $R^{10}$, $R^{12}$ and $R^{13}$ is a reactive group.

In certain embodiments, $S_c$ is selected from a carrier molecule and a solid support. In certain embodiments, $S_c$ is selected from an amino acid, a polymer of amino acids, a peptide, a protein, a neurotoxin, a phallotoxin, a cytokine, a toxin, a protease substrate, a protein kinase substrate, an enzyme, an antibody, an antibody fragment, a lectin, a glycoprotein, a histone, an albumin, a lipoprotein, avidin, streptavidin, protein A, protein G, a phycobiliprotein, a fluorescent protein, a hormone, a growth factor, a nucleic acid base, a nucleoside, a nucleotide, a nucleic acid polymer, a nucleotide analog, a nucleoside analog, a nucleoside triphosphate, a deoxynucleoside triphosphate, a dideoxynucleoside triphosphate, a hapten, a carbohydrate, a polysaccharide, a lipid, an ion-complexing moiety (such as a crown ether), a PEG group, and an organic or inorganic polymer. In certain embodiments, at least one member selected from $R^2$, $R^3$, $R^4$, $R^5$, $R^6$, $R^7$, $R^8$, $R^9$, $R^{10}$, $R^{12}$, $R^{13}$, $R^{19}$ and $R^{20}$ is a conjugated substance. In certain embodiments, at least one of $R^2$, $R^4$, $R^5$, $R^7$, $R^8$, $R^9$, $R^{10}$, $R^{12}$ and $R^{13}$ is a conjugated substance. In certain embodiments, at least one of $R^7$, $R^8$, $R^9$, $R^{10}$, $R^{12}$ and $R^{13}$ is a conjugated substance. In certain embodiments, at least one of $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ is a PEG group.

In certain embodiments, the compounds used in the methods provided herein are selected from the group consisting of Compound 1, Compound 2, Compound 3, Compound 4, Compound 5, Compound 6, Compound 7, Compound 8, Compound 9, Compound 10, Compound 11, Compound 12, Compound 13, Compound 14, Compound 15, Compound 16, Compound 17, Compound 18, Compound 19, Compound 20, Compound 21, Compound 22, Compound 23, Compound 24, Compound 25 and amine-reactive forms thereof.

Another embodiment provides a method for determining cell health and/or cell viability, the method being compatible for use with, for example, flow cytometry and fluorescence microscopy, and comprising:

a) incubating a mixture of cells and a compound of structural formula (I):

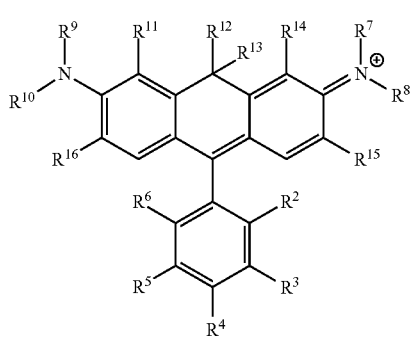

(I)

or a pharmaceutically acceptable salt thereof, wherein
$R^{12}$ and $R^{13}$ are each independently H, alkyl, substituted alkyl, or -L-$R_x$, or -L-$S_c$;
$R^2$, $R^3$, $R^4$, $R^5$, $R^6$, $R^7$, $R^8$, $R^9$, $R^{10}$, $R^{11}$, $R^{14}$, $R^{15}$, and $R^{16}$ are each independently H, halogen, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester) amino, (carboxyl ester) oxy, cyano, alkylcarboxylate, hydroxyl, nitro, sulfo, sulfoalkyl, substituted sulfoalkyl, sulfonyl, substituted sulfonyl, sulfonyloxy, thioacyl, thiol, alkylthiol, substituted alkylthiol, aryl, substituted aryl, heteroaryl, substituted heteroaryl, cycloalkyl, substituted cycloalkyl, heterocyclyl, substituted heterocyclyl, -L-$R_x$, or -L-$S_c$; or
$R^7$ taken together with $R^{14}$ are part of an optionally substituted 5- or 6-membered ring;
$R^8$ taken together with $R^{15}$ are part of an optionally substituted 5- or 6-membered ring;
$R^9$ taken together with $R^{11}$ are part of an optionally substituted 5- or 6-membered ring;
$R^{10}$ taken together with $R^{16}$ are part of an optionally substituted 5- or 6-membered ring;
L is a linker;
$R_x$ is a reactive group; and
$S_c$ is a conjugated substance;
b) providing a stimulus to the mixture to elicit a fluorescent signal; and
c) analyzing the stimulated mixture.
In certain embodiments, $R^2$ is carboxyl, -L-$R_x$, or -L-$S_c$. In certain embodiments, $R^7$, $R^8$, $R^9$, and $R^{10}$ are each independently H, alkyl, substituted alkyl, or sulfoalkyl. In certain embodiments, $R^7$, $R^8$, $R^9$, and $R^{10}$ are each independently a $C_1$-$C_6$ alkyl, which can be the same or different. In certain embodiments, $R^7$, $R^8$, $R^9$, and $R^{10}$ are each methyl. In certain embodiments, $R^{12}$ and $R^{13}$ are each alkyl, preferably a $C_1$-$C_6$ alkyl. In certain embodiments, $R^{12}$ and $R^{13}$ are each methyl. In certain embodiments, $R^{11}$ and $R^{14}$ are each independently alkyl, substituted alkyl, sulfoalkyl, sulfo, -L-$R_x$, or -L-$S_c$. In certain embodiments, $R^{11}$ and $R^{14}$ are each independently a $C_1$-$C_6$ alkyl, a $C_1$-$C_6$ substituted alkyl, or sulfoalkyl, which can be the same or different. In certain embodiments, $R_x$ is succinimidyl ester (SE), sulfodichlorophenyl (SDP) ester, sulfotetrafluorophenyl (STP) ester, tetrafluorophenyl (TFP) ester, pentafluorophenyl (PFP) ester, nitrilotriacetic acid (NTA), aminodextran, and cyclooctyne-amine.

Another embodiment provides a method for determining cell health and/or cell viability, the method being compatible for use with, for example, flow cytometry and fluorescence microscopy, and comprising:
a) incubating a mixture of cells and a compound of structural formula (II):

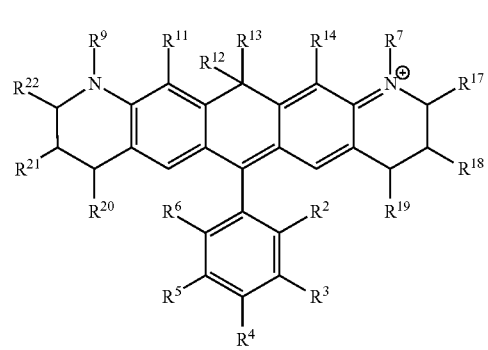

(II)

or a pharmaceutically acceptable salt thereof, wherein
$R^{12}$ and $R^{13}$ are each independently H, alkyl, substituted alkyl, -L-$R_x$, or -L-$S_c$;
$R^2$, $R^3$, $R^4$, $R^5$, $R^6$, $R^7$, $R^9$, $R^{11}$, $R^{14}$, $R^{17}$, $R^{18}$, $R^{19}$, $R^{20}$, $R^{21}$ and $R^{22}$ are each independently H, halogen, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester) amino, (carboxyl ester) oxy, cyano, alkylcarboxylate, hydroxyl, nitro, sulfo, sulfoalkyl, substituted sulfoalkyl, sulfonyl, substituted sulfonyl, sulfonyloxy, thioacyl, thiol, alkylthiol, substituted alkylthiol, aryl, substituted aryl, heteroaryl, substituted heteroaryl, cycloalkyl, substituted cycloalkyl, heterocyclyl, substituted heterocyclyl, -L-$R_x$, or -L-$S_c$;
L is a linker;
$R_x$ is a reactive group; and
$S_c$ is a conjugated substance;
b) providing a stimulus to the mixture to elicit a fluorescent signal; and
c) analyzing the stimulated mixture.
In certain embodiments, $R^{12}$ and $R^{13}$ are each alkyl, preferably a $C_1$-$C_6$ alkyl. In certain embodiments, $R^{12}$ and $R^{13}$ are each methyl. In certain embodiments, $R^2$ is carboxyl, -L-$R_x$, or L-$S_c$. In certain embodiments, $R^3$, $R^4$, $R^5$ and $R^6$ are each H or halo. In certain embodiments, $R^3$, $R^4$, $R^5$ and $R^6$ are independently H, Cl, or F. In certain embodiments, $R^7$ and $R^9$ are each independently alkyl, substituted alkyl, sulfoalkyl, sulfo, -L-$R_x$, or -L-$S_c$. In certain embodiments, $R^7$ and $R^9$ are each independently methyl, -L-$R_x$, -L-$S_c$ or $(CH_2)_nSO_3^-$, wherein n is an integer between 1 and 6. In certain embodiments, n is 3. In certain embodiments, $R_x$ is succinimidyl ester (SE), sulfodichlorophenyl (SDP) ester, sulfotetrafluorophenyl (STP) ester, tetrafluorophenyl (TFP) ester, pentafluorophenyl (PFP) ester, nitrilotriacetic acid (NTA), aminodextran, and cyclooctyne-amine.

Another embodiment provides a method for determining cell health and/or cell viability, the method being compatible for use with, for example, flow cytometry and fluorescence microscopy, and comprising:

a) incubating a mixture of cells and a compound of structural formula (III):

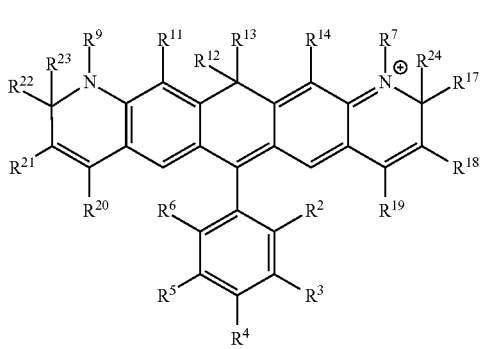

(III)

or a pharmaceutically acceptable salt thereof, wherein $R^{12}$ and $R^{13}$ are each independently H, alkyl, substituted alkyl, -L-$R_x$, or -L-$S_c$;

$R^2$, $R^3$, $R^4$, $R^5$, $R^6$, $R^7$, $R^9$, $R^{11}$, $R^{14}$, $R^{17}$, $R^{18}$, $R^{19}$, $R^{20}$, $R^{21}$, $R^{22}$, $R^{23}$ and $R^{24}$ are each independently H, halogen, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester) amino, (carboxyl ester) oxy, cyano, alkylcarboxylate, hydroxyl, nitro, sulfo, sulfoalkyl, substituted sulfoalkyl, sulfonyl, substituted sulfonyl, sulfonyloxy, thioacyl, thiol, alkylthiol, substituted alkylthiol, aryl, substituted aryl, heteroaryl, substituted heteroaryl, cycloalkyl, substituted cycloalkyl, heterocyclyl, substituted heterocyclyl, -L-$R_x$, or -L-$S_c$;

L is a linker;

$R_x$ is a reactive group; and $S_c$ is a conjugated substance;

b) providing a stimulus to the mixture to elicit a fluorescent signal; and c) analyzing the stimulated mixture.

In certain embodiments, $R^{12}$ and $R^{13}$ are each alkyl, preferably a $C_1$-$C_6$ alkyl. In certain embodiments, $R^{12}$ and $R^{13}$ are each methyl. In certain embodiments, $R^2$ is carboxyl, -L-$R_x$, or -L-$S_c$. In certain embodiments, $R^7$, $R^9$, $R^{17}$, $R^{19}$, $R^{20}$, $R^{22}$, $R^{23}$ and $R^{24}$ are each independently alkyl, substituted alkyl, sulfoalkyl, sulfo, -L-$R_x$, or -L-$S_c$. In certain embodiments, $R^7$, $R^9$, $R^{17}$, $R^{22}$, and $R^{24}$ are each methyl. In certain embodiments, $R^{19}$ and $R^{20}$ are each independently $(CH_2)_nSO_3^-$, wherein n is an integer between 1 and 6. In certain embodiments, n is 1. In certain embodiments, $R_x$ is succinimidyl ester (SE), sulfodichlorophenyl (SDP) ester, sulfotetrafluorophenyl (STP) ester, tetrafluorophenyl (TFP) ester, pentafluorophenyl (PFP) ester, nitrilotriacetic acid (NTA), aminodextran, and cyclooctyne-amine.

Another embodiment provides a method for determining cell health and/or cell viability, the method being compatible for use with, for example, flow cytometry and fluorescence microscopy, and comprising:

a) incubating a mixture of cells and a compound of structural formula (IV):

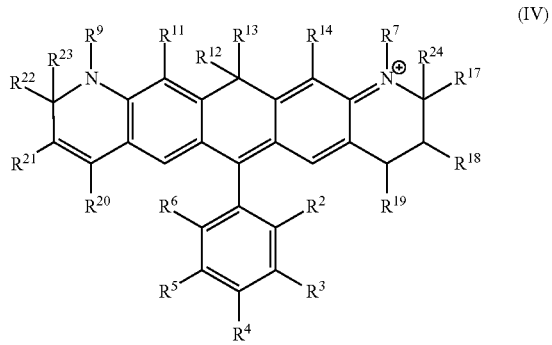

(IV)

or a pharmaceutically acceptable salt thereof, wherein $R^{12}$ and $R^{13}$ are each independently H, alkyl, substituted alkyl, -L-$R_x$, or -L-$S_c$;

$R^2$, $R^3$, $R^4$, $R^5$, $R^6$, $R^7$, $R^9$, $R^{11}$, $R^{14}$, $R^{17}$, $R^{18}$, $R^{19}$, $R^{20}$, $R^{21}$, $R^{22}$, $R^{23}$ and $R^{24}$ are each independently H, halogen, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester) amino, (carboxyl ester) oxy, cyano, alkylcarboxylate, hydroxyl, nitro, sulfo, sulfoalkyl, substituted sulfoalkyl, sulfonyl, substituted sulfonyl, sulfonyloxy, thioacyl, thiol, alkylthiol, substituted alkylthiol, aryl, substituted aryl, heteroaryl, substituted heteroaryl, cycloalkyl, substituted cycloalkyl, heterocyclyl, substituted heterocyclyl, -L-$R_x$, or -L-$S_c$;

L is a linker;

$R_x$ is a reactive group; and $S_c$ is a conjugated substance;

b) providing a stimulus to the mixture to elicit a fluorescent signal; and c) analyzing the stimulated mixture.

In certain embodiments, $R^9$, $R^{12}$, $R^{13}$, $R^{22}$ and $R^{23}$ are each alkyl, preferably a $C_1$-$C_6$ alkyl. In certain embodiments, $R^9$, $R^{12}$, $R^{13}$, $R^{22}$ and $R^{23}$ are each methyl. In certain embodiments, $R^3$, $R^4$, $R^5$ and $R^6$ are each independently H or halo. In certain embodiments, $R^3$ and $R^6$ are independently H, Cl, or F. In certain embodiments, $R^2$ is carboxyl. In certain embodiments, $R^7$, $R^9$ and $R^{20}$ are each independently alkyl, substituted alkyl, sulfoalkyl, sulfo, $(CH_2)_nSO_3^-$, wherein n is an integer between 1 and 6, -L-$R_x$, or -L-$S_c$. In certain embodiments, $R^7$ is -L-$R_x$ and $R^{20}$ is $(CH_2)_nSO_3^-$. In certain embodiments, n is 1. In certain embodiments, $R_x$ is succinimidyl ester (SE), sulfodichlorophenyl (SDP) ester, sulfotetrafluorophenyl (STP) ester, tetrafluorophenyl (TFP) ester, pentafluorophenyl (PFP) ester, nitrilotriacetic acid (NTA), aminodextran, and cyclooctyne-amine.

In certain embodiments, $R_x$ is selected from an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, an imido ester, an isocyanate, an isothiocyanate, a maleimide, a phosphoramidite, a photoactivatable group, a reactive platinum complex, a silyl halide, a sulfonyl halide, and a thiol. In certain embodiments the reactive group is selected from the group consisting of carboxylic acid, succinimidyl ester of a carboxylic acid, hydrazide, amine and a maleimide. The reactive group may be attached to any appropriate site on the reporter molecule or the aniline moiety. In certain embodiments, at least one member selected from $R^2, R^3, R^4, R^5, R^6, R^7, R^8, R^9, R^{10}, R^{12}, R^{13}, R^{19}$ and $R^{20}$ is a reactive group. In certain embodiments, at least one of $R^2, R^4, R^5, R^7, R^8, R^9, R^{10}, R^{12}$ and $R^{13}$ is a reactive group. In certain embodiments, at least one of $R^7, R^8, R^9, R^{10}, R^{12}$ and $R^{13}$ is a reactive group.

In certain embodiments, $S_c$ is selected from a carrier molecule and a solid support. In certain embodiments, $S_c$ is selected from an amino acid, a polymer of amino acids, a peptide, a protein, a neurotoxin, a phallotoxin, a cytokine, a toxin, a protease substrate, a protein kinase substrate, an enzyme, an antibody, an antibody fragment, a lectin, a glycoprotein, a histone, an albumin, a lipoprotein, avidin, streptavidin, protein A, protein G, a phycobiliprotein, a fluorescent protein, a hormone, a growth factor, a nucleic acid base, a nucleoside, a nucleotide, a nucleic acid polymer, a nucleotide analog, a nucleoside analog, a nucleoside triphosphate, a deoxynucleoside triphosphate, a dideoxynucleoside triphosphate, a hapten, a carbohydrate, a polysaccharide, a lipid, an ion-complexing moiety (such as a crown ether), a PEG group, and an organic or inorganic polymer. In certain embodiments, at least one member selected from $R^2, R^3, R^4, R^5, R^6, R^7, R^8, R^9, R^{10}, R^{12}, R^{13}, R^{19}$ and $R^{20}$ is a conjugated substance. In certain embodiments, at least one of $R^2, R^4, R^5, R^7, R^8, R^9, R^{10}, R^{12}$ and $R^{13}$ is a conjugated substance. In certain embodiments, at least one of $R^7, R^8, R^9, R^{10}, R^{12}$ and $R^{13}$ is a conjugated substance. In certain embodiments, at least one of $R^2, R^3, R^4, R^5, R^6, R^7, R^8, R^9, R^{10}, R^{11}, R^{12}, R^{13}, R^{14}, R^{15}$ and $R^{16}$ is a PEG group.

In certain embodiments, the compounds used in the methods provided herein are selected from the group consisting of Compound 1, Compound 2, Compound 3, Compound 4, Compound 5, Compound 6, Compound 7, Compound 8, Compound 9, Compound 10, Compound 11, Compound 12, Compound 13, Compound 14, Compound 15, Compound 16, Compound 17, Compound 18, Compound 19, Compound 20, Compound 21, Compound 22, Compound 23, Compound 24, Compound 25 and amine-reactive forms thereof.

In one illustrative embodiment, the method includes a second compound excitable at a different wavelength as the first compound. In another illustrative embodiment, the method includes a second compound where the second compound is selected from FAM-conjugated IgG or GFP.

In another illustrative embodiment of the method, step a) is conducted for approximately 20 minutes. In another illustrative embodiment, step b) and step c) are carried out concurrently. In another illustrative embodiment, step b) and step c) involve flow cytometry.

In addition to the methods described herein for tracking cell proliferation, differentiation, and/or function, the present disclosure also provides methods of using the compounds, including conjugates thereof, described herein to detect an analyte in a sample. Those of skill in the art will appreciate that this focus is for clarity of illustration and does not limit the scope of the methods in which the compounds disclosed herein find use.

The compounds provided herein can be used to stain biological samples, i.e. samples that comprise biological components. In one embodiment, the sample comprises heterogeneous mixtures of components, including intact cells, cell extracts, bacteria, viruses, organelles, and mixtures thereof. In another aspect, the sample comprises a single component or homogeneous group of components, e.g. biological polymers such as amino acid polymers, nucleic acid polymers or carbohydrate polymers, or lipid membrane complexes, whether the polymers are synthetic or natural.

The sample is typically stained by passive means, i.e., by incubation with a solution of a compound provided herein. Any other method of introducing the compound into the sample, such as microinjection of a solution containing the compound into a cell or organelle, can be used to accelerate introduction of the compound into the sample. The compounds provided herein are generally non-toxic to living cells and other biological components, within the concentrations of use.

In certain embodiments, the compounds disclosed herein are utilized to stain a sample to give a detectable optical response under desired conditions by a) preparing a dye solution comprising a compound described above, at a concentration sufficient to yield a detectable optical response under the desired conditions; combining the sample of interest with the dye solution for a period of time sufficient for the compound to yield a detectable optical response under the desired conditions; and c) illuminating the sample at a wavelength selected to elicit the optical response. Optionally, the sample is washed to remove residual, excess or unbound compound. The compound typically forms a covalent or non-covalent association or complex with an element of the sample, or is simply present within the bounds of the sample or portion of the sample.

The sample can be observed immediately after staining. The sample is optionally combined with other solutions in the course of staining, including wash solutions, permeabilization and/or fixation solutions, and other solutions containing additional detection reagents. Washing following staining generally improves the detection of the optical response due to the decrease in non-specific background fluorescence after washing. Satisfactory visualization is possible without washing by using lower labeling concentrations. A number of fixatives and fixation conditions suitable for practicing this invention are known in the art, including formaldehyde, paraformaldehyde, formalin, glutaraldehyde, cold methanol and 3:1 methanol:acetic acid. Fixation is typically used to preserve cellular morphology and to reduce biohazards when working with pathogenic samples. Selected embodiments of the compounds described above are well retained in cells, and sample cells stained with these compounds retain considerable fluorescent staining after fixation. Fixation is optionally followed or accompanied by permeabilization, such as with acetone, ethanol, DMSO or various detergents, to allow bulky compounds, including conjugates described above, to cross cell membranes, according to methods generally known in the art. The staining of the present disclosure is optionally combined with the use of an additional detection reagent that produces a detectable response due to the presence of a specific cell component, intracellular substance, or cellular condition, according to methods generally known in the art. Where the additional detection reagent has spectral properties that differ from those of the subject compounds, multi-color applications are possible.

The compounds provided herein are also of use to derivative low molecular weight compounds for their analysis by capillary zone electrophoresis (CZE), HPLC or other separation techniques.

In one embodiment, the staining is used to determine a specified characteristic of the sample by further comparing the optical response with a standard or expected response. For example, the dye solution is used to monitor specific components of the sample with respect to their spatial and temporal distribution in the sample. Alternatively, the dye preferentially binds to a specific analyte in a sample, enabling the researcher to determine the presence or quantity of that specific analyte. In another embodiment, the dye solution is used to analyze the sample for the presence of a mechanism that responds specifically to the compound, such as oxidation or reduction. The desired analysis to be performed determines the composition of the dye solution and chemical nature of the compound itself. In another example, the compound is bound by an antibody directed against the compound, typically resulting in the fluorescence quenching of the compound.

For biological applications, the dye solution is typically an aqueous or mostly aqueous solution that comprises one or more of the described compounds. In one aspect of the disclosure, the dye solution comprises a compound as described above; alternatively, the dye solution comprises a compound that is a reactive derivative of the compound, as previously described.

In yet another exemplary embodiment, the dye solution includes a conjugate of the compound as described above.

In yet another embodiment, a composition that includes a first conjugate of a compound described herein in combination with a second conjugate of a compound provided herein. The second conjugate includes a component that is covalently bonded to a second fluorophore. The first and second fluorophore have different structures and preferably fluoresce at different wavelengths. Even more preferably, the first and second fluorophores are selected so that their fluorescence emissions essentially do not overlap.

The fluorophore on the second conjugate can include substantially any fluorescent structure known in the art including, but not limited to, small organic fluorophores, fluorescent proteins, and reporter groups that are not necessarily fluorescent but which, under correct conditions, convert a fluorogenic substrate into a fluorophore, e.g., horseradish peroxidase. Exemplary second fluorophores of use herein include those that include a moiety that is a member selected from a coumarin, a xanthene (e.g., fluorescein), a cyanine, a pyrene, a borapolyazaindacene, an oxazine, and bimane.

The components of the mixture may be the same or a different molecule. The discussion herein pertaining to the identity of various components is generally applicable to this embodiment of the present disclosure.

In another exemplary embodiment, at least one of the first and second conjugates is bound to a molecule for which it is a binding partner.

The present disclosure also provides a method for detecting an analyte in a sample. The method includes contacting the sample with a conjugate of a compound provided herein in which the component is a binding partner for the analyte. The mixture of the conjugate and the analyte is incubated under any appropriate conditions for a length of time sufficient for at least a fraction of the analyte population to interact with the conjugate. The interaction can be by any known interaction mechanism, and the present disclosure is not limited to application with any single type of analyte-conjugate interaction mechanism. The interaction between the analyte and the compound conjugate results in the formation of a fluorescent analyte. The fluorescent analyte is readily detected and/or quantitated by irradiating it with light of a wavelength that causes the fluorescent analyte to emit fluorescence.

In the method described above, any number or combination of purification, separation or derivatization steps are optionally included as steps in the method. In an exemplary embodiment, the fluorescent analyte is separated from the remainder of the sample, from non-fluorescent analyte or from excess unbound conjugate prior to determining the fluorescence of the fluorescent analyte.

In another exemplary embodiment, the present disclosure provides a multicolor method for detecting an analyte or more than one analyte. For example, when it is desired to detect, and particularly to confirm the identity of an analyte, more than one fluorescent conjugate, preferably fluorescing at different wavelengths can be co-localized on the single analyte.

The use of more than one color of fluorescent conjugate per analyte provides assays in which specificity is dramatically increased, by requiring that the different colors or color combinations of the fluorescent conjugates coincide spatially during detection. This can dramatically reduce or even eliminate the detection of nonspecifically bound targets or labels, enhancing specificity and sensitivity of the assay. Underlying the improvement represented by the use of multiple differently colored fluorescent conjugates is the improbability of accidentally encountering two or more preselected different colors at the same location at the same time. The improbability increases as more fluorescent conjugates of different colors are used. Alternatively, in another exemplary embodiment, the emission from the two or more differently colored fluorescent conjugates combines to form a third color, which is not otherwise present in the assay.

In an exemplary application of the present method, different features of an analyte, e.g., a cell or epitopes of a molecule, are labeled with different colored fluorescent conjugates. The target is detected and its identity is confirmed using the colocalization or "coincidence" of each color on each target. Coincidence staining allows for the detection and differentiation of different organisms or strains of organisms expressing different surface markers. Moreover, coincidence staining provides a method of distinguishing molecules of different structure down to the level of isomeric differences and differences in stereochemistry.

In the detection of pathogenesis, the most direct analyte is the pathogenic organism itself. In this case, assays preferably identify particular features of the organism such as surface proteins. To further aid in characterization, it is preferred to assay for molecular analytes as well. An example of a molecular analyte is an exotoxin such as cholera toxin. Antigen specific binding receptors are generated that recognize different characteristics of an analyte with high specificity. In the case of molecular analytes, receptors recognize different epitopes of a protein or small molecule, while cellular analytes are recognized through different molecules on the cell surface.

Although the fluorescence from each conjugate can be detected simultaneously, in one embodiment, to facilitate coincidence staining, the fluorescence from each analyte is detected independently.

In another exemplary embodiment, colocalization is used to differentiate between the formation of an analyte-conjugate complex and non-specific binding of the analyte to another species within the assay system. The intrinsic sensitivity of an assay often is limited by non-specific binding of the analyte or other assay mixture components to the substrate. Single analyte coincidence staining can be used to differentiate between specific binding of the analyte to the conjugate and nonspecific binding of assay mixture components to the conjugate based on the colocalization of fluorescent conjugate colors. Those of skill in the art will appreciate that coincidence staining as described herein is useful to distinguish non-specific binding in both solid-phase (e.g., gene chip) and solution-based assays Coincidence staining can also be used to identify a single analyte. For example, one may wish to confirm the presence of a selected analyte in a mixture of analytes that are structurally similar (e.g. having a common epitope) or that have similar affinity for the component of the conjugate. In such circumstances, it may prove that the detection of a single epitope is not sufficient for conclusive identification of a target. Measuring the level of 2, preferably 3, more preferably 4 and even more preferably 5 or more markers within a single analyte, provides an unambiguous profile specific for the analyte of interest.

In another exemplary embodiment, the present disclosure provides a method for distinguishing between organisms expressing the same surface markers. Using coincidence staining, it is possible to identify differences in targets based on the ratio of surface marker expression. For example, despite intense efforts, no single binding-receptor has been found for the unambiguous detection of *B. anthracis* spores, due to extensive cross-reactivity with related *B. cereus* and *B. thuringiensis*, which are genetically a single species (Helgason et al., *Appl. Envir. Microbiol.* 66:2627-2630 (2000)). Despite being of the same species, however, the relative amount of various surface proteins is different between the three bacilli. Thus, multipoint detection of a variety of markers at the single cell level will provide the specificity required to detect *B. anthracis.*

Diagnostic tests that detect the presence or absence of a single marker are unable to distinguish among strains that are nearly identical at the genetic level, highlighting the need for new tools to distinguish between closely related organisms. Epidemics caused by emerging variants of known pathogens are a common theme in infectious diseases (Jiang et al., *Appl Environ Microbiol* 66: 148-53 (2000)) (Hedelberg et al. *Nature* 406:477-483 (2000)). There is also the problem of deliberate engineering of pathogens, incorporating virulence determinants from other species. An attack by such pathogens would be misdiagnosed due to the presence of markers not normally found in the attacking pathogen. By probing multiple markers within a single organism, using the methods provided herein, such variants are detected and preferably identified.

Detection by eye is also useful in those embodiments that rely on coincidence staining. The human eye is extremely good at distinguishing between subtly different combinations of colors, especially when the colors are chosen correctly. By way of illustration, it is trivial for people to distinguish between the colors red, green and yellow. Yellow, however, is simply the spectral sum of red and green, so if red and green fluorescent conjugates are used for coincidence staining, positive assay signal can easily be identified by the perceived color, yellow. Other color combinations of use in this embodiment of the disclosure will be readily apparent to those of skill in the art, such as combinations of red, green and blue to form white.

In another exemplary embodiment, the present disclosure provides a method for detecting a first analyte and a second analyte in a sample. The method includes incubating the sample with a compound provided herein that includes first and second fluorescent labeled conjugates. The component of the first conjugate is a binding partner for the first analyte and the component of the second conjugate is a binding partner for the second analyte. The incubation continues for a time and under conditions appropriate to induce an interaction between at least a fraction of the population of the first analyte with the first conjugate. During this incubation period, it is generally preferred that a similar interaction occurs between the second analyte and second conjugate, however, it is within the scope of the present disclosure to change the incubation conditions as necessary to drive the formation of a conjugate-analyte complex between the second conjugate and second analyte.

Following the formation of at least the first analyte-conjugate complex, the sample is illuminated with light of a wavelength appropriate to cause the complex to fluoresce, thereby detecting the first analyte. The second analyte is detected in a similar manner and may be detected simultaneously with the first analyte or by the sequential illumination of the sample with wavelengths appropriate to induce the fluorescence of each fluorescent conjugate.

Solutions of the compounds provided herein are prepared according to methods generally known in the art. As with related known fluorophores and fluorogens, the compounds and conjugates of the compounds provided herein are generally soluble in water and aqueous solutions having a pH greater than or equal to about 6. Stock solutions of pure dyes, however, are typically dissolved in organic solvent before diluting into aqueous solution or buffer. Preferred organic solvents are aprotic polar solvents such as DMSO, DMF, N-methylpyrrolidone, acetone, acetonitrile, dioxane, tetrahydrofuran and other nonhydroxylic, completely water-miscible solvents. In general, the amount of the compound or conjugate of the compound in the dye solution is the minimum amount required to yield detectable staining in the sample within a reasonable time, with minimal background fluorescence or undesirable staining. The exact concentration of the compound or conjugate of the compound to be used is dependent upon the experimental conditions and the desired results, and optimization of experimental conditions is typically required to determine the best concentration of stain to be used in a given application. The concentration of the compound present in the dye solution typically ranges from nanomolar to micromolar. The required concentration for the dye solution is determined by systematic variation in the concentration of the compound or conjugate of the compound until satisfactory staining is accomplished. The starting ranges are readily determined from methods known in the art for use of similar compounds under comparable conditions for the desired optical response.

For those compounds of the present disclosure that are lipophilic in nature, the compound is optionally introduced into living cells by passive permeation through the cellular membranes. Less cell-permeant compounds provided herein can be introduced into cells by pressure microinjection methods, scrape loading techniques (short mechanical disruption of the plasma membrane where the plasma membrane is peeled away from the cytoplasm, the compound is perfused through the sample and the plasma membrane is reassembled), patch clamp methods (where an opening is maintained in the plasma membrane for long periods) or phagocytosis. Any other treatment that will permeabilize the plasma membrane, such as electroporation, shock treatments or high extracellular ATP can be used to introduce the compound, conjugate of the compound, or blocked compound into the cellular cytoplasm.

In an exemplary embodiment, the dye solution comprises a compound that non-covalently associates with organic or inorganic materials. Exemplary embodiments of the compounds that possess a lipophilic substituent can be used to stain lipid assemblies such as biological membranes or liposomes by non-covalent incorporation of the compound within the membrane, e.g. for use as probes for membrane structure or for incorporation in liposomes, lipoproteins, films, plastics, lipophilic microspheres or similar materials.

The compounds provided herein are useful as coloring agents, tracers for detecting the flow of fluids such as in angiography, and tracing of fluid flow through gap junctions of neurons according to procedures known in the art for other dyes. The compounds provided herein are also useful in assays as haptens, according to known methods, wherein the compound is recognized by an anti-compound antibody.

Reactive versions of the compounds provided herein can be used to label cell surfaces, cell membranes or intracellular compartments such as organelles, or in the cell's cytoplasm. Certain reactive groups allow the retention of the compound in cells or organelles by reacting with cellular materials. In particular, haloalkyl- or halomethylbenzamide-substituted fluorophores are used to react selectively with intracellular components such as glutathione, or to retain the compounds within cells or within selected organelles where the compound is localized therein, according to methods previously described (U.S. Pat. No. 5,362,628 to Haugland et al, (1994); U.S. Pat. No. 5,576,424 to Mao et al. (1996) (in cells); and U.S. Pat. No. 5,459,268 to Haugland et al. (1995) and U.S. Pat. No. 5,686,261 to Zhang et al. (1997) (in mitochondria); all incorporated by reference). Polyfluoroaryl-substituted compounds are similarly retained in cells, in part by covalent attachment. The reactive compounds are used to localize staining in a part of the sample, e.g., where the localization of the corresponding functional group is indicative of a characteristic of the sample; or to retain the compound in a specific portion of the sample for extended periods of time, e.g., to follow the stained portion of the sample through a period of time or sequence of events. Alternatively, the compounds are used according to this method to make conjugates, as described above, which are separately useful for staining.

In an exemplary embodiment in which the dye solution comprises a conjugate of the compound, the conjugate is a labeled member of a specific binding pair, and is used as a fluorescent probe for the complementary member of that specific binding pair, each specific binding pair member having an area on the surface or in a cavity which specifically binds to and is complementary with a particular spatial and polar organization of the other. The fluorescent conjugate of a specific binding pair member is useful for detecting and optionally quantifying the presence of the complementary specific binding pair member in a sample, by methods that are well known in the art. Optionally, the complementary binding pair member is present in an animal cell, plant cell, bacteria, yeast or virus. Alternatively, the complementary member is immobilized on a solid or semi-solid surface, such as a polymer, polymeric membrane or polymeric particle (such as a polymeric bead). The conjugate of the compound may also comprise a compound in a blocked form wherein the block is later removed by the action of an enzyme or light.

Representative specific binding pairs are shown in Table 2. Typically a specific binding pair member conjugated to the compound is a ligand or a receptor. As used herein, the term ligand means any organic compound for which a receptor naturally exists or can be prepared. A receptor is any compound or composition capable of recognizing a spatial or polar organization of a molecule, e.g. epitopic or determinant site. Ligands for which naturally occurring receptors exist include natural and synthetic proteins, including avidin and streptavidin, antibodies, enzymes, and hormones; nucleotides and natural or synthetic oligonucleotides, including primers for RNA and single- and double-stranded DNA; lipids; polysaccharides and carbohydrates; and a variety of drugs, including therapeutic drugs and drugs of abuse and pesticides. The compounds provided herein are used according to methods extensively known in the art, to prepare antibody conjugates for use in microscopy and immunofluorescent assays and nucleotide or oligonucleotide conjugates for nucleic acid hybridization assays and nucleic acid sequencing (e.g., U.S. Pat. No. 5,332,666 to Prober, et al. (1994); U.S. Pat. No. 5,171,534 to Smith, et al. (1992); U.S. Pat. No. 4,997,928 to Hobbs (1991); and PCT International Application Publication No. WO 94/05688 to Menchen, et al.) and a wide variety of other applications. Nucleotide conjugates are readily incorporated by DNA polymerase and can be used for in situ hybridization or other techniques.

In another preferred embodiment, the compounds described herein are utilized as a component of one or more probes used in a multiplex assay for detecting one or more species in a mixture. As used herein, the term "multiplex assay" refers to an assay in which fluorescence from two or more dyes is detected, or in which fluorescence energy transfer between two or more dyes and one or more quencher is detected.

Probes that include a compound of the present disclosure are particularly useful in performing multiplex-type analyses and assays. In a typical multiplex analysis, two or more distinct species (or regions of one or more species) are detected using two or more probes, wherein each of the probes is labeled with a different fluorophore. Preferred species used in multiplex analyses generally meet at least two criteria: the fluorescent species is bright and spectrally well resolved; and the background fluorescence of the first dye does not significantly overlap the emission range of the second dye.

Thus, in a further embodiment, the present disclosure provides a mixture comprising at least a first and a second compound provided herein. The first and second compounds are preferably conjugated to a component of a conjugate. The compounds may be conjugated to the same component or to different components.

The compounds provided herein allow for the design of multiplex assays in which more than one compound is used in the assay. A number of different multiplex assays using the compounds provided herein will be apparent to one of skill in the art. In one exemplary assay, each of the at least two distinct dyes are detected. Alternatively, an assay can be practiced in which each distinct compound transfers energy to a distinct quencher to which the compound is "matched." The fluorophores can be bound to the same molecule as the quencher or to a different molecule. Moreover, similar to the dyes and the quenchers, the component of the different conjugates of use in a particular assay system can be the same or different.

In addition to the mixtures described above, the present disclosure also provides a method for detecting or quantifying a particular molecular species. The method includes: (a) contacting the species with a mixture such as that described above; and (b) detecting a change in a fluorescent property of one or more component of the mixture, the molecular species or a combination thereof, thereby detecting or quantifying the molecular species.

The simultaneous use of two or more probes using donor-acceptor energy transfer is known in the art. For example, multiplex assays using nucleic acid probes with different sequence specificities have been described. Fluorescent probes have been used to determine whether an individual is homozygous wild-type, homozygous mutant or heterozygous for a particular mutation. For example, using one quenched-fluorescein molecular beacon that recognizes the wild-type sequence and another rhodamine-quenched molecular beacon that recognizes a mutant allele, it is possible to genotype individuals for the β-chemokine receptor (Kostrikis et al. Science 279:1228-1229 (1998)). The presence of only a fluorescein signal indicates that the individual is wild-type, and the presence of rhodamine signal only indicates that the individual is a homozygous mutant. The presence of both the rhodamine and fluorescein signal is diagnostic of a heterozygote. Tyagi et al. *Nature Biotechnology* 16: 49-53 (1998)) have described the simultaneous use of four differently labeled molecular beacons for allele discrimination, and Lee et al., *BioTechniques* 27: 342-349 (1999) have described seven color homogenous detection of six PCR products.

The compounds provided herein can be used in multiplex assays designed to detect and/or quantify substantially any species, including, for example, whole cells, viruses, proteins (e.g., enzymes, antibodies, receptors), glycoproteins, lipoproteins, subcellular particles, organisms (e.g., *Salmonella*), nucleic acids (e.g., DNA, RNA, and analogues thereof), polysaccharides, lipopolysaccharides, lipids, fatty acids, non-biological polymers and small molecules (e.g., toxins, drugs, pesticides, metabolites, hormones, alkaloids, steroids).

The compounds of the present disclosure are also of use in the numerous fluorescence polarization assays that use conjugates of fluorescent dyes to low molecular weight drugs and ligands, which will be improved by the use of the dye compounds of the invention, e.g., U.S. Pat. No. 4,420,568 to Wang (1983) and U.S. Pat. No. 4,510,251 to Kirkemo et al. (1985).

In those embodiments in which a compound is conjugated to a specific binding pair member that is a chelator of calcium, sodium, magnesium, potassium, or other biologically important metal ion, the conjugate of the compound functions as an indicator of the ion, which indicators are optionally further conjugated to a biological or plastic polymer according to methods known in the art; e.g., using analogs of the compounds described in U.S. Pat. No. 5,453,517 to Kuhn, et al. (1995); U.S. Pat. No. 5,405,975 to Kuhn, et al. (1995). Alternatively, the compound itself acts as a pH indicator at pH values within about 1.5 pH units of the individual compound's pKa. Typically the detectable optical response of the ion indicators is a change in fluorescence.

In another exemplary embodiment, the compounds provided herein are substrates for enzymes, such as caspases, oxidases and other reactive oxidizing agents, such as peroxidase enzymes.

Polypeptides may be conjugated, or "labeled", with labeling reagents to prepare the peptide conjugates provided herein. Peptides, proteins, antibodies, and other biopolymers comprised of amino acids and amino acid analogs may be covalently labeled by conjugation with the compounds provided herein. Typically, the compounds bear an electrophilic linking moiety which reacts with a nucleophilic group on the peptide, e g amino terminus, or side-chain nucleophile of an amino acid. Alternatively, the compound may be in nucleophilic form, e.g. amino- or thiol-linking moiety, which reacts with an electrophilic group on the peptide, e.g. NHS of the carboxyl terminus or carboxyl side-chain of an amino acid. The polypeptide may be on a solid support, i.e. synthesis resin, during the labeling reaction. Alternatively, the polypeptide may have been cleaved prior to labeling. By appropriate selection of protecting groups, certain reactive functionality on the peptide can be selectively unmasked for reaction with a labeling reagent.

The compound label reagents include a reactive linking group, "linking moiety", at one of the substituent positions for covalent attachment of the compound to a polypeptide. Linking moieties capable of forming a covalent bond are typically electrophilic functional groups capable of reacting with nucleophilic molecules, such as alcohols, alkoxides, amines, hydroxylamines, and thiols. Examples of electrophilic linking moieties include succinimidyl ester, isothiocyanate, sulfonyl chloride, sulfonate ester, silyl halide, 2,6-dichlorotriazinyl, pentafluorophenyl ester, phosphoramidite, maleimide, iodoacetamide, haloacetyl, epoxide, alkylhalide, allyl halide, aldehyde, ketone, acylazide, and anhydride.

One linking moiety is an N-hydroxysuccinimidyl ester (NHS) of a carboxyl group substituent on a compound provided herein. The NHS ester form of the compound is an exemplary labeling reagent. Another preferred linking moiety is a phosphoramidite reagent of the dyes provided herein. Phosphoramidite dye reagents are particularly useful for labeling of polypeptides by automated synthesis on solid support. Oligonucleotides are commonly synthesized on solid supports by the phosphoramidite method (Caruthers, U.S. Pat. No. 4,415,732; Caruthers, U.S. Pat. No. 4,458,066; Beaucage, *Tetrahedron* 48:2223-2311 ((1992)).

Peptide conjugates of the present disclosure are labeled with a compound provided herein. The compound provides a detection element for localizing, visualizing, and quantitating the cleavage event. The properties of the compound also facilitate transport through the cell membrane and targeting of intracellular structures and molecules. Upon cleavage of the peptide by a peptidase or protease, such as a caspase, a detectable increase in fluorescence from the compound may be measured. The peptide conjugates provided herein retain the specific binding and recognition properties of the respective compound and peptide sequence.

For example, in Scheme 1 a compound of the present disclosure that is bound to a peptide(s) is non-fluorescent; however, upon cleavage of the recognition site by a protease results in fluorescence of the released dye compound.

Scheme 1:

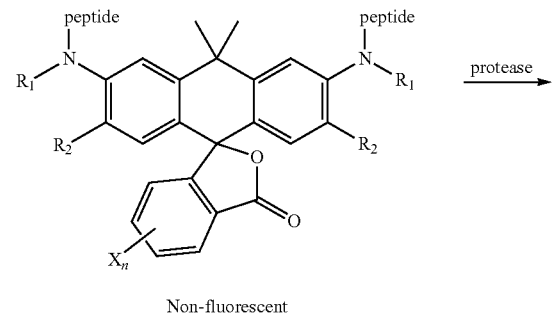

Non-fluorescent

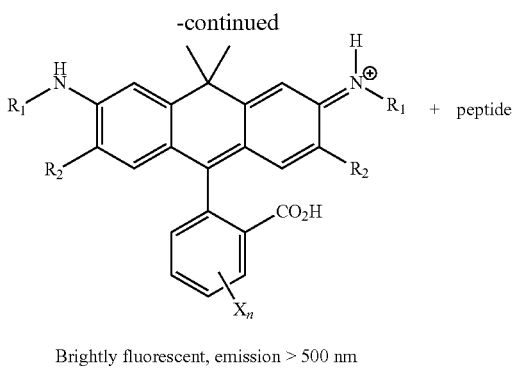

Brightly fluorescent, emission > 500 nm

Certain polypeptide sequences of peptide conjugates are substrates for caspase enzymes. A protease binding site is an amino acid sequence (polypeptide) which is recognized and cleaved by a particular protease. Caspases are known to cleave polypeptide substrates adjacent to particular amino acids within a recognition site. A particular caspase does not cleave every bond in a substrate that has any particular amino acid. Rather, caspases are specific to particular amino acid sequences which serve as recognition domains for each particular caspase. Any polypeptide that comprises the DEVD (SEQ ID NO: 1) caspase recognition site can be a peptide conjugate of the present disclosure. In this recognition site, the cleavage site is the amide bond between the aspartic acid residue toward the carboxyl terminus and the adjacent amine group. (For example, see Scheme 2).

Scheme 2 ("DEVD" disclosed as SEQ ID NO: 1):

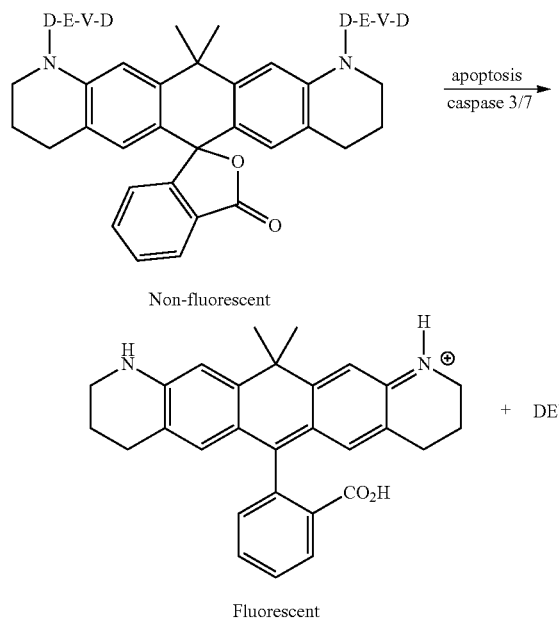

The enzyme substrates optionally contain additional substituents that provide additional advantages. For example, fluorophores modified to contain a lipophilic tail according to the synthesis described in U.S. Pat. No. 5,208,148 to Haugland et al. (1993), are useful for permeabilizing substrates for intracellular enzymes.

In another exemplary embodiment, the compounds provided herein are used to determine the efficiency of a cellular efflux pump of cells in a sample. Preferably the compounds are diacetates or diphosphates. The compound is used in the minimum concentration that gives a detectable fluorescence emission. Once the diacetate compounds are inside the cell, the blocking acetates are cleaved and the compound becomes highly fluorescent. The efficiency of the cellular efflux pump of cells in the sample is determined by comparing the fluorescence emission of cells in the sample with the fluorescence of cells having known efflux efficiency. Where the efflux pump is impaired, inhibited, or absent, the fluorescent compound is well retained in the cell; where the efflux pump is present and functioning, the fluorescence of the cells decreases markedly. The photostability of the present compounds is advantageous for monitoring the time course of fluorescence.

Illumination

At any time after or during an assay or staining procedure, the sample is illuminated with a wavelength of light that results in a detectable optical response, and observed with a means for detecting the optical response. While the compounds are detectable colorimetrically, using ambient light, typically the compounds are detected by the fluorescence properties of the parent fluorophore. Upon illumination, such as by an ultraviolet or visible wavelength emission lamp, an arc lamp, a laser, or even sunlight or ordinary room light, the compounds, including compounds bound to the complementary specific binding pair member, display intense visible absorption as well as fluorescence emission. Selected equipment that is useful for illuminating the conjugates of the present disclosure includes, but is not limited to, hand-held ultraviolet lamps, mercury arc lamps, xenon lamps, argon lasers, laser diodes, and YAG lasers. These illumination sources are optionally integrated into laser scanners, fluorescence microplate readers, standard or mini fluorometers, or chromatographic detectors. This colorimetric absorbance or fluorescence emission is optionally detected by visual inspection, or by use of any of the following devices: CCD cameras, video cameras, photographic film, laser scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, a fluorescence microscope or a fluorometer, the instrument is optionally used to distinguish and discriminate between the compound and a second fluorophore with detectably different optical properties, typically by distinguishing the fluorescence response of the conjugate from that of the second fluorophore. Where the sample is examined using a flow cytometer, examination of the sample optionally includes isolation of particles within the sample based on the fluorescence response of the dye compound by using a sorting device.

A detectable optical response means a change in, or occurrence of, a parameter in a test system that is capable of being perceived, either by direct observation or instrumentally. Such detectable responses include the change in, or appearance of, color, fluorescence, reflectance, chemiluminescence, light polarization, light scattering, or x-ray scattering. Typically the detectable response is a change in fluorescence, such as a change in the intensity, excitation or emission wavelength distribution of fluorescence, fluorescence lifetime, fluorescence polarization, or a combination thereof. The detectable optical response may occur throughout the sample or in a localized portion of the sample. The presence or absence of the optical response after the elapsed time is indicative of one or more characteristic of the sample. Comparison of the degree of staining with a standard or expected response can be used to determine whether and to what degree the sample possesses a given characteristic.

Sample Preparation

The end user will determine the choice of the sample and the way in which the sample is prepared. The sample includes, without limitation, any biological derived material or aqueous solution. The sample can be a biological fluid such as whole blood, plasma, serum, nasal secretions, sputum, saliva, urine, sweat, transdermal exudates, cerebrospinal fluid, or the like. Biological fluids also include tissue and cell culture medium wherein an analyte of interest has been secreted into the medium. Alternatively, the sample may be whole organs, tissue or cells from the animal. Examples of sources of such samples include muscle, eye, skin, gonads, lymph nodes, heart, brain, lung, liver, kidney, spleen, thymus, pancreas, solid tumors, macrophages, mammary glands, mesothelium, and the like. Cells include without limitation prokaryotic cells and eukaryotic cells that include primary cultures and immortalized cell lines. Eukaryotic cells include without limitation ovary cells, epithelial cells, circulating immune cells, 13 cells, hepatocytes, and neurons.

When the compounds provided herein are used as components of an assay system for a target species in a mixture, such as an enzyme, the target concentration is conveniently in the range of about 1 nM to 500 nM, more usually in the range of about 25 to 250 nM. One may use an individual compound provided herein, multiple compounds provided herein or a combination of a compound provided herein and a fluorophore or quencher of a different structure in order to detect the presence of or determine the characteristics of a target in a sample.

When the components of the present disclosure are species that bind to targets that are specific biological structures (e.g., enzymes, receptors, ligands, antigens, antibodies, etc.), the reaction time between the compound or conjugate provided herein and the target will usually be at least about 5 min, more usually at least about 30 min and preferably not more than about 180 min, preferably not more than about 120 min, depending upon the temperature, concentrations of enzyme and substrate, etc. By using a specific time period for the reaction or taking aliquots at 2 different times, the rate of reaction can be determined for comparison with other determinations. The temperature will generally be in the range of about 20 to 50° C., more usually in the range of about 25 to 40° C.

If the assay focuses on an enzyme, coenzyme, if any, is preferably present in excess, so as not be rate limiting. Generally, with the concentrations of enzyme indicated above, the concentration of coenzyme will be at least about 0.1 mM, usually at least about 1 mM and not more than about 25 mM. The coenzyme solution should be prepared freshly for each series of determinations.

Various buffers can be used in the assays provided herein. These buffers include PBS, Tris, MOPS, HEPES, phosphate, etc. The pH will vary depending upon the particular assay system, generally within a readily determinable range wherein one or more of the sulfonic acid moieties is deprotonated. The concentration of buffer is generally in the range of about 0.1 to 50 mM, more usually 0.5 to 20 mM.

In certain instances, it may be advantageous to add a small amount of a non-ionic detergent to the sample. Generally the detergent will be present in from about 0.01 to 0.1 vol. %.

Illustrative non-ionic detergents include the polyoxyalkylene diols, e.g. PLURONICS (BASF), TWEENs (Croda International, PLC), TRITON X-100 (Dow Pharmaceuticals), etc.

After sufficient time for a detectable amount of product to form, the reaction is optionally quenched. Various quenching agents may be used, both physical and chemical. Conveniently, a small amount of a water-soluble inhibitor may be added, such as acetonitrile, DMSO, SDS, methanol, DMF, etc. The amount of inhibitor will vary with the nature of the inhibitor and may be determined empirically.

Kits:

Another embodiment provides a kit for tracking cell proliferation, differentiation and/or function, the kit being compatible for use with, for example, flow cytometry and fluorescence microscopy, and comprising:

a) a compound of structural formula (I):

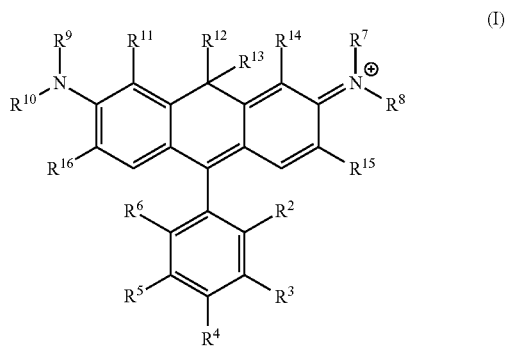

or a pharmaceutically acceptable salt thereof, wherein $R^{12}$ and $R^{13}$ are each independently H, alkyl, substituted alkyl, -L-$R_x$, or -L-$S_c$;

$R^2$, $R^3$, $R^4$, $R^5$, $R^6$, $R^7$, $R^8$, $R^9$, $R^{10}$, $R^{11}$, $R^{14}$, $R^{15}$, and $R^{16}$ are each independently H, halogen, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester) amino, (carboxyl ester) oxy, cyano, alkylcarboxylate, hydroxyl, nitro, sulfo, sulfoalkyl, substituted sulfoalkyl, sulfonyl, substituted sulfonyl, sulfonyloxy, thioacyl, thiol, alkylthiol, substituted alkylthiol, aryl, substituted aryl, heteroaryl, substituted heteroaryl, cycloalkyl, substituted cycloalkyl, heterocyclyl, substituted heterocyclyl, -L-$R_x$, or -L-$S_c$; or $R^7$ taken together with $R^{14}$ are part of an optionally substituted 5- or 6-membered ring;

$R^8$ taken together with $R^{15}$ are part of an optionally substituted 5- or 6-membered ring;

$R^9$ taken together with $R^{11}$ are part of an optionally substituted 5- or 6-membered ring;

$R^{10}$ taken together with $R^{16}$ are part of an optionally substituted 5- or 6-membered ring;

L is a linker;

$R_x$ is a reactive group; and $S_c$ is a conjugated substance;

b) an organic solvent; and c) a desiccant.

In certain embodiments, $R^2$ is carboxyl, -L-$R_x$, or -L-$S_c$. In certain embodiments, $R^7$, $R^8$, $R^9$, and $R^{10}$ are each independently H, alkyl, substituted alkyl, or sulfoalkyl. In certain embodiments, $R^7$, $R^8$, $R^9$, and $R^{10}$ are each independently a $C_1$-$C_6$ alkyl, which can be the same or different. In certain embodiments, $R^7$, $R^8$, $R^9$, and $R^{10}$ are each methyl. In certain embodiments, $R^{12}$ and $R^{13}$ are each alkyl, preferably a $C_1$-$C_6$ alkyl. In certain embodiments, $R^{12}$ and $R^{13}$ are each methyl. In certain embodiments, $R^{11}$ and $R^{14}$ are each independently alkyl, substituted alkyl, sulfoalkyl, sulfo, -L-$R_x$, or -L-$S_c$. In certain embodiments, $R^{11}$ and $R^{14}$ are each independently a $C_1$-$C_6$ alkyl, a $C_1$-$C_6$ substituted alkyl, or sulfoalkyl, which can be the same or different. In certain embodiments, $R_x$ is succinimidyl ester (SE), sulfodichlorophenyl (SDP) ester, sulfotetrafluorophenyl (STP) ester, tetrafluorophenyl (TFP) ester, pentafluorophenyl (PFP) ester, nitrilotriacetic acid (NTA), aminodextran, and cyclooctyne-amine.

Another embodiment provides a kit for tracking cell proliferation, differentiation and/or function, the kit being compatible for use with, for example, flow cytometry and fluorescence microscopy, and comprising:

a) a compound of structural formula (II):

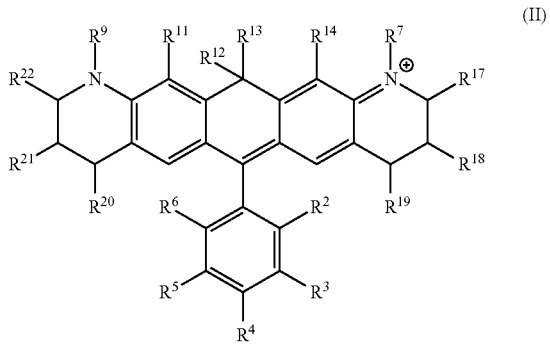

(II)

or a pharmaceutically acceptable salt thereof, wherein
$R^{12}$ and $R^{13}$ are each independently H, alkyl, substituted alkyl, -L-$R_x$, or -L-$S_c$;
$R^2$, $R^3$, $R^4$, $R^5$, $R^6$, $R^7$, $R^9$, $R^{11}$, $R^{14}$, $R^{17}$, $R^{18}$, $R^{19}$, $R^{20}$, $R^{21}$ and are each independently H, halogen, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester) amino, (carboxyl ester) oxy, cyano, alkylcarboxylate, hydroxyl, nitro, sulfo, sulfoalkyl, substituted sulfoalkyl, sulfonyl, substituted sulfonyl, sulfonyloxy, thioacyl, thiol, alkylthiol, substituted alkylthiol, aryl, substituted aryl, heteroaryl, substituted heteroaryl, cycloalkyl, substituted cycloalkyl, heterocyclyl, substituted heterocyclyl, -L-$R_x$, or -L-$S_c$;
L is a linker;
$R_x$ is a reactive group; and
$S_c$ is a conjugated substance;
b) an organic solvent; and
c) a desiccant.

In certain embodiments, $R^{12}$ and $R^{13}$ are each alkyl, preferably a $C_1$-$C_6$ alkyl. In certain embodiments, $R^{12}$ and $R^{13}$ are each methyl. In certain embodiments, $R^2$ is carboxyl, -L-$R_x$, or -L-$S_c$. In certain embodiments, $R^3$, $R^4$, $R^5$ and $R^6$ are each independently H or halo. In certain embodiments, $R^3$, $R^4$, $R^5$ and $R^6$ are independently H, Cl, or F. In certain embodiments, $R^7$ and $R^9$ are each independently alkyl, substituted alkyl, sulfoalkyl, sulfo, -L-$R_x$, or -L-$S_c$. In certain embodiments, $R^7$ and $R^9$ are each independently methyl, -L-$R_x$, -L-$S_c$ or $(CH_2)_nSO_3^-$, wherein n is an integer between 1 and 6. In certain embodiments, n is 3. In certain embodiments, $R_x$ is succinimidyl ester (SE), sulfodichlorophenyl (SDP) ester, sulfotetrafluorophenyl (STP) ester, tetrafluorophenyl (TFP) ester, pentafluorophenyl (PFP) ester, nitrilotriacetic acid (NTA), aminodextran, and cyclooctyne-amine.

Another embodiment provides a kit for tracking cell proliferation, differentiation and/or function, the kit being compatible for use with, for example, flow cytometry and fluorescence microscopy, and comprising:

a) a compound of structural formula (III):

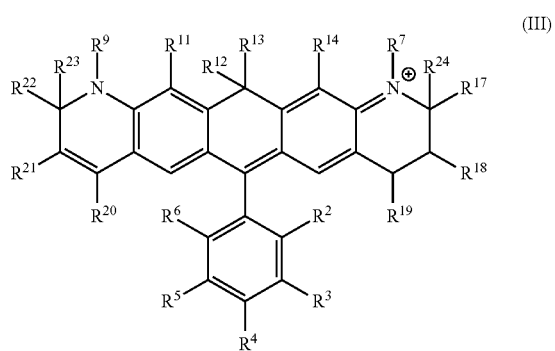

(III)

or a pharmaceutically acceptable salt thereof, wherein
$R^{12}$ and $R^{13}$ are each independently H, alkyl, substituted alkyl, -L-$R_x$, or -L-$S_c$;
$R^2$, $R^3$, $R^4$, $R^5$, $R^6$, $R^7$, $R^9$, $R^{11}$, $R^{14}$, $R^{17}$, $R^{18}$, $R^{19}$, $R^{20}$, $R^{21}$, $R^{22}$, $R^{23}$ and $R^{24}$ are each independently H, halogen, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester) amino, (carboxyl ester) oxy, cyano, alkylcarboxylate, hydroxyl, nitro, sulfo, sulfoalkyl, substituted sulfoalkyl, sulfonyl, substituted sulfonyl, sulfonyloxy, thioacyl, thiol, alkylthiol, substituted alkylthiol, aryl, substituted aryl, heteroaryl, substituted heteroaryl, cycloalkyl, substituted cycloalkyl, heterocyclyl, substituted heterocyclyl, -L-$R_x$, or -L-$S_c$;
L is a linker;
$R_x$ is a reactive group; and
$S_c$ is a conjugated substance;
b) an organic solvent; and
c) a desiccant.

In certain embodiments, $R^{12}$ and $R^{13}$ are each alkyl, preferably a $C_1$-$C_6$ alkyl. In certain embodiments, $R^{12}$ and $R^{13}$ are each methyl. In certain embodiments, $R^2$ is carboxyl, -L-$R_x$, or L-$S_c$. In certain embodiments, $R^7$, $R^9$, $R^{17}$, $R^{19}$, $R^{20}$, $R^{22}$, $R^{23}$ and $R^{24}$ are each independently alkyl, substituted alkyl, sulfoalkyl, sulfo, -L-$R_x$, or -L-$S_c$. In certain embodiments, $R^7$, $R^9$, $R^{17}$, $R^{22}$, and $R^{24}$ are each methyl. In certain embodiments, $R^{19}$ and $R^{20}$ are each independently $(CH_2)_nSO_3^-$, wherein n is an integer between 1 and 6. In certain embodiments, n is 1. In certain embodiments, $R_x$ is succinimidyl ester (SE), sulfodichlorophenyl (SDP) ester, sulfotetrafluorophenyl (STP) ester, tetrafluorophenyl (TFP) ester, pentafluorophenyl (PFP) ester, nitrilotriacetic acid (NTA), aminodextran, and cyclooctyne-amine.

Another embodiment provides a kit for tracking cell proliferation, differentiation and/or function, the kit being compatible for use with, for example, flow cytometry and fluorescence microscopy, and comprising:

a) a compound of structural formula (IV):

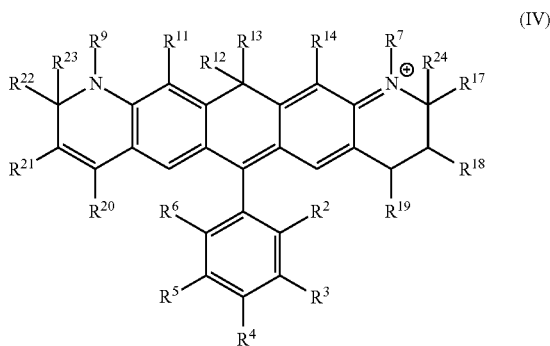

or a pharmaceutically acceptable salt thereof, wherein $R^{12}$ and $R^{13}$ are each independently H, alkyl, substituted alkyl, -L-$R_x$, or -L-$S_c$;

$R^2$, $R^3$, $R^4$, $R^5$, $R^6$, $R^7$, $R^9$, $R^{11}$, $R^{14}$, $R^{17}$, $R^{18}$, $R^{19}$, $R^{20}$, $R^{21}$, $R^{22}$, and $R^{24}$ are each independently H, halogen, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester) amino, (carboxyl ester) oxy, cyano, alkylcarboxylate, hydroxyl, nitro, sulfo, sulfoalkyl, substituted sulfoalkyl, sulfonyl, substituted sulfonyl, sulfonyloxy, thioacyl, thiol, alkylthiol, substituted alkylthiol, aryl, substituted aryl, heteroaryl, substituted heteroaryl, cycloalkyl, substituted cycloalkyl, heterocyclyl, substituted heterocyclyl, -L-$R_x$, or -L-$S_c$;

L is a linker;
$R_x$ is a reactive group; and
$S_c$ is a conjugated substance;

b) an organic solvent; and
c) a desiccant.
c) a desiccant.

In certain embodiments, $R^9$, $R^{12}$, $R^{13}$, $R^{22}$ and $R^{23}$ are each alkyl, preferably a $C_1$-$C_6$ alkyl. In certain embodiments, $R^9$, $R^{12}$, $R^{13}$, $R^{22}$ and $R^{23}$ are each methyl. In certain embodiments, $R^3$, $R^4$, $R^5$ and $R^6$ are each independently H or halo. In certain embodiments, $R^3$ and $R^6$ are independently H, Cl, or F. In certain embodiments, $R^2$ is carboxyl. In certain embodiments, $R^7$, $R^9$ and $R^{20}$ are each independently alkyl, substituted alkyl, sulfoalkyl, sulfo, $(CH_2)_nSO_3^-$, wherein n is an integer between 1 and 6, -L-$R_x$, or -L-$S_c$. In certain embodiments, $R^7$ is L-$R_x$ and $R^{20}$ is $(CH_2)_nSO_3^-$. In certain embodiments, n is 1. In certain embodiments, $R_x$ is succinimidyl ester (SE), sulfodichlorophenyl (SDP) ester, sulfotetrafluorophenyl (STP) ester, tetrafluorophenyl (TFP) ester, pentaflurophenyl (PFP) ester, nitrilotriacetic acid (NTA), aminodextran, and cyclooctyneamine.

In certain embodiments, $R_x$ is selected from an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, an imido ester, an isocyanate, an isothiocyanate, a maleimide, a phosphoramidite, a photoactivatable group, a reactive platinum complex, a silyl halide, a sulfonyl halide, and a thiol. In certain embodiments the reactive group is selected from the group consisting of carboxylic acid, succinimidyl ester of a carboxylic acid, hydrazide, amine and a maleimide. The reactive group may be attached to any appropriate site on the reporter molecule or the aniline moiety. In certain embodiments, at least one member selected from $R^2$, $R^3$, $R^4$, $R^5$, $R^6$, $R^7$, $R^8$, $R^9$, $R^{10}$, $R^{12}$, $R^{13}$, $R^{19}$ and $R^{20}$ is a reactive group. In certain embodiments, at least one of $R^2$, $R^4$, $R^5$, $R^7$, $R^8$, $R^9$, $R^{10}$, $R^{12}$ and $R^{13}$ is a reactive group. In certain embodiments, at least one of $R^7$, $R^8$, $R^9$, $R^{10}$, $R^{12}$ and $R^{13}$ is a reactive group.

In certain embodiments, $S_c$ is selected from a carrier molecule and a solid support. In certain embodiments, $S_c$ is selected from an amino acid, a polymer of amino acids, a peptide, a protein, a neurotoxin, a phallotoxin, a cytokine, a toxin, a protease substrate, a protein kinase substrate, an enzyme, an antibody, an antibody fragment, a lectin, a glycoprotein, a histone, an albumin, a lipoprotein, avidin, streptavidin, protein A, protein G, a phycobiliprotein, a fluorescent protein, a hormone, a growth factor, a nucleic acid base, a nucleoside, a nucleotide, a nucleic acid polymer, a nucleotide analog, a nucleoside analog, a nucleoside triphosphate, a deoxynucleoside triphosphate, a dideoxynucleoside triphosphate, a hapten, a carbohydrate, a polysaccharide, a lipid, an ion-complexing moiety (such as a crown ether), a PEG group, and an organic or inorganic polymer. In certain embodiments, at least one member selected from $R^2$, $R^3$, $R^4$, $R^5$, $R^6$, $R^7$, $R^8$, $R^9$, $R^{10}$, $R^{12}$, $R^{13}$, $R^{19}$ and $R^{20}$ is a conjugated substance. In certain embodiments, at least one of $R^2$, $R^4$, $R^5$, $R^7$, $R^8$, $R^9$, $R^{10}$, $R^{12}$ and $R^{13}$ is a conjugated substance. In certain embodiments, at least one of $R^7$, $R^8$, $R^9$, $R^{10}$, $R^{12}$ and $R^{13}$ is a conjugated substance. In certain embodiments, at least one of $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ are a PEG group.

In certain embodiments, the compounds used in the kits provided herein are selected from the group consisting of Compound 1, Compound 2, Compound 3, Compound 4, Compound 5, Compound 6, Compound 7, Compound 8, Compound 9, Compound 10, Compound 11, Compound 12, Compound 13, Compound 14, Compound 15, Compound 16, Compound 17, Compound 18, Compound 19, Compound 20, Compound 21, Compound 22, Compound 23, Compound 24, Compound 25, and amine-reactive forms thereof.

In another illustrative embodiment of the kit, $R_x$ is a succinimidyl ester. In another illustrative embodiment, the organic solvent is DMSO.

In certain embodiments, kits for tracking cell proliferation, differentiation and/or function are provided, the kit comprising:

(a) one or more of the compounds described herein;
(b) one or more containers; and optionally
(c) instructions for tracking cell proliferation, differentiation, and/or function according to a method disclosed herein.

In certain embodiments, kits are provided, the kit comprising:

(a) one or more of the compounds described herein;
(b) one or more containers; and optionally
(c) instructions for using according to a method disclosed herein.

In certain embodiments, the kits further comprise one or more of the following: a buffering agent, a purification medium, a vial comprising the sample, or an organic solvent.

As used herein, the term "kit" refers to a packaged set of related components, typically one or more dye compounds or compositions. In certain embodiments, the kits disclosed herein comprise one or more of the dye compounds described herein, one or more carriers suitable for in vitro or in vivo applications, and one or more containers in which to store the one or more dye compounds and/or one or more carriers, such as solvents, buffers, stabilizers, pH adjusting agents, etc. The kit optionally contains instructions for how to prepare the one or more dye compounds or how to prepare a composition containing the one or more dye compounds, and how to administer the dye compound or composition containing the dye compound. In certain embodiments, the kit comprises instructions for performing an assay that tracks cellular proliferation, differentiation, and/or function. In certain embodiments, the assay is an in vitro assay. In certain embodiments, the assay is an in vivo assay. The kit may further comprise one or more pieces of equipment to administer the compound, or composition containing the compound including, but not limited to, syringes, pipettes, pipette bulbs, spatulas, vials, syringe needles, and various combinations thereof.

In certain embodiments, the kits provided herein comprise indicator solutions or indicator "dipsticks", blotters, culture media, cuvettes, and the like. In certain embodiments, the kits provided herein comprise indicator cartridges (where a kit component is bound to a solid support) for use in an automated detector. In certain embodiments, the kits provided herein further comprise molecular weight markers, wherein said markers are selected from phosphorylated and non-phosphorylated polypeptides, calcium-binding and non-calcium binding polypeptides, sulfonated and non-sulfonated polypeptides, and sialylated and non-sialylated polypeptides. In certain embodiments, the kits provided herein further comprise a member selected from a fixing solution, a detection reagent, a standard, a wash solution, and combinations thereof.

In certain embodiments, kits for tracking cell proliferation, differentiation and/or function are provided, the kit comprising:

(a) one or more of the compositions described herein;
(b) one or more containers; and optionally
(c) instructions for tracking cell proliferation, differentiation, and/or function according to a method disclosed herein.

A detailed description of the present teachings having been provided above, the following examples are given for the purpose of illustrating the present teachings and shall not be construed as being a limitation on the scope of the disclosure or claims.

EXAMPLES

Example 1: Chemical Synthesis of Cell Tracking Compounds

A. Synthesis of Compound 2:

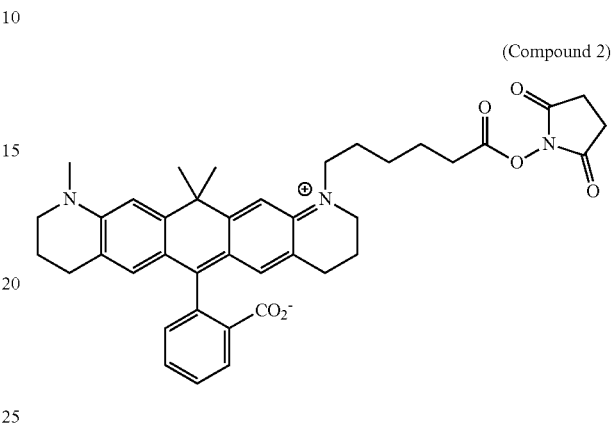

(Compound 2)

1,2,3,4-tetrahydroquinoline (10 g, 75.2 mmol)) was dissolved in ethanol (100 mL). 20 mL of 37% formaldehyde was added, followed by addition of $NaCNBH_3$ (9.4 g) and 1 mL of AcOH. The reaction was stirred for 18 hours. The reaction mixture was treated with 100 mL of saturated ammonium chloride and stirred for 1 hour. After removal of ethanol in vacuo, the remaining solution was extracted with 200 mL of dichloromethane twice. The combined organic layer was washed with saturated NaCl, dried over sodium sulfate and concentrated in vacuo. The residue was purified by flash chromatograph with hexane-ethyl acetate to afford 1-methyl-1,2,3,4-tetrahydroquinoline as a clear oil (yield: 90%). $^1$H NMR ($CDCl_3$): δ 7.13 (t, 1H), 7.0 (t, 1H), 6.63 (m, 2H), 3.26 (t, 2H), 2.90 (s, 3H), 2.80 (m, 2H), 2.01 (t, 2H).

Phthalic anhydride (9.6 g, 65.3 mmol), anhydrous aluminum chloride (10.8 g, 80.9 mmol), and dry dichloromethane (100 mL) were added to a 250 mL of flask. The mixture was stirred for 1 hour at room temperature and cooled in an ice bath. The solution of 1-methyl-1,2,3,4-tetrahydroquinoline (8.0 g, 60.1 mmol) dissolved in 40 mL of dichloromethane was added dropwise. After the addition was complete, the reaction was stirred for 4 hours at room temperature. The reaction mixture was poured into ice-cold HCl solution, and extracted with dichloromethane. The organic layer was collected and dried over sodium sulfate. It was purified by column chromatography with dichloromethane-methanol on silica gel to yield 2-(1-methyl-1,2,3,4-tetrahydroquinoline-6-carbonyl)benzoic acid (yield: 30%). $^1$H NMR ($d_6$-DMSO): δ 7.90 (s, 1H), 7.67 (m, 2H), 7.32 (m, 2H), 6.50 (m, 2H), 3.20 (t, 2H), 2.98 (s, 3H), 2.65 (m, 2H), 1.89 (t, 2H)

7-bromo-1, 2,3,4-tetrahydroquinoline (5.0 g, 23.6 mmol) was dissolved in DMF (10 mL). Potassium carbonate (6.4 g) and 6-bromohexanoate ethyl ester (10.0 g, 47.2 mmol) were added into the solution. The mixture was heated to 100° C. for 18 hours. After the reaction was cooled down, 50 mL of dichloromethane was added and washed with 10 mL of water three times. The organic layer was dried over sodium sulfate and concentrated. It was purified by flash chromatography in silica gel with hexanes-ethyl acetate to afford ethyl 6-(7-bromo-3,4-dihydroquinolin-1(2H)-yl)hexanoates as a clear oil (yield: 70%). $^1$H NMR (CDCl$_3$): δ 6.79 (d, 1H), 6.64 (d, 2H), 4.15 (t, 2H), 3.29 (t, 2H), 3.21 (t, 2H), 2.32 (t, 2H), 1.92 (m, 2H), 1.72 (m, 2H), 1.65 (m, 2H), 1.43 (m, 2H), 1.31 (t, 3H).

Ethyl 6-(7-bromo-3,4-dihydroquinolin-1(2H)-yl)hexanoate (4.0 g, 11.3 mmol), isopropenylboronic acid pinacol ester (2.7 g, 16.1 mmol), palladium acetate (253 mg), and potassium carbonate (4.65 g) were mixed with 50 mL of toluene, 50 mL of isopropanol, and 50 mL of water. The mixture was bubbled with argon for 10 min. The mixture was heated to 100° C. for 16 hours.

After removal of organic solvents in vacuo, the residue was extracted with dichloromethane three times. The combined organic layer was dried over sodium sulfate and concentrated. It was purified by flash chromatography with hexane-ethyl acetate to afford ethyl 6-(7-(prop-1-en-2-yl)-3,4-dihydroquinolin-1(2H)-yl)hexanoate as light yellow oil (yield: 67%). $^1$H NMR (CDCl$_3$): δ 6.92 (d, 1H), 6.68 (m, 2H), 5.28 (s, 1H), 5.01 (s, 1H), 4.14 (t, 2H), 3.30 (m, 4H), 2.74 (t, 2H), 2.32 (t, 2H), 2.12 (s, 3H), 1.95 (m, 2H), 1.66 (m, 4H), 1.42 (m, 2H), 1.29 (t, 3H).

2-(1-methyl-1,2,3,4-tetrahydroquinoline-6-carbonyl)benzoic acid (3.9 g, 13.2 mmol), and ethyl 6-(7-(prop-1-en-2-yl)-3,4-dihydroquinolin-1(2H)-yl)hexanoate (4.0 g, 12.7 mmol) were dissolved in dry dichloromethane (100 mL). P$_2$O$_5$ (9.0 g) was added into the stirred solution. The mixture was refluxed for 1 hour. After removal of solvent, the residue was treated with sulfuric acid (10 mL). The reaction was stirred for 18 hours. It was poured into ice and extracted with dichloromethane three times. The combined organic layer was dried over sodium sulfate and concentrated. It was purified by flash chromatography with 15% water in acetonitrile to afford 2-(1-(5-carboxypentyl)-11-metheyliumyl-13,13-dimethyl-1,2,3,4,8,9,10,13-octahydro-1114-benzo diquinolin-6-yl)benzoate (Compound 1) as a dark blue solid (yield: 9%). $^1$H NMR (MeOD): δ 8.29 (d, 1H), 7.81 (t, 1H), 7.74 (t, 1H), 7.29 (d, 1H), 7.10 (d, 1H), 6.65 (d, 1H), 3.71 (t, 2H), 3.60 (m, 4H), 2.55 (m, 4H), 2.41 (t, 2H), 1.92 (m, 4H), 1.70 (m, 10H), 1.52 (m, 2H).

2-(1-(5-carboxypentyl)-11-metheyliumyl-13,13-dimethyl-1,2,3,4,8,9,10,13-octahydro-1114-benzo[1,2-g:5,4-g']diquinolin-6-yl)benzoate (600 mg, 1.06 mmol) was dissolved in dry DMF (10 mL). DIEA (0.36 mL) and TSTU (340 mg) were added to the solution. The reaction was stirred for 1 hour and was added dropwise to ethyl ether (100 mL). The mixture was centrifuged to afford 2-(1-(6-((2,5-dioxopyrrolidin-1-yl)oxy)-6-oxohexyl)-11-metheyliumyl-13,13-dimethyl-1,2,3,4,8,9,10,13-octahydro-1114-benzo[1,2-g:5,4-g']diquinolin-6-yl)benzoate (Compound 2) after filtration from ethyl ether as a dark blue powder (yield: 92%). $^1$H NMR (MeOD): δ 8.26 (d, 1H), 7.80 (t, 1H), 7.73 (t, 1H), 7.30 (d, 1H), 7.12 (d, 2H), 6.63 (d, 2H), 3.70 (t, 2H), 3.62 (m, 4H), 2.80 (t, 2H), 2.70 (m, 4H), 2.60 (t, 2H), 1.94 (m, 4H), 1.72 (m, 10H), 1.50 (m, 2H).

B. Synthesis of Compound 3:

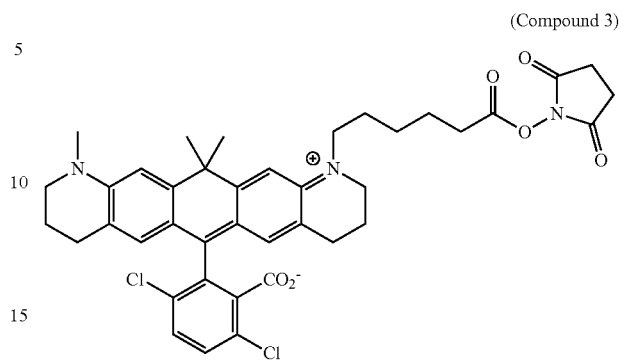

(Compound 3)

3,6-dichlorophthalic anhydride (0.5 g, 2.30 mmol), anhydrous aluminum chloride (0.6 g, 4.5 mmol), dry dichloromethane (10 mL) were added to a 100 mL flask. The mixture was stirred for 1 hour at room temperature and cooled in an ice bath. A solution of 1-methyl-1,2,3,4-tetrahydroquinoline (0.40 g) dissolved in 10 mL of dichloromethane was added dropwise. After the addition was complete, the reaction was stirred for 4 hours at room temperature. The reaction mixture was poured into an ice cold HCl solution, and extracted with dichloromethane. The organic layer was collected and dried over sodium sulfate. It was purified by column chromatography with 5% methanol in dichloromethane on silica gel to yield 3,6-dichloro-2-(1-methyl-1,2,3,4-tetrahydroquinoline-6-carbonyl)benzoic acid (yield: 30%). $^1$H NMR (d$_6$-DMSO): δ 7.62 (s, 1H), 6.91 (m, 1H), 6.82 (m, 1H), 6.50 (m, 2H), 3.14 (t, 2H), 2.91 (s, 3H), 2.69 (m, 2H), 1.85 (t, 2H).

3,6-dichloro-2-(1-methyl-1,2,3,4-tetrahydroquinoline-6-carbonyl)benzoic acid (0.10 g, 0.27 mmol) and ethyl 6-(7-(prop-1-en-2-yl)-3,4-dihydroquinolin-1(2H)-yl)hexanoate (0.088 g, 0.27 mmol) were dissolved in dry dichloromethane (5 mL). P$_2$O$_5$ (0.200 g) was added into the stirred solution. The mixture was refluxed for 1 hour. After removal of solvent, the residue was treated with sulfuric acid (3 mL). The reaction was stirred for 18 hours. It was poured into ice and extracted with dichloromethane three times. The combined organic layer was dried over sodium sulfate and concentrated. It was purified by flash chromatography with 5% methanol in dichloromethane on silica gel to afford 2-(1-(5-carboxypentyl)-11-metheyliumyl-13,13-dimethyl-1,2,3,4,8,9,10,13-octahydro-1114-benzo[1,2-g:5,4-g]diquinolin-6-yl)-3,6-dichlorobenzoate as a dark blue solid (yield: 9%). LCMS: 634.6 (M+1)

2-(1-(5-carboxypentyl)-11,13,13-trimethyl-2,3,4,8,9,10,11,13-octahydrobenzo[1,2-g:5,4-g']diquinolin-1-ium-6-yl)-3,6-dichlorobenzoate (20 mg, 0.032 mmol) was dissolved in dry DMF (1 mL). TEA (0.10 mL) and TSTU (15 mg) were added to the solution. The reaction was stirred for 1 hour and added dropwise to ethyl ether (100 mL). The mixture was centrifuged to afford 3,6-dichloro-2-(1-(6-((2,5-dioxopyrrolidin-1-yl)oxy)-6-oxohexyl)-11-metheyliumyl-13,13-dimethyl-1,2,3,4,8,9,10,13-octahydro-1114-benzo[1,2-g:5,4-g']diquinolin-6-yl)benzoate (Compound 3) after filtration of ethyl ether as dark blue powder (yield: 90%). $^1$H NMR (MeOD): δ 8.20 (d, 1H), 7.28 (d, 1H), 7.11 (d, 2H), 6.58 (d, 2H), 3.69 (t, 2H), 3.62 (m, 4H), 2.80 (t, 4H), 2.69 (m, 4H), 2.58 (t, 2H), 1.94 (m, 4H), 1.72 (m, 10H), 1.50 (m, 2H), LCMS: 731.7 (M+1).

C. Synthesis of Compound 18:

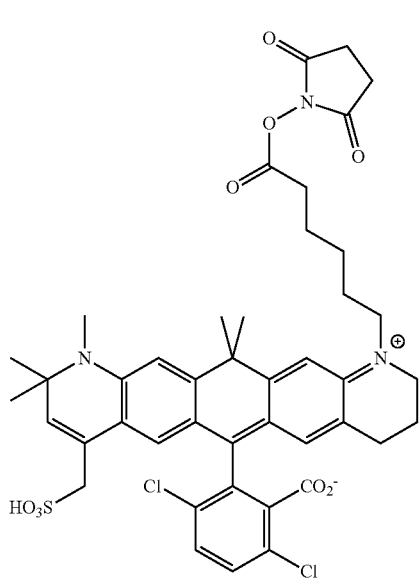

(Compound 18)

Aniline (2 g, 21.5 mmol) was dissolved in THF (20 mL) and cooled to 0° C. in an ice bath. TFA (1 eq) was added into the solution and stirred for 15 min. Mesityl oxide (4-methyl-3-penten-2-one) (1.2 eq) was added into the mixture, which was allowed to warm up to room temperature. The reaction was stirred overnight. After THF was removed in vacuo, the residue was suspended in $CHCl_3$ (~2 L), and mechanically stirred until a uniform solution was achieved. $H_2O$ (~1.5 L) was added to the solution, and the pH was adjusted to 8-9 using solid KOH. The organic phase was washed with $H_2O$ (3×~1 L) and brine (~1 L), and dried over anhydrous sodium sulfate ($Na_2SO_4$). After $CHCl_3$ was removed in vacuo, the residue was dissolved in ethanol (20 mL), formaldehyde (37%, 2 mL) was added, followed by addition of $NaCNBH_3$ (3.5 g) and 1 mL of AcOH. The reaction was stirred for 18 hours. The reaction mixture was treated with 100 mL of saturated ammonium chloride and stirred for 1 hour. After removal of ethanol in vacuo, the remaining solution was extracted with 200 mL of dichloromethane twice. The combined organic layer was washed with saturated NaCl, dried over sodium sulfate and concentrated in vacuo. The residue was purified by flash chromatograph with hexane-ethyl acetate to afford 1,2,2,4-tetramethyl-1,2-dihydroquinoline as a light yellow oil (yield: 70%). $^1H$ NMR ($CDCl_3$): δ 7.23 (t, 2H), 6.65 (m, 2H), 5.26 (s, 1H), 2.80 (s, 3H), 2.00 (s, 3H), 1.32 (s, 3H).

3, 6-dichlorophthalic anhydride (5.0 g, 23 mmol), anhydrous aluminum chloride (5.8 g, 43.6 mmol), and dry dichloromethane (100 mL) were added to a 250 mL flask. The mixture was stirred for 1 hour at room temperature and cooled in an ice bath. A solution of 1,2,2,4-tetramethyl-1,2-dihydroquinoline (4.50 g, 24 mmol) dissolved in 40 mL of dichloromethane was added dropwise. After the addition was complete, the reaction was stirred for 4 hours at room temperature. The reaction mixture was poured into ice cold HCl solution, and extracted with dichloromethane. The organic layer was collected and dried over sodium sulfate. It was purified by column chromatography with dichloromethane-methanol on silica gel to yield 3,6-dichloro-2-(1,2,2,4-tetramethyl-1,2-dihydroquinoline-6-carbonyl)benzoic acid (yield: 30%). LCMS: 404.29.

3,6-dichloro-2-(1,2,2,4-tetramethyl-1,2-dihydroquinoline-6-carbonyl)benzoic acid (1.0 g, 2.47 mmol) and ethyl 6-(7-(prop-1-en-2-yl)-3,4-dihydroquinolin-1(2H)-yl)hexanoate (0.8 g, 2.53 mmol) were dissolved in dry dichloromethane (30 mL). $P_2O_5$ (3.0 g) was added into the stirred solution. The mixture was refluxed for 1 hour. After removal of solvent, the residue was treated with sulfuric acid (10 mL). The reaction was stirred for 18 hours. It was poured into ice and extracted with dichloromethane three times. The combined organic layer was dried over sodium sulfate and concentrated. It was purified by flash chromatography with 15% water in acetonitrile on silica gel to afford 2-(1-(5-carboxypentyl)-11-metheyliumyl-2,2,13,13-tetramethyl-4-(sulfomethyl)-1,2,8,9,10,13-hexahydro-1114-benzo[1,2-g:5,4-g']diquinolin-6-yl)-3,6-dichlorobenzoate as a dark blue solid (yield:10%). LCMS: 752.72.

2-(11-(5-carboxypentan-1-ylium-1-yl)-1,2,2,13,13-pentamethyl-4-(sulfomethyl)-1,2,8,9,10,13-hexahydro-11λ4-benzo[1,2-g:5,4-g']diquinolin-6-yl)-3,6-dichlorobenzoate (50 mg, 0.066 mmol) was dissolved in dry DMF (3 mL). DIEA (0.04 mL) and TSTU (60 mg) were added to the solution. The reaction was stirred for 1 hour and added dropwise to ethyl ether (50 mL). The mixture was centrifuged to afford 3,6-dichloro-2-(1-(6-((2,5-dioxopyrrolidin-1-yl)oxy)-6-oxohexyl)-11-metheyliumyl-2,2,13,13-tetramethyl-4-(sulfomethyl)-1,2,8,9,10,13-hexahydro-1114-benzo[1,2-g:5,4-g']diquinolin-6-yl)benzoate (Compound 18) after filtration from ethyl ether as a dark blue powder (yield: 90%). LCMS: 849.80.

Example 2: Cell Tracking Activity of Compounds 2, 3 and 12

Figure 1B:
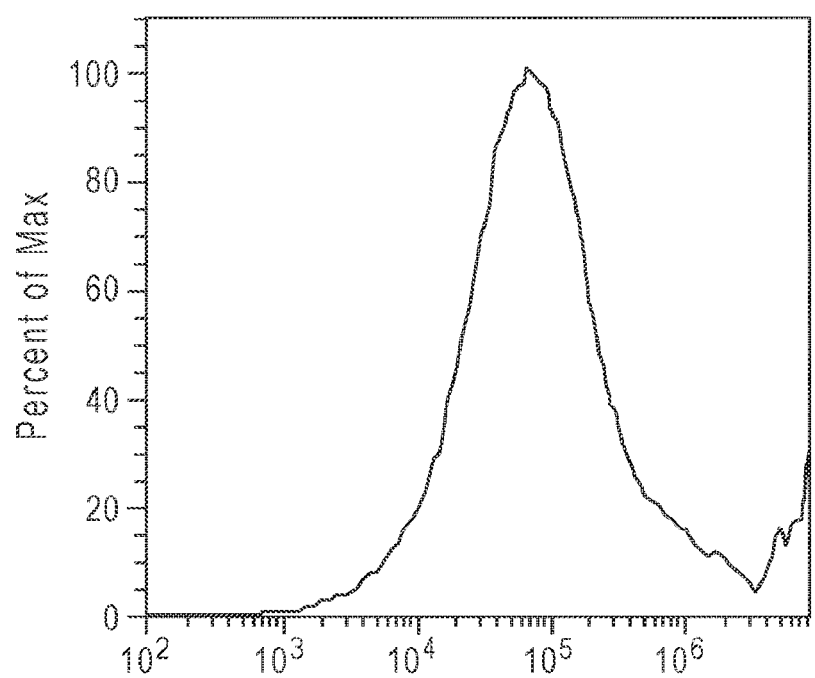

The whole blood sample (20 mL) was diluted in 20 mL of PBS and then centrifuged for 30 min after addition of FICOLL-PAQUE Plus (15 mL) (GE Healthcare). The lymphocyte layer of cells was suspended in 25 mL of PBS buffer and centrifuged for 5 min. The cells were counted on the COUNTESS Automated Counter and the concentration was adjusted to $10^6$ cells/mL. 10 mL of cells was incubated with either Compound 2 (FIG. 1A) or CELLTRACE Far Red DDAO (FIG. 1B) (Thermo Fisher Scientific) (5 μM) for 20 min in a 37° C. water bath. After incubation the cells were treated with 40 mL of OPTMIZER T Cell Expansion (Thermo Fisher Scientific) for 5 min. The treatment with OPTMIZER T Cell Expansion was repeated one more time after centrifugation. Next, the stained cells were stimulated with 50 μL DYNABEADS Human T-Activator CD3/CD28 (Thermo Fisher Scientific) per 1 mL of cells for 5 days. The stimulated cells were then analyzed using an ATTUNE flow cytometer (Thermo Fisher Scientific) with 633/635 nm excitation and a 660/20 bandpass emission filter.

Figure 2A:
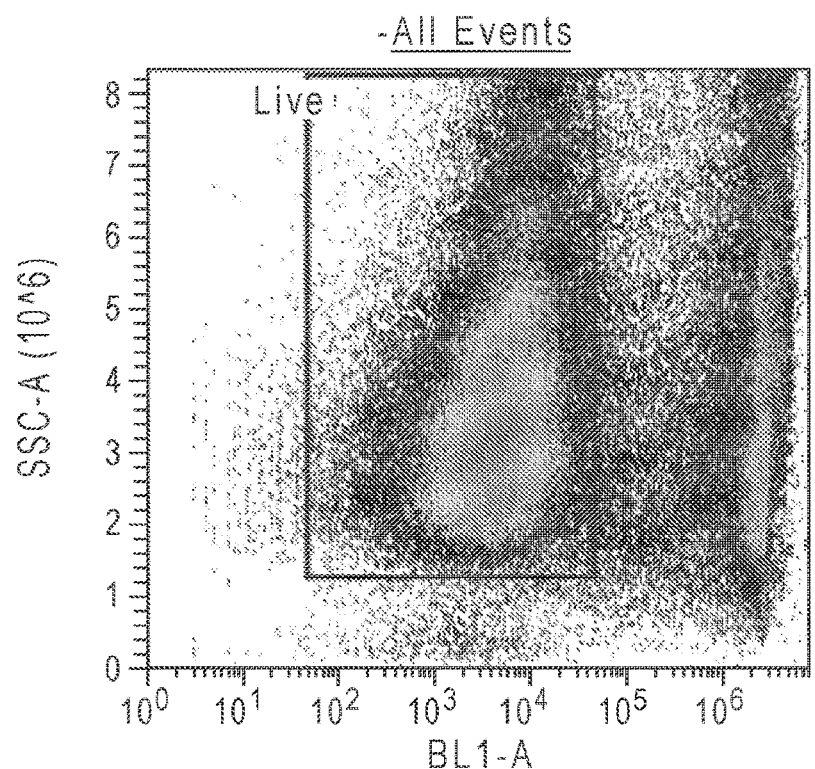
FIG. 2A: Dual parameter plot of PBMCs using SYTOX Green (Thermo Fisher Scientific) to gate for live cells for proliferation analysis with Compound 12 (see, Example 2).
Figure 2B:
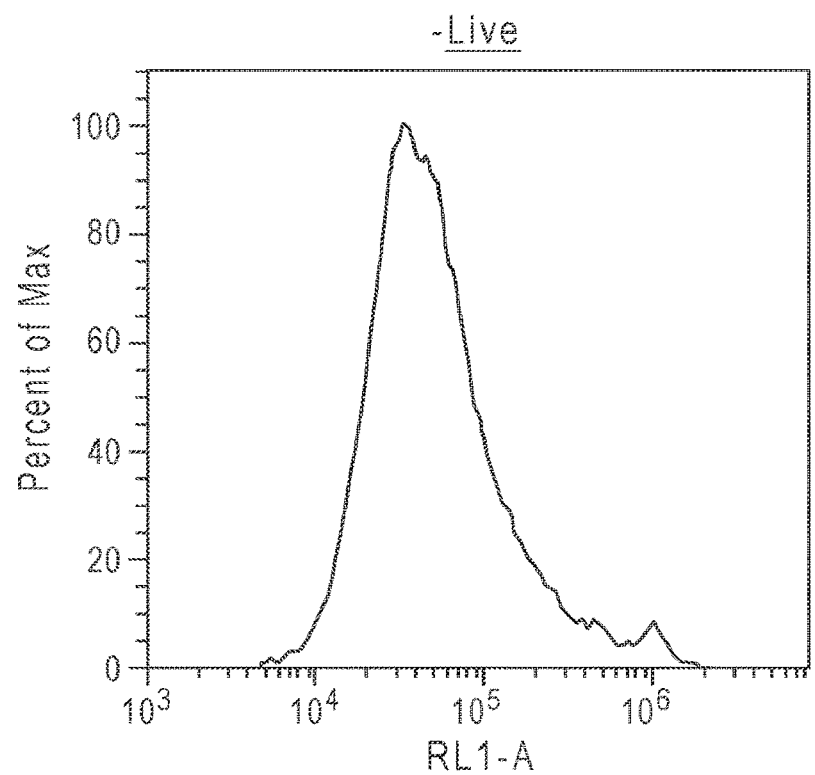
FIG. 2B: Histogram showing generational peaks of PBMCs using Compound 12.
Figure 3A:
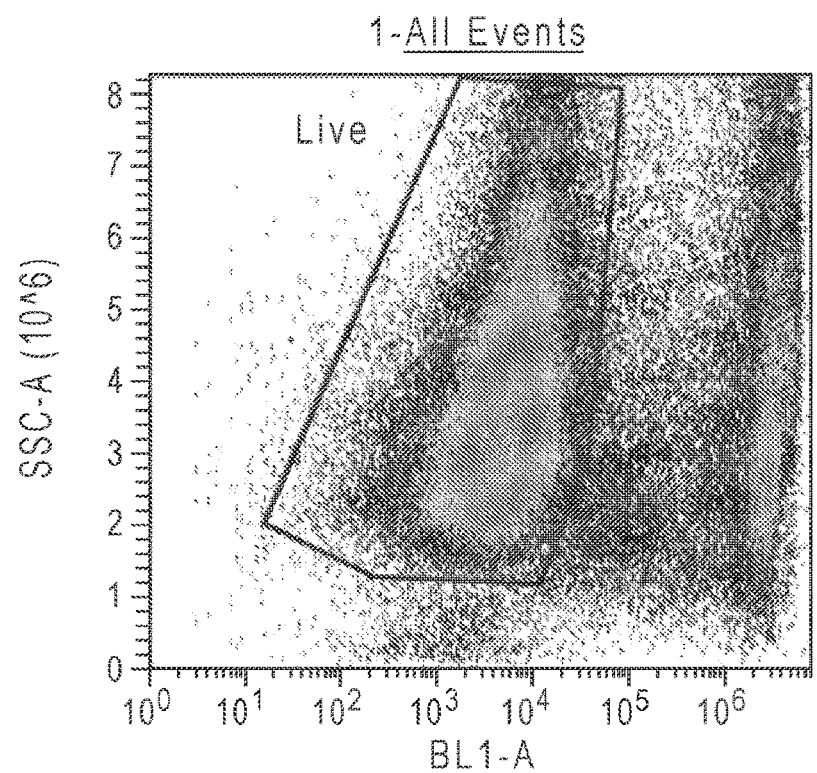
FIG. 3A: Dual parameter plot of PBMCs using SYTOX Green to gate for live cells for proliferation analysis with Compound 3 (see, Example 2).
Figure 3B:
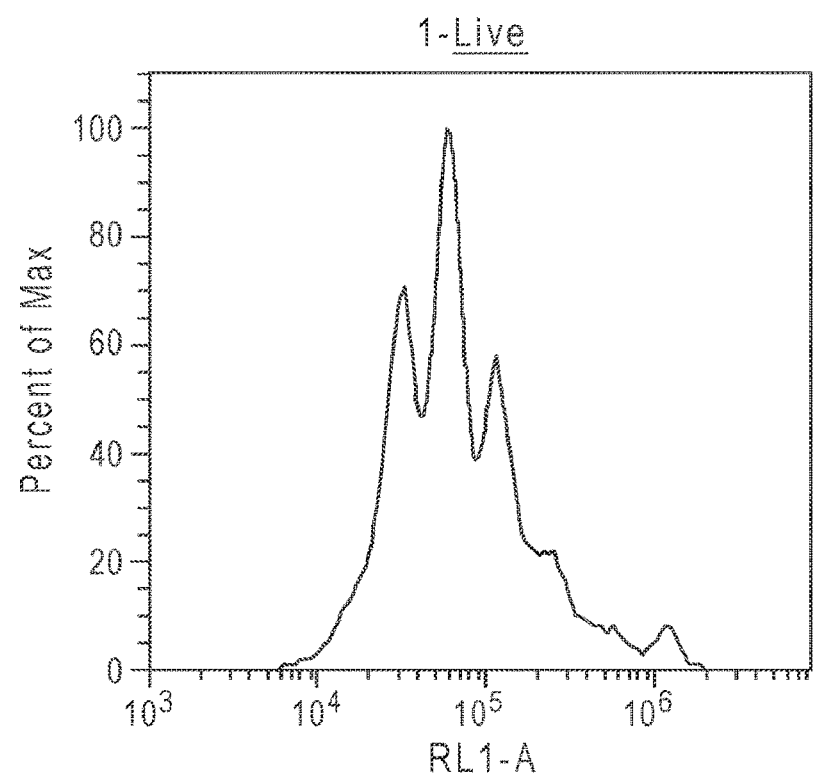
FIG. 3B: Histogram showing generational peaks of PBMCs using Compound 3.
Figure 4:
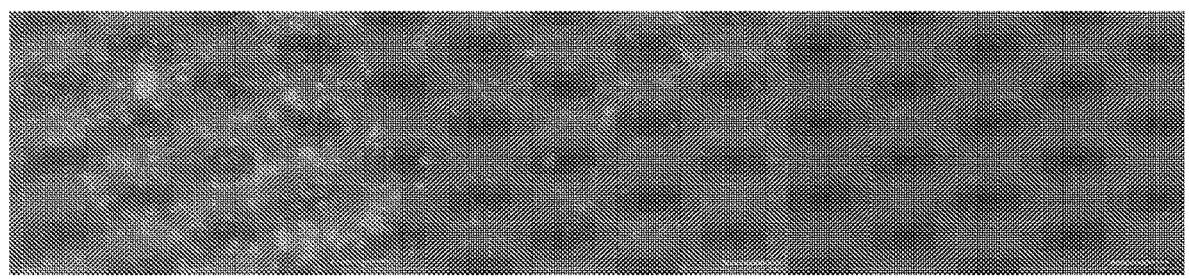
FIG. 4: Cell imaging analysis showing cell permeability of Compound 2.

Cell tracing by dye dilution was assessed by staining PBMCs isolated by FICOLL-PAQUE (GE Healthcare) density gradient centrifugation. Aliquots of isolated PBMCs were stained with Compound 3 or Compound 12, split into samples for culturing and one sample was stimulated with anti hCD3 (clone UCHT1) and supplemented with recombinant hIL2. Dye loading was observed by fluorescent microscopy. After proliferation for 3 to 5 days, samples were stained with an appropriate viability dye (e.g., a SYTOX dye (Thermo Fisher Scientific)) and analyzed by flow cytometry. Permeability was assessed by imaging. Toxicity was assessed by interrogation with the SYTOX dye. The results showing passage of the dyes through multiple cell generations are shown in FIGS. 2A and 2B (Compound 12) and FIGS. 3A and 3B (Compound 3). FIGS. 2A and 3A show a dual parameter plot showing the live cells (within the box) and FIGS. 2B and 3B show the generational peaks (6-8 generations) as determined by flow cytometry.

Briefly, for the separation of mononuclear cells from whole blood: 20 mL of whole blood were added to 20 mL DPBS and mixed well. 15 mL FICOLL-PAQUE PLUS (GE Healthcare) were added to each of two 50 mL centrifuge tubes. 20 mL of the diluted whole blood was carefully layered on top and centrifuged for 30 min at 400×g with the brake off. The PBMC layer was carefully removed. Cells were resuspended in 25 mL DPBS in a 50 mL centrifuge tube and were centrifuged for 5 min at 400×g. The supernatant was decanted and the cells were resuspended in 10 mL DPBS. Cells were counted a COUNTESS Automated Cell Counter (Thermo Fisher Scientific) (can also be counted on another counting device) and the concentration was adjusted to $1 \times 10^6$ cells/mL in DPBS.

To stain the cells, the cells were labeled with the appropriate dye compound (Compound 3 or 12, stock solution was made by adding approximately 1 µL per mL of cell suspension). The tubes were immediately vortexed for 30 sec and the cells were incubated for 20 min at room temperature, protected from light. Occasionally swirling the cells to prevent settling helped to produce more uniform labeling. 5 times the volume of stained cells of prepared OPTMIZER CTS T-Cell Expansion SFM medium (Thermo Fisher Scientific) was added and incubated 5 min at room temperature, protected from light. The cells were pelleted by centrifuging 5 min at 400×g, then pouring off the supernatant. The cell pellet was resuspended in 2 mL DPBS+10% FBS. The cells were pelleted again by centrifuging 5 min at 400×g, then pouring off the supernatant. The cell pellet was resuspended in 10 mL of prepared OPTMIZER CTS T-Cell Expansion SFM medium.

Aliquots of the stained cells were distributed into a 6-well or 24-well culture plate (at least 1 mL per well).

For stimulating and culturing T lymphocytes for proliferation analysis, the cells were stimulated with one of the following treatments:

1. 1 µg anti-hCD3 (2 µL of UCHT1) and 100 ng IL-2 (1 µL of 0.1 mg/mL solution); or
2. 50 µL CD3/CD28 DYNABEADS (Thermo Fisher Scientific) Human T-Activator CD3/CD28 T cell expander beads.

For determination of cell permeability, PBMCs were isolated by Ficoll-Pacque density gradient centrifugation and stained with the appropriate dye compound (e.g., Compound 2). The samples were split into samples for culturing and one sample was stimulated with anti-hCD3 (clone UCHT1) and supplemented with recombinant hIL2. Dye loading was observed by fluorescent microscopy. After proliferation for 3 to 5 days, the samples were stained with the appropriate viability dye (e.g., SYTOX dye) and analyzed by flow cytometry (see FIG. 3).

To test for cytotoxicity, PBMCs were stained with CELLTRACE (Thermo Fisher Scientific) CFSE (positive control) or Compound 2. The cells were split into samples for culturing and one sample was stimulated with anti-hCD3 (clone UCHT1) and supplemented with recombinant hIL2. Dye loading was observed by fluorescent microscopy. After proliferation for 3 to 5 days, the samples were stained with the appropriate viability dye (e.g., SYTOX dye) and analyzed by flow cytometry (see Table 3).

TABLE 3

| Cytotoxicity Analysis of Compound 2 | |
|---|---|
| Dye Compound | % Live Cells |
| CELLTRACE CFSE | 52 |
| Compound 2, 2 µM | 53 |
| Compound 2, 5 µM | 55 |
| Compound 2, 10 µM | 64 |

Example 3: Wound Healing Activity Analysis

Figure 5:
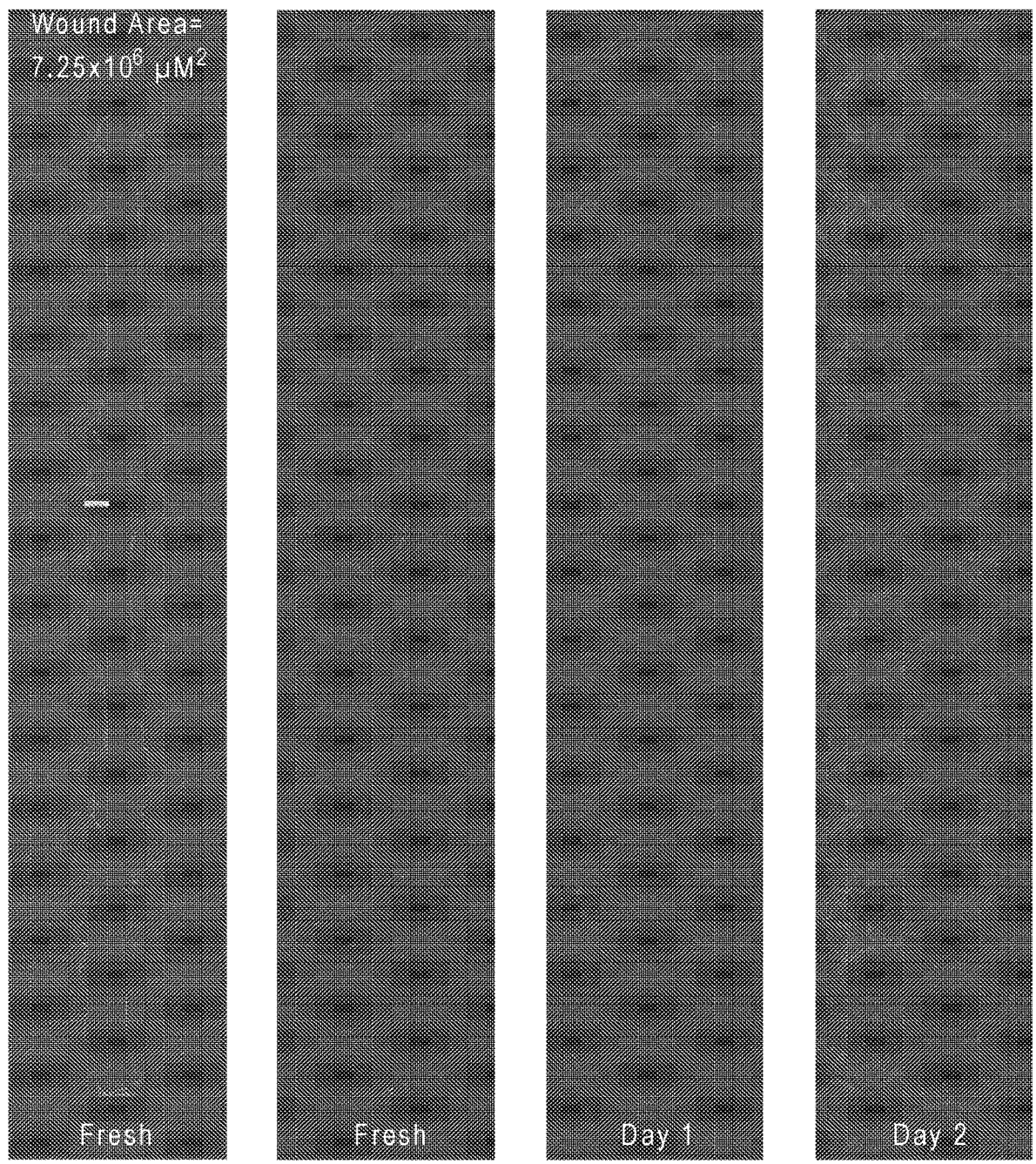
FIG. 5: Wound healing assay using Compound 2 (see, Example 3).

Neonatal human dermal fibroblasts were grown to confluency and then labeled with 1 µM Compound 2 for 30 minutes in LCIS. LCIS removed and media was placed back on cells. Scratch wound was made in the cells. The entire wound was scanned on EVOS Auto FL (Thermo Fisher Scientific) using the scan function. Same area was re-scanned 24 and 48 hours later to monitor how the wound was healing. The initial scan of the fresh wound was analyzed using the measure function on the EVOS Auto FL to calculate the area of the wound ($7.25 \times 10^6$ µm$^2$). Results are shown in FIG. 5.

Example 4: Angiogenesis Analysis

Figure 6:
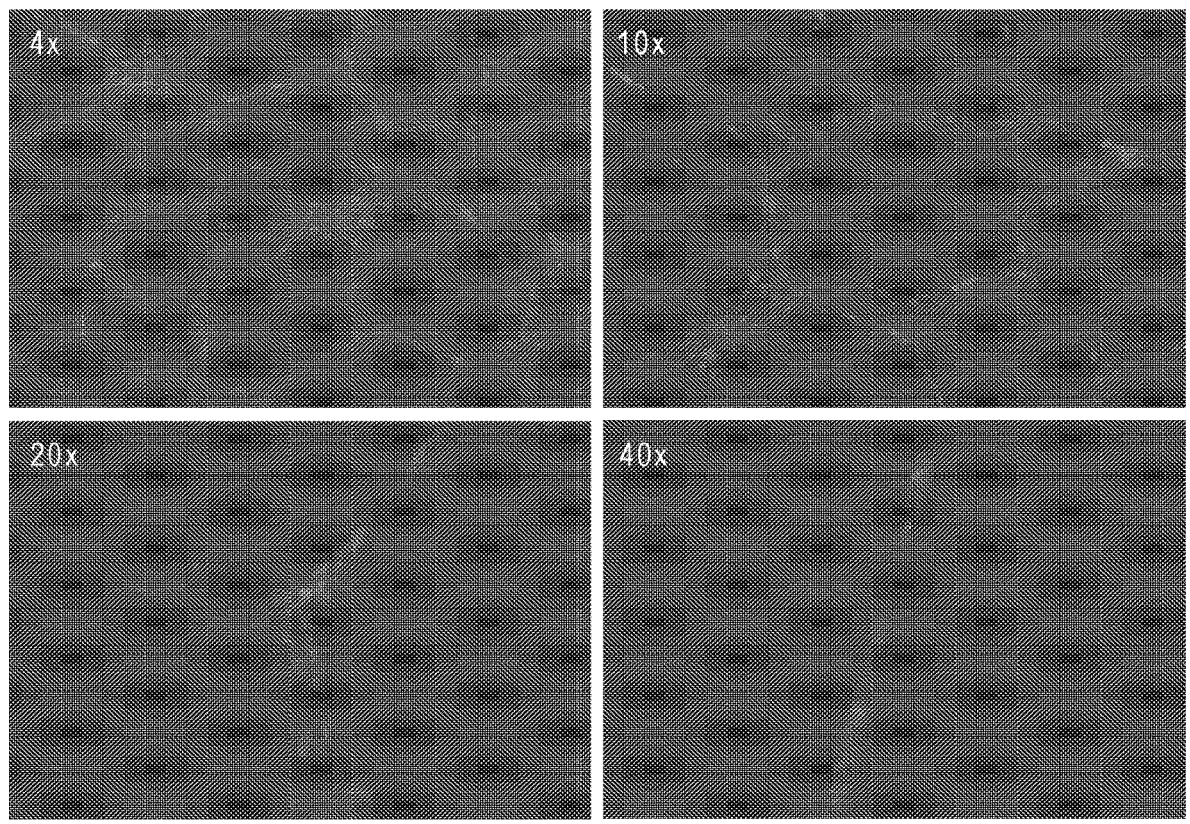
FIG. 6: Angiogenesis assay using Compound 2 (see, Example 4).

Angiogenesis: Human umbilical vein endothelial cells were plated on GELTREX (Thermo Fisher Scientific) coated plates at a density of 35,000 cells/cm$^2$ and incubated for 45 minutes. The cells were then labeled with 1 µM Compound 2 for 30 minutes in LCIS. LCIS removed and M-200 media with LVES was placed back on cells. Cells were incubated at 37° C. with 5% CO$_2$ for 20 hours and imaged. The results are shown in FIG. 6.

Example 5: Cell Differentiation Analysis

Figure 7:
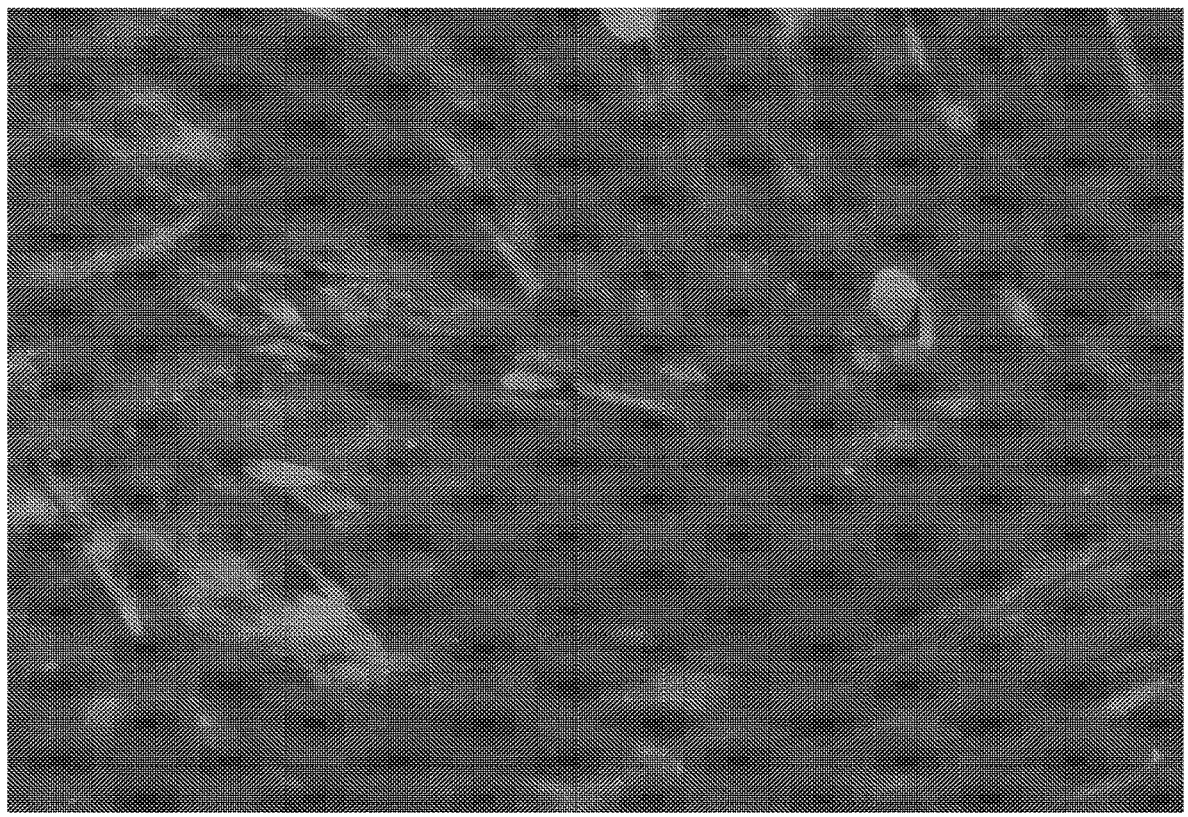
FIG. 7: Differentiation assay using Compound 2 (see, Example 5).

Human Skeletal Myoblast Differentiation: Human skeletal myoblast were plated on 24 well plates at a density of 240,000 cells/well. Cells were incubated for 4 hours in DMEM+20% FBS to let the cells attach to the plate. Next, cells were labeled with 1 µM Compound 2 for 30 minutes in LCIS. LCIS removed and low glucose DMEM media with 2% horse serum was placed on cells. Cells were incubated for 44 hours to let the cells differentiate into muscle fibers. Cells were then imaged. The results are shown in FIG. 7.

Example 6: Reaction of Goat Anti-Mouse IgG (GAM) and Sulfonated Carbopyronine (Compound 18)

0.12 mL (1 mg) of an 8.4 mg/mL solution of GAM in 10 mM potassium phosphate, 150 mM sodium chloride buffer (PBS) was measured into a plastic vial and the pH raised to 8.5-9.0 with 12 µL 1 M sodium bicarbonate, pH 9.0. The GAM solution was reacted with a 5-fold molar excess of the sulfonated carbopyronine (Compound 18) at 10 mg/mL in anhydrous DMSO for 1 h at room temperature while stirring gently. The dye-protein conjugate was separated from free dye by size exclusion chromatography using a 0.75×20 cm column packed with BIO-RAD BIO-GEL P-30 (Bio-Rad Laboratories, Inc.) fine in PBS and eluted with same. The initial protein-containing band from the column was collected. The absorbance spectrum was measured using a PerkinElmer Lambda 35 UV/Vis spectrometer. The fluorescence emission spectrum was obtained using a PerkinElmer LS 55 Fluorescence Spectrometer, excited at 610 nm.

Figure 8:
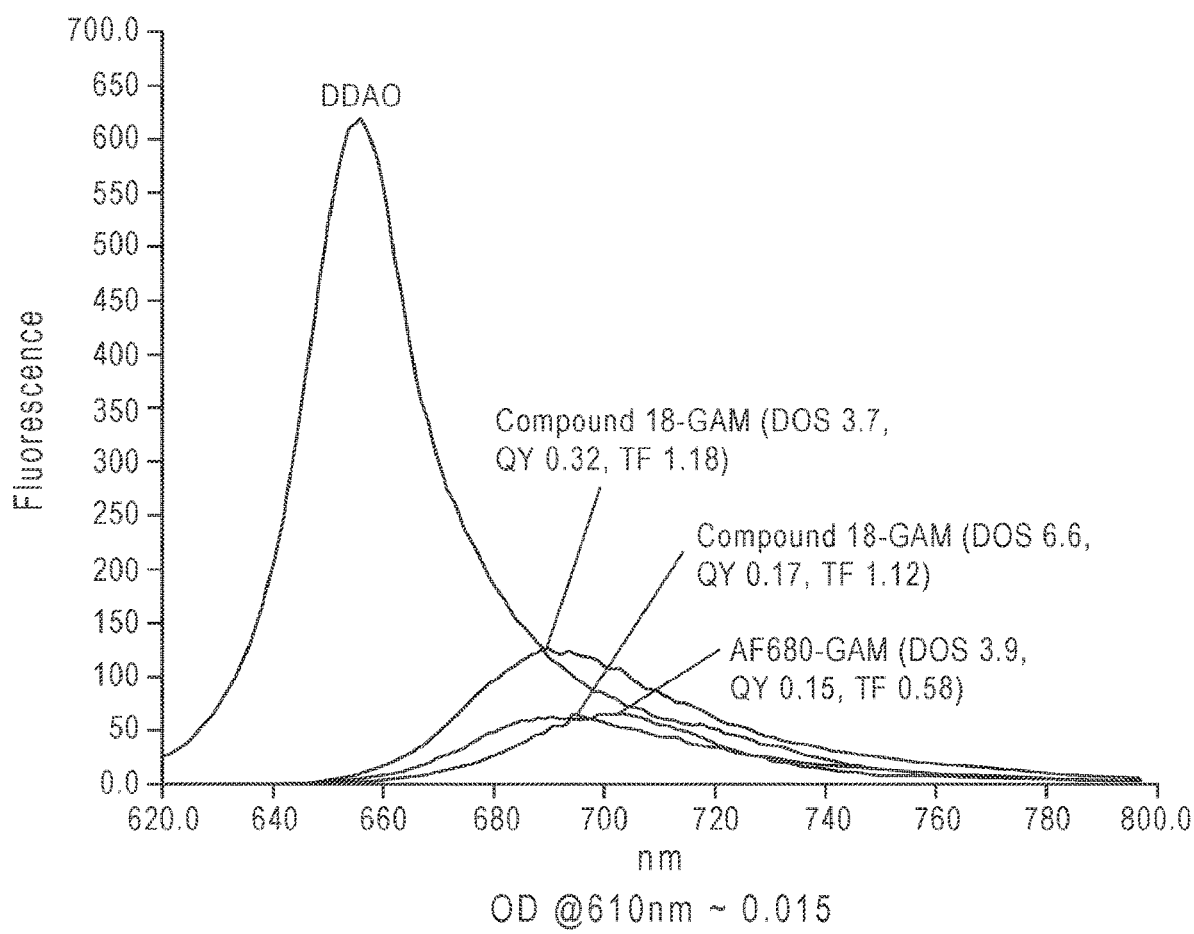
FIG. 8: Bioconjugation results of reacting goat-anti-mouse (GAM) IgG with Compound 18 (see, Example 6).

As shown in FIG. 8, the DOS for the conjugated form of Compound 18 is 3.7, whereas the DOS for the conjugated form of a similarly colored dye (ALEXA FLUOR 680) is 3.9. At these similar DOS levels, the Compound 18-GAM conjugate brightness is >2× that of the ALEXA FLUOR 680-GAM conjugate.

Example 7: Bead Staining with Compound 25

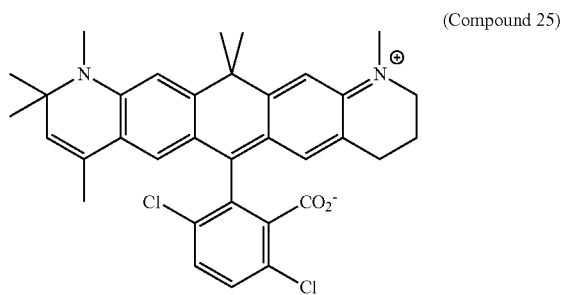

(Compound 25)

To 0.7 mL of a 5.2 µM PEGylated latex beads solution, add 0.35 mL methanol and stir at room temperature for five minutes, followed by adding 0.8 mg Compound 25 dissolved in 540 µL dichloromethane and 125 µL ethanol solution drop by drop. Continue to stir the bead staining solution at room temperature for 30 minutes followed by removal of organic solvent from the bead solution with a rotovap. Finally, filter the bead solution through a 0.2 µm filter to obtain the stained latex beads.

The stained beads have an emission maximum at 690 nm, 15% quantum yield when excited at 633 nm, and about $4.5 \times 10^6$ $M^{-1}$ $cm^{-1}$ extinction coefficient at 633 nm.

Example 8: Reaction of Allophycocyanin (APC) and Compound 18, Succinimidyl Ester (SE)

0.3 mL (3 mg) of a 10 mg/mL solution of APC in 0.1 M sodium phosphate, 0.1 M sodium chloride buffer, pH 7.5 was reacted with a 5, 10, or 120-fold molar excess of Compound 18 at 10 mg/mL in anhydrous dimethylsulfoxide (DMSO) for 1.5 hours at room temperature (RT). The dye-protein conjugates were separated from free dye by size exclusion chromatography using 3-1.5×10 cm columns packed with BIORAD BIO-GEL P-30 fine in 0.1M sodium phosphate, 0.1 M sodium chloride buffer, pH 7.5 and eluted with same.

The initial protein-containing band from each column was collected. The absorbance spectra were obtained on a PerkinElmer Lambda 35 UV/VIS spectrometer. The fluorescence emission spectra were obtained using a PerkinElmer LS55 Fluorescence Spectrometer, excited at 633 nm. The conjugates show a shift in emission from 660 nm to 690 nm compared to unmodified APC excited at the same wavelength.

The complex may be further modified by the conjugation of approximately 1-2 moles of SPDP (3-(2-pyridyldithio) propionic acid succinimidyl ester), to give a pyridyldisulfide-modified protein. Following reduction of the disulfide, such as with dithiothreitol (DTT), this thiolated protein is readily conjugated to any thiol-reactive second protein, such as mouse anti-human CD4 that has been modified by SMCC (4-(N-maleimidomethyl)-cyclohexane-1-carboxylic acid succinimidyl ester). The labeled mouse anti-human CD4 is then typically purified using size-exclusion chromatography. Covalent conjugates of molecules other than proteins, such as oligonucleotides, nucleic acids, microspheres, liposomes and so forth are readily prepared by similar methods using the same or other crosslinking reagents known in the art.

Flow Cytometry:

Candidates were conjugated to mouse monoclonal antibody against human CD4 (clone S3.5). White blood cells were prepared from ammonium chloride-lysed whole blood. Antibody conjugates, made with experimental compounds or with reference fluorochromes, were diluted in 1% BSA in PBS, pH7.4, and 10 µL of the conjugates were added to 90 µL of $1 \times 10^6$ cells. Conjugates and cells were allowed to incubate for 20 minutes at room temperature. After which, the cells were washed 2 times in 1% BSA in PBS, pH7.4. After the final wash, the cells were resuspended in 500 µL of 1% BSA in PBS, pH7.4. Stained cells were analyzed using the ATTUNE Acoustic Focusing Cytometer (Thermo Fisher Scientific). For CD4 specific staining, 10,000 lymphocyte events were collected, and data was represented as a histogram. Bi-Markers or histogram markers were inserted to help determine the percentage of CD4+ cells in the lymphocyte population. This was used as criteria to determine if there were any effects of the fluorochrome, conjugation methodology on the antibody performance. In addition, values from the mean fluorescence intensities of both the negative and positive peaks, as well as the standard deviation of the negative peak were used to determine the staining index of the conjugate tested. Comparison of the staining indexes was used to aid in determining the performance of different conjugates.

Figure 9A:
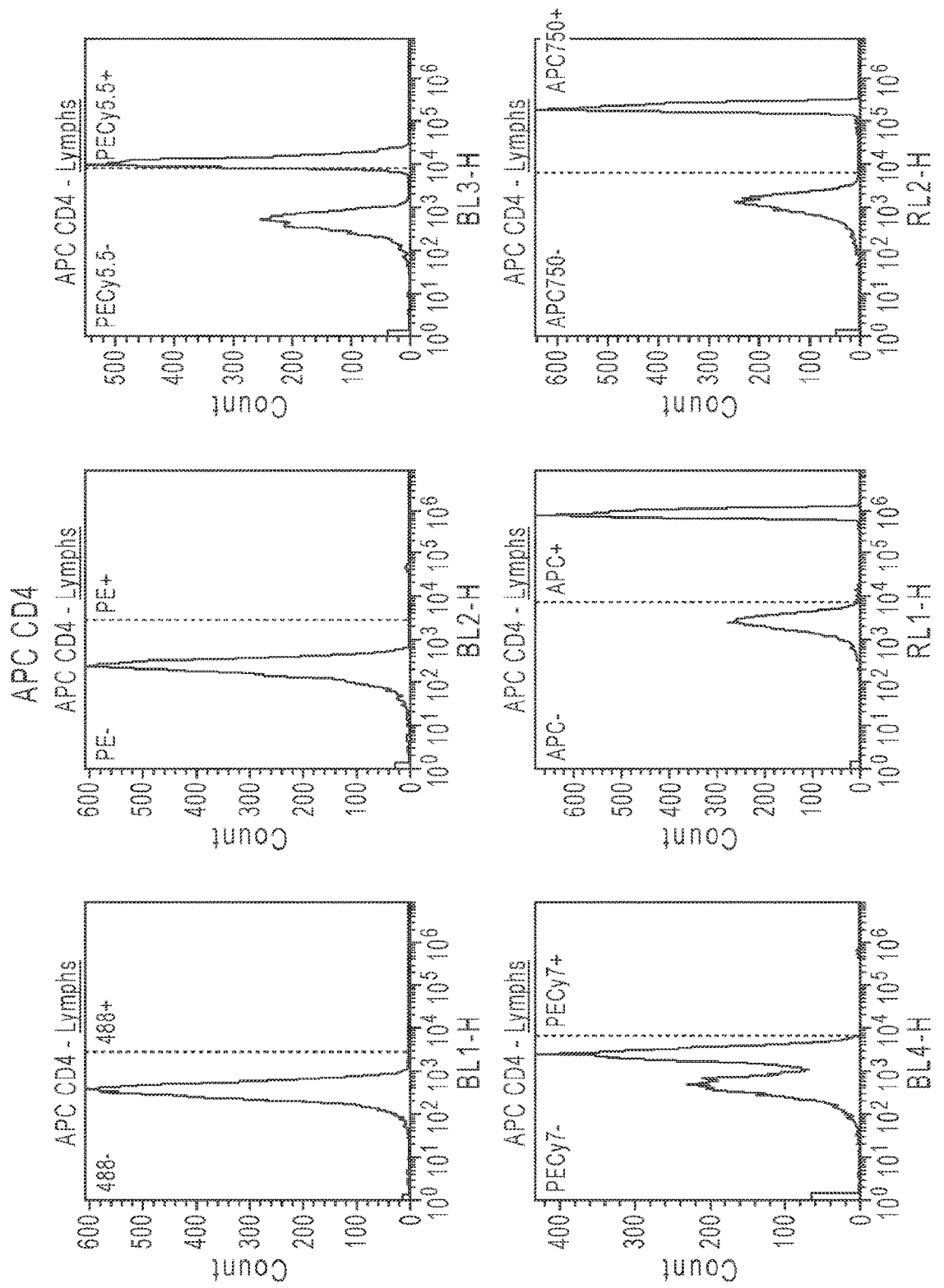
FIG. 9A: Flow cytometry histograms showing signal from lymphocytes stained with APC-CD4 conjugate in four emission channels: BL1-H (530/30 nm), BL2-H (574/26 nm), BL3 (690/50 nm), BL4 (780/60), RL1 (660/20 nm), RL2-H (780/60 nm) (see, Example 8).
Figure 9B:
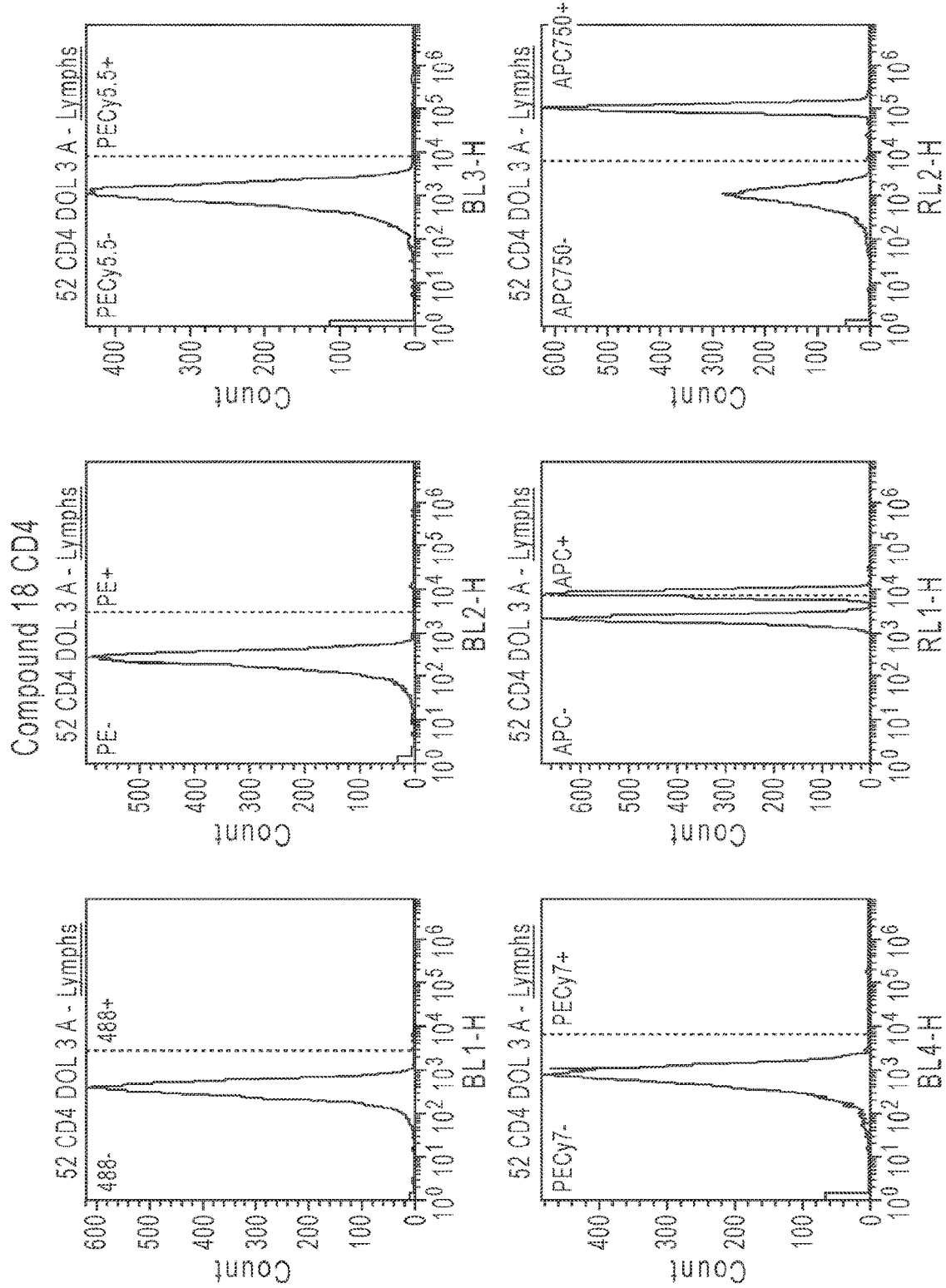
FIG. 9B: Flow cytometry histograms showing signal from lymphocytes stained with Compound 18-CD4 conjugate in four emission channels: BL1-H (530/30 nm), BL2-H (574/ 26 nm), BL3 (690/50 nm), BL4 (780/60 nm), RL1 (660/20 nm), RL2-H (780/60 nm). Note the lack of spillover in BL3-H, BL4-H, and RL1-H, compared with that from APC-CD4 in FIG. 9A; Compound 18-CD4 enables bright signal specifically in RL2, in contrast to signal in multiple channels using APC-CD4 (see, Example 8).
Figure 9C:
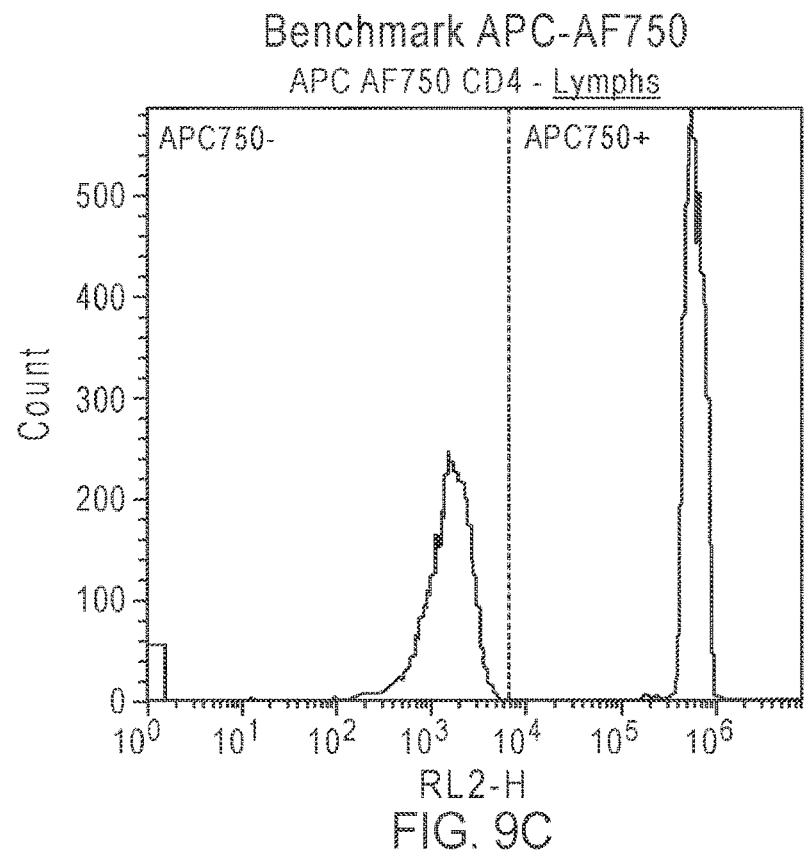
FIGS. 9C and 9D: Flow cytometry histograms showing signal in the RL2-H channel (780/60 nm) from lymphocytes stained with tandem dye conjugates APC-ALEXA FLUOR 750-CD4 (left) and APC-Compound 18-CD4 (right). (see, Example 8)
Figure 9D:
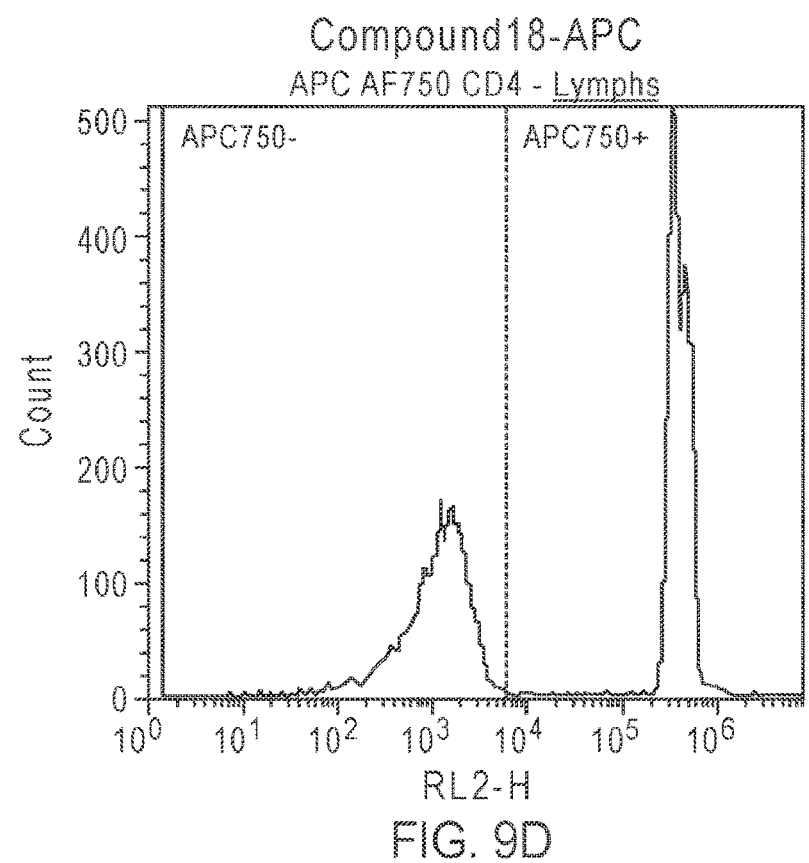
Figure 9E:
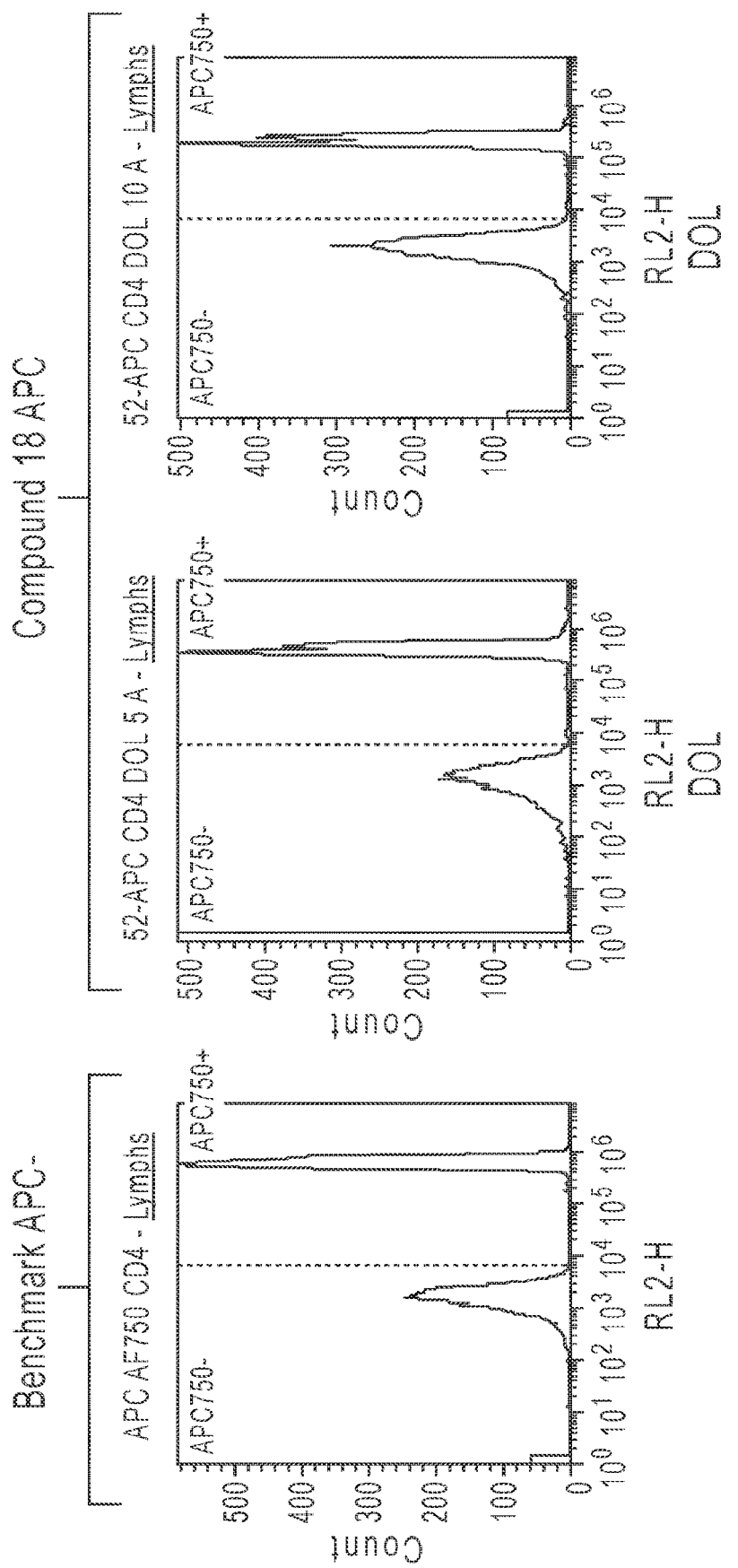
FIG. 9E: Flow cytometry histograms showing signal from lymphocytes stained with tandem dye conjugates of CD4 in the RL2-H channel (705/40 nm). Left histogram shows signal from cells stained with APC-ALEXA FLUOR 750-CD4, middle histogram shows signal from APC-Compound 18-CD4 DOL 5, and right histogram shows signal from APC-Compound 18-CD4 DOL10. The term DOL refers to the number of molecules of Compound 18 per number of molecules of APC in the tandem conjugates. The Table shows the improved SI (Staining Index) and Signal/Noise (S:N) of conjugates made with Compound 18 over those made with ALEXA FLUOR 750 (Thermo Fisher Scientific) (see, Example 8).

As shown in FIG. 9A, the flow cytometry histograms showing signal from lymphocytes stained with APC-CD4 conjugate in four emission channels: BL1-H (530/30 nm), BL2-H (574/26 nm), BL3 (690/50 nm), BL4 (780/60), RL1 (660/20 nm), RL2-H (780/60 nm). FIG. 9B shows flow cytometry histograms showing signal from lymphocytes stained with Compound 18-CD4 conjugate in four emission channels: BL1-H (530/30 nm), BL2-H (574/26 nm), BL3 (690/50 nm), BL4 (780/60 nm), RL1 (660/20 nm), RL2-H (780/60 nm). Note the lack of spillover in BL3-H, BL4-H, and RL1-H, compared with that from APC-CD4 in FIG. 9A; Compound 18-CD4 enables bright signal specifically in RL2, in contrast to signal in multiple channels using APC-CD4. FIGS. 9C and 9D show flow cytometry histograms showing signal in the RL2-H channel (780/60 nm) from lymphocytes stained with tandem dye conjugates APC-ALEXA FLUOR 750-CD4 (left) and APC-Compound 18-CD4 (right). FIG. 9E shows flow cytometry histograms showing signal from lymphocytes stained with tandem dye conjugates of CD4 in the RL2-H channel (705/40 nm). Left histogram shows signal from cells stained with APC-ALEXA FLUOR 750-CD4, middle histogram shows signal from APC-Compound 18-CD4 DOL 5, and right histogram shows signal from APC-Compound 18-CD4 DOL10. The term DOL refers to the number of molecules of Compound 18 per number of molecules of APC in the tandem conjugates. Table 4 shows the improved SI (Staining Index) and Signal/Noise (S:N) of conjugates made with Compound 18 over those made with ALEXA FLUOR 750 (Thermo Fisher Scientific).

TABLE 4

Staining Index and Signal:Noise Ratio of Compound 18 Conjugates

| 705/40 nm | Neg | Pos | SD | SI | S:N |
|---|---|---|---|---|---|
| APC-AF750 | 968 | 41176 | 474 | 42 | 43 |
| 18-APC DOL 5 | 5632 | 1433019 | 3484 | 205 | 254 |
| 18-APC DOL 10 | 4973 | 700962 | 3149 | 111 | 141 |

Example 9: Cytotoxicity Analysis of Compound 2

Figure 10:
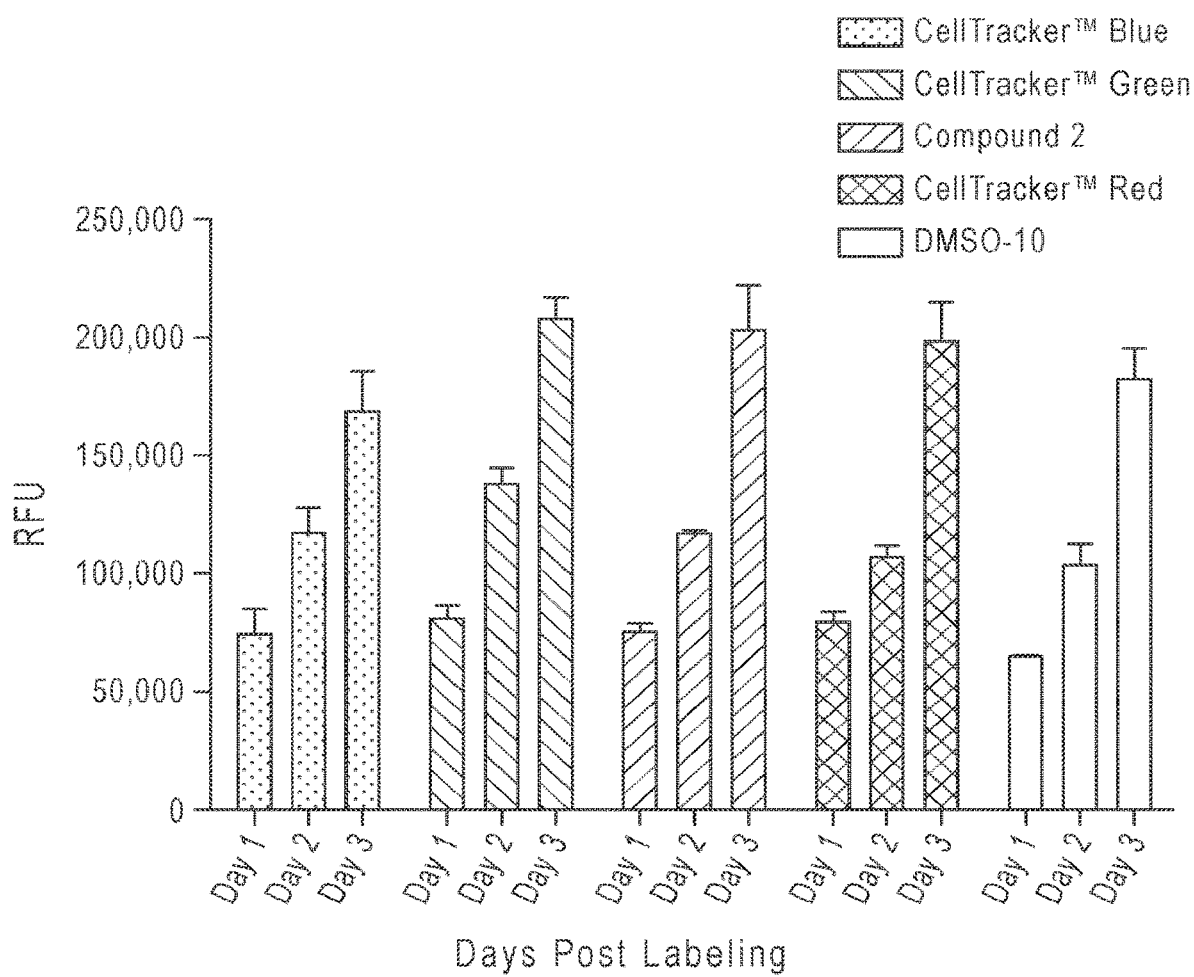
FIG. 10: Lack of cytotoxicity of Compound 2, as measured by the CYQUANT Direct (Thermo Fisher Scientific) method. Fluorescence on the Y-axis is proportional to cell population viability. A549 cells plated in a 96 well plate were labeled with CELLTRACKER Blue, Green, Red, Compound 2, or DMSO in Live Cell Imaging Solution at 10 μM concentration for 30 mins at 37° C. The LCIS was then aspirated from cells and complete media added for an overnight incubation. The following day (Day 1) cells were assayed for cytotoxicity using the CYQUANT Direct assay (Thermo Fisher Scientific). The CYQUANT Direct assay was repeated on cells from the same 96 well plate on days 2 and 3 showing no cytotoxicity of CELLTRACKER Blue, Green, Red or Compound 2 when compared to DMSO alone (see, Example 9).

FIG. 10 demonstrates the lack of cytotoxicity of Compound 2, as measured by the CYQUANT Direct (Thermo Fisher Scientific) method. Fluorescence on the Y-axis is proportional to cell population viability. A549 cells plated in a 96 well plate were labeled with CELLTRACKER Blue, Green, Red, Compound 2, or DMSO in Live Cell Imaging Solution at 10 µM concentration for 30 mins at 37° C. The LCIS was then aspirated from cells and complete media added for an overnight incubation. The following day (Day 1) cells were assayed for cytotoxicity using the CYQUANT Direct assay (Thermo Fisher Scientific). The CYQUANT Direct assay was repeated on cells from the same 96 well plate on days 2 and 3 showing no cytotoxicity of CELL-TRACKER Blue, Green, Red or Compound 2 when compared to DMSO alone.

We claim:

1. A method for tracking cell proliferation, differentiation, and/or function, the method comprising the steps of:
a) incubating a mixture of cells and a compound of structural formula (III):

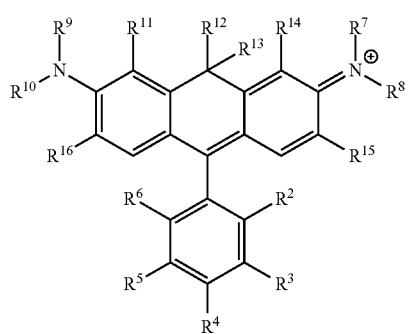

(I)

or a pharmaceutically acceptable salt thereof, wherein
$R^{12}$ and $R^{13}$ are each independently H, $C_1$-$C_6$ alkyl, substituted $C_1$-$C_6$ alkyl, -L-$R_x$, or -L-$S_c$;
$R^2$ is carboxyl, -L-$R_x$, or -L-$S_c$;
$R^3$, $R^4$, $R^5$ and $R^6$ are each independently H or halogen;
$R^{11}$, $R^{14}$, $R^{18}$ and $R^{23}$ are H;
$R^7$, $R^9$, $R^{17}$, $R^{19}$, $R^{20}$, $R^{22}$, $R^{23}$, and $R^{24}$ are each independently H, $C_1$-$C_6$ alkyl, substituted $C_1$-$C_6$ alkyl, sulfoalkyl, -L-$R_x$, or -L-$S_c$;
L is a linker;
$R_x$ is an acrylamide, a carboxylic acid, an activated ester of a carboxylic acid, an acyl azide, an acyl halide, hydroxy, an aldehyde, an alkyl halide, a sulfonate, an amine, an anhydride, an aniline, an aryl halide, an azide, an aziridine, a boronate, a carbodiimide, a diazoalkane, an epoxide, a glycol, a haloacetamide, a halotriazine, a hydrazine, a hydroxylamine, an imido ester, an isothiocyanate, a ketone, a maleimide, a sulfonyl halide, a thiol group, a succinimidyl ester (SE), a sulfodichlorophenyl (SDP) ester, a sulfotetrafluorophenyl (STP) ester, a tetrafluorophenyl (TFP) ester, a pentafluorophenyl (PFP) ester, a nitrilotriacetic acid (NTA), an aminodextran, or a cyclooctyne-amine; and
$S_c$ is a conjugated substance; or
a compound of structural formula (IV):

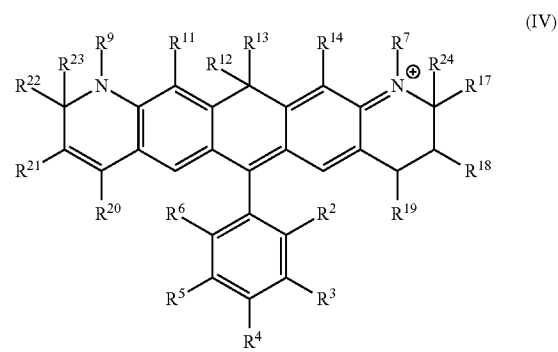

(IV)

or a pharmaceutically acceptable salt thereof, wherein
$R^{12}$ and $R^{13}$ are each independently H, $C_1$-$C_6$ alkyl, substituted $C_1$-$C_6$ alkyl, -L-$R_x$, or -L-$S_c$;

$R^2$ is carboxyl, -L-$R_x$, or -L-$S_c$;

$R^3$, $R^4$, $R^5$ and $R^6$ are each independently H or halogen;

$R^{11}$, $R^{14}$, $R^{18}$ and $R^{21}$ are H;

$R^7$, $R^9$, $R^{17}$, $R^{19}$, $R^{20}$, $R^{22}$, $R^{23}$, and $R^{24}$ are each independently H, $C_1$-$C_6$ alkyl, substituted $C_1$-$C_6$ alkyl, sulfoalkyl, L-$R_x$, or -L-$S_c$;

L is a linker;

$R_x$ is an acrylamide, a carboxylic acid, an activated ester of a carboxylic acid, an acyl azide, an acyl halide, hydroxy, an aldehyde, an alkyl halide, a sulfonate, an amine, an anhydride, an aniline, an aryl halide, an azide, an aziridine, a boronate, a carbodiimide, a diazoalkane, an epoxide, a glycol, a haloacetamide, a halotriazine, a hydrazine, a hydroxylamine, an imido ester, an isothiocyanate, a ketone, a maleimide, a sulfonyl halide, a thiol group, a succinimidyl ester (SE), a sulfodichlorophenyl (SDP) ester, a sulfotetrafluorophenyl (STP) ester, a tetrafluorophenyl (TFP) ester, a pentafluorophenyl (PFP) ester, a nitrilotriacetic acid (NTA), an aminodextran, or a cyclooctyne-amine; and $S_c$ is a conjugated substance;

b) providing a stimulus to the mixture to elicit a fluorescent signal; and c) analyzing the stimulated mixture.

2. The method according to claim 1, further comprising a second compound excitable at a different wavelength than the compound of structural formula (III) or structural formula (IV).

3. The method according to claim 2, wherein the second compound is CFDA-SE or GFP.

4. The method according to claim 1, wherein the compound is selected from the group consisting of:

Compound 4

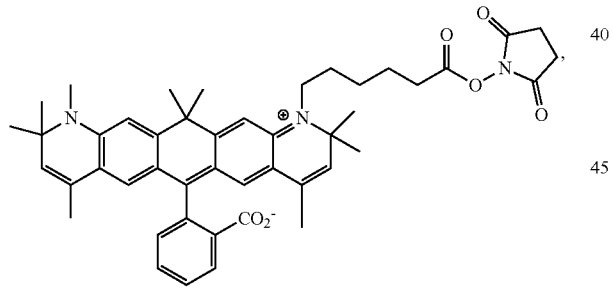

Compound 7

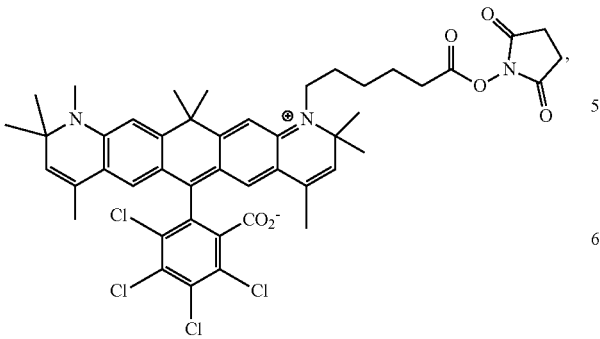

Compound 16

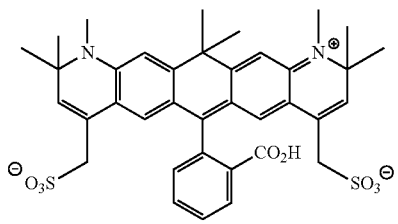

Compound 17

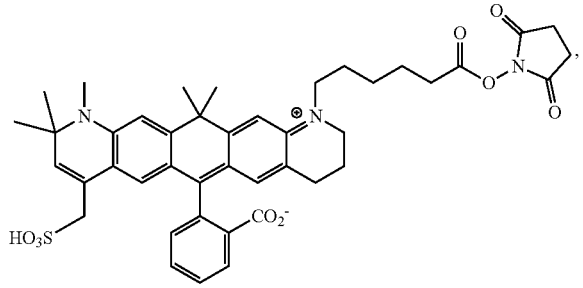

Compound 18

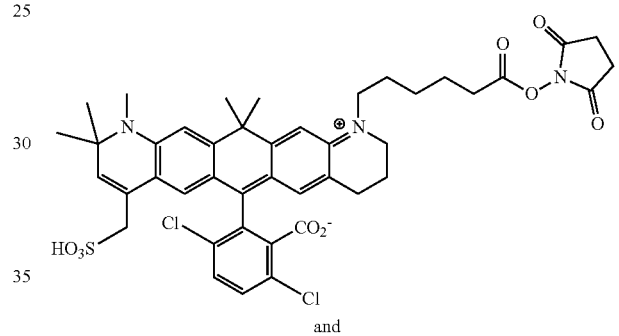

and

Compound 25

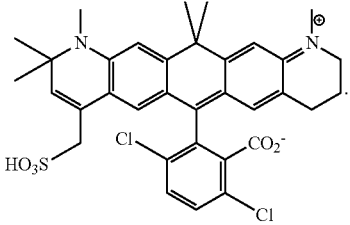

5. The method according to claim 1, wherein $S_c$ is an amino acid, a peptide, a protein, a monosaccharide, a polysaccharide, an ion-complexing moiety, a nucleotide, an oligonucleotide, a nucleic acid, a hapten, a drug, a toxin, a lipid, a phospholipid, a lipoprotein, a lipopolysaccharide, a liposome, a lipophilic polymer, a PEG group, a non-biological organic polymer, a polymeric microparticle, an animal cell, a plant cell, a bacterium, a yeast, or a virus.

6. The method according to claim 1, wherein step a) is conducted for approximately 20 minutes.

7. The method according to claim 1, wherein step b) and step c) are carried out concurrently.

8. The method according to claim 1, wherein analyzing the stimulated mixture of step c) is performed by flow cytometry.

* * * * *

SEQUENCE LISTING

```
<160> NUMBER OF SEQ ID NOS: 1

<210> SEQ ID NO 1
<211> LENGTH: 4
<212> TYPE: PRT
<213> ORGANISM: Unknown
<220> FEATURE:
<221> NAME/KEY: source
<223> OTHER INFORMATION: /note="Description of Unknown: Caspase
      recognition site peptide"

<400> SEQUENCE: 1

Asp Glu Val Asp
1
```